(12) United States Patent
Prybolsky et al.

(10) Patent No.: US 11,495,339 B2
(45) Date of Patent: Nov. 8, 2022

(54) METHODS FOR LOWERING BLOOD SUGAR WITH A GLIFLOZIN SODIUM-GLUCOSE COTRANSPORT 2 INHIBITOR PHARMACEUTICAL COMPOSITION

(71) Applicant: AstraZeneca UK Limited

(72) Inventors: Robert Peter Prybolsky, West Chester, PA (US); Judy Firor, Landenberg, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 200 days.

(21) Appl. No.: 16/440,737

(22) Filed: Jun. 13, 2019

(65) Prior Publication Data

US 2019/0385725 A1    Dec. 19, 2019

Related U.S. Application Data

(60) Provisional application No. 62/685,202, filed on Jun. 14, 2018.

(51) Int. Cl.
*G16H 20/13*    (2018.01)
*G16H 10/60*    (2018.01)
(Continued)

(52) U.S. Cl.
CPC .......... *G16H 20/13* (2018.01); *A61K 31/70* (2013.01); *G16H 10/20* (2018.01); *G16H 10/40* (2018.01); *G16H 10/60* (2018.01); *G16H 70/40* (2018.01)

(58) Field of Classification Search
CPC ........ G16H 10/20; G16H 20/10; G16H 20/13; G16H 70/40
See application file for complete search history.

(56) References Cited

U.S. PATENT DOCUMENTS

| 7,493,264 B1 | 2/2009 | Kelly et al. |
| 2005/0108053 A1 | 5/2005 | Jones |

(Continued)

FOREIGN PATENT DOCUMENTS

| WO | WO 2010/041052 A1 | 4/2010 | |
| WO | WO-2010041052 A1 * | 4/2010 | ......... G06F 19/3456 |
| WO | WO 2012/041898 A1 | 4/2012 | |

OTHER PUBLICATIONS

FDA, Highlights of Prescribing Information—Farxiga (dapagliflozin) tablets, Oct. 2017, FDA (Year: 2017).*

(Continued)

*Primary Examiner* — Linh Giang Le
*Assistant Examiner* — Constantine Siozopoulos
(74) *Attorney, Agent, or Firm* — Brett A. Lovejoy; Andrew J. Antczak; Morgan, Lewis & Bockius LLP

(57) ABSTRACT

A method is provided for lowering blood sugar in a subject in need thereof by administering a gliflozin Sodium-Glucose Cotransport 2 inhibitor pharmaceutical composition to a subject qualified for over-the-counter access to the gliflozin Sodium-Glucose Cotransport 2 inhibitor pharmaceutical composition. In some embodiments, the gliflozin Sodium-Glucose Cotransport 2 inhibitor pharmaceutical composition includes empagliflozin, canagliflozin, and ertugliflozin. In some embodiments, the gliflozin Sodium-Glucose Cotransport 2 inhibitor pharmaceutical composition includes (2S, 3R,4R,5S,6R)-2-[4-chloro-3-[(4-ethoxyphenyl)methyl]phenyl]-6-(hydroxymethyl)oxane-3,4,5-triol or a pharmaceutically acceptable salt thereof.

19 Claims, 24 Drawing Sheets

(51) Int. Cl.
G16H 70/40 (2018.01)
G16H 10/20 (2018.01)
G16H 10/40 (2018.01)
A61K 31/70 (2006.01)

(56) References Cited

U.S. PATENT DOCUMENTS

| | | | | |
|---|---|---|---|---|
| 2009/0125324 | A1 | 5/2009 | Keravich et al. | |
| 2011/0166876 | A1 | 7/2011 | Chapman | |
| 2011/0178812 | A1 | 7/2011 | Lindsay | |
| 2012/0150562 | A1* | 6/2012 | Lerner | G16H 10/60 705/3 |
| 2013/0218586 | A1* | 8/2013 | Huser | G06Q 20/20 705/2 |
| 2018/0165739 | A1* | 6/2018 | Lawless | G16H 10/60 |

OTHER PUBLICATIONS

International Search Report and Written Opinion for International Patent Application No. PCT/US2019/037068, dated Nov. 14, 2019, 28 pages.
Reilly et al., "Carcinogenicity Risk Assessment Supports the Chronic Safety of Dapagliflozin, an Inhibitor of Sodium-Glucose Co-Transporter 2, in the Treatment of Type 2 Diabetes Mellitus", Diabetes Therapy, vol. 5, No. 1, Jan. 29, 2014.
Baker et al., "Effects of Sodium-Glucose Cotransporter 2 Inhibitors on 24-Hour Ambulatory Blood Pressure: A Systemic Review and Meta-Analysis", Journal of the American Heart Association, vol. 6, No. 5, May 5, 2017.
Ramkumar, S. et al., Acta Cardiol. Sin., 32(6):631-39 (2016).
Barias S. FDA Considers a New Paradigm For Over-the-Counter Medications: More Power—but More Burdens—for Pharmacists and Pharmacies. P T. May 2012;37(5):300-5. PubMed PMID: 22876088; PubMed Central PMCID: PMC3411219.
Crestor, Full Prescribing Information, 2012, AstraZeneca Pharmaceuticals LP.
Dyer O., "FDA Rejects sale of over the counter Statins", BMJ, Jan. 22, 2005; 330(7484):164.
May 9, 2013, power point presentations from the Engelberg Center for Health Care Reform.
Pfizer Wants Atorvastatin Available Over the Counter—Medscape—Aug. 4, 2011, downloaded from the Internet Nov. 30, 2018.
PR Newswire Association, "Americans Should Pay More Attention to Over-the-Counter (OTC) medicine Labels According to New Survey", Oct. 15, 2015 (citing McNeil Consumer Healthcare research).
Farxiga (dapagliflozin) Tablets Prescribing Information, (Bristol-Myers Squibb Company), Aug. 2014, [online], [retrieved on Feb. 28, 2021], Retrieved from the Internet: <URL: https://www.accessdata.fda.gov/drugsatfda_docs/label/2014/202293s003lbl.pdf>.
Jardiance (empagliflozin) Tablets Prescribing Information, (Boehringer Ingelheim Pharmaceuticals, Inc.), Dec. 2016, [online], [retrieved on Feb. 28, 2021] Retrieved from the Internet: <URL: https://www.accessdata.fda.gov/drugsatfda_docs/label/2016/204629s008lbl.pdf>.
Invokana (canagliflozin) Tablets Prescribing Information, (Janssen Ortho), Mar. 2016, [online], [retrieved on Feb. 28, 2021] Retrieved from the Internet: <URL: https://www.accessdata.fda.gov/drugsatfda_docs/label/2016/204042s011lbl.pdf >.
Steglatro (ertugliflozin) Tablets Prescribing Information, (Covis Pharma), Dec. 2017, [online], [retrieved on Feb. 28, 2021] Retrieved from the Internet: <URL: https://www.accessdata.fda.gov/drugsatfda_docs/label/2017/209803s000lbl.pdf >.
EMA Invokana Label: InvokanaTablets—Summary of Product Characteristics; European Medicines Agency (EMA): https://www.ema.europa.eu/en/documents/product-information/invokana-epar-product-information_en (50 pgs) (Aug. 27, 2021).
Farxiga (dapagliflozin) Drug Facts Label: https://www.accessdata.fda.gov/drugsatfda_docs/label/2014/202293s003lbl (43 pgs) (Aug. 2014).
Both et al., Analysis of licensed over-the-counter (OTC) antibiotics in the European Union and Norway. Euro Surveill (2015).
Chang et al., Prescription to over-the-counter switches in the United States. Journal of Research in Pharmacy Practice. (2016).
Ferris et al., Over-the-Counter Antifungal Drug Misuse Associated With Patient-Diagnosed Vulvovaginal Candidiasis. Antifungal Drug Misuse. Obstetrics & Gynecology. vol. 99, No. 3, (2002) The American College of Obstetricians and Gynecologists.
Stomberg et al., Utilization effects of Rx-OTC switches and implications for future switches. Health. vol. 5, No. 10, 1667-1680 (2013).
Yuen and Chong, Rx-to-OTC Switch—An Overview and its Implications to Public Health. Pharmacy Education & Practice. vol. 25, No. 4 (2018).

* cited by examiner

400

(402) A computer system for qualifying a human subject for over-the-counter delivery of a gliflozin Sodium-Glucose Cotransport 2 inhibitor pharmaceutical composition for lowering blood sugar. The computer system includes one or more processors and a memory. The memory includes non-transitory instructions which, when executed by the one or more processor, perform a method (403) The gliflozin Sodium-Glucose Cotransport 2 inhibitor pharmaceutical composition has a structure of structure (I)

(404) The gliflozin Sodium-Glucose Cotransport 2 inhibitor pharmaceutical composition includes dapagliflozin or a pharmaceutically acceptable salt thereof (405) The gliflozin Sodium-Glucose Cotransport 2 inhibitor pharmaceutical composition is dapagliflozin propanediol (406) The gliflozin Sodium-Glucose Cotransport 2 inhibitor pharmaceutical composition is selected from the group consisting of empagliflozin, canagliflozin, and ertugliflozin (407) The lowering blood sugar is to treat or prevent Type 2 diabetes

(408) Conduct a first survey of the subject thereby obtaining a first plurality of survey results (409) The first plurality of survey results includes whether the subject is one of (i) pregnant, (ii) breastfeeding, or (iii) planning to become pregnant, a Type 1 diabetes status of the subject, a ketoacidosis status of the subject, a kidney disease status of the subject, an age of the subject, a blood sugar level of the subject, whether the subject has a liver problem, whether the subject has ever had a urinary problem, a surgery status of the subject, a dietary status of the subject, whether the subject has ever had a pancreatic problem, an alcohol consumption status of the subject, and whether the subject is taking a diabetes medication (410) The first plurality of survey results further includes whether the subject is allergic to the gliflozin Sodium-Glucose Cotransport 2 inhibitor pharmaceutical composition, and the first plurality of filters includes an adverse reaction filter that is fired when the first plurality of survey results indicates that the subject is allergic to the gliflozin Sodium-Glucose Cotransport 2 inhibitor pharmaceutical composition (411) The first plurality of survey results further includes whether the subject has ever had bladder cancer, and the first plurality of filters includes a first bladder cancer filter that is fired when the first plurality of survey results indicates that the subject has had bladder cancer

Fig. 4A

(412) Run all or a portion of the first plurality of survey results against a first plurality of filters of a first category class. When a respective filter in the first plurality of filters is fired, the subject is deemed not qualified for delivery of the gliflozin Sodium-Glucose Cotransport 2 inhibitor pharmaceutical composition and the method is terminated without delivery of the gliflozin Sodium-Glucose Cotransport 2 inhibitor pharmaceutical composition to the subject (413) The first plurality of filters includes a first pregnancy filter that is fired at least when the first plurality of survey results indicates that the subject is pregnant or the subject is breastfeeding (414) The first pregnancy filter is also fired when the first plurality of survey results indicates that the subject plans to become pregnant within a predetermined period of time (415) The first plurality of filters includes a Type 1 diabetes filter that is fired at least when the first plurality of survey results indicates that the subject has Type 1 diabetes (416) The first plurality of filters includes a first ketoacidosis filter that is fired at least when the first plurality of survey results indicates that the subject has ketoacidosis (417) The first plurality of filters includes a first kidney disease filter that is fired at least when the first plurality of survey results indicates that the subject has kidney disease (418) The first plurality of filters includes an age filter (419) The age filter is fired when the first plurality of survey results indicates that the subject is less than eighteen years old (490) The first plurality of filters further includes a bladder cancer status of the subject. And where the third plurality of filters further includes a second bladder cancer filter that is fired at least when the second plurality of survey results indicates that the subject has developed bladder cancer since receiving their last provision of the gliflozin Sodium-Glucose Cotransport 2 inhibitor pharmaceutical composition

*(420)* The first plurality of filters includes a first blood sugar filter that is fired at least when the first plurality of survey results indicates that the subject has a blood sugar level that is either below a first baseline blood sugar level or above a ceiling blood sugar level > *(421)* The first baseline blood sugar level used in the first blood sugar filter is 6.5% glycated hemoglobin > *(422)* The ceiling blood sugar level used in the first blood sugar filter is 8% glycated hemoglobin

*(423)* Run all or a portion of the first plurality of survey results against a second plurality of filters of a second category class. When a respective filter in the second plurality of filters is fired, the subject is provided with a warning corresponding to the respective filter > *(424)* The warning corresponding to a respective filter in the second plurality of filters includes a prompt for the subject to indicate whether they have discussed the risk factor underlying the respective filter in the second plurality of filters that was fired with a health care professional. Acknowledgement is obtained from the subject when the subject indicates that they have discussed the risk factor underlying the respective filter in the second plurality of filters that was fired with a health care professional > *(425)* The second plurality of filters includes a first liver disease filter that is fired at least when the first plurality of survey results indicates that the subject has had a liver problem > *(426)* The second plurality of filters includes a first urinary problem filter that is fired at least when the first plurality of survey results indicates that the subject has a history of urinary problems >> *(427)* The first urinary problem filter is also fired when the first plurality of survey results indicates that the subject has a history of urinary tract infections or problems urinating > *(428)* The second plurality of filters includes a first surgery filter that is fired when the first plurality of survey results indicates that the subject is planning on undergoing surgery

*(429)* The second plurality of filters includes a first dietary filter that is fired when the first plurality of survey results indicates that the subject is eating less than before > *(430)* The first dietary filter is fired when the first plurality of survey results indicates that the subject is eating less due to illness, surgery, or a recent change in diet

*(431)* The second plurality of filters includes a first pancreatic disease filter that is fired when the first plurality of survey results indicates that the subject has a pancreatic problem

*(432)* The second plurality of filters includes a first alcohol consumption filter > *(433)* The first alcohol consumption filter is also fired when the first plurality of survey results indicates that the subject, on average, consumes at least a predetermined number of alcoholic drinks over a predetermined period of time

*(434)* The second plurality of filters includes a first diabetes medication filter that is fired when the first plurality of survey results indicates that the subject is taking a diabetes medication

*(435)* Obtain acknowledgment from the subject for the warning issued to the subject by any filter in the second plurality of filters (D)

Fig. 4D

(436) Proceed with a fulfillment process when no filter in the first plurality of filters has been fired and the subject has acknowledged each warning associated with each filter in the second plurality of filters that was fired (437) The fulfillment process includes storing an indication in a subject profile of an initial order for the gliflozin Sodium-Glucose Cotransport 2 inhibitor pharmaceutical composition, communicating an over the counter drug facts label for the gliflozin Sodium-Glucose Cotransport 2 inhibitor pharmaceutical composition to the subject, and authorizing, upon confirmation from the subject that the over the counter drug facts label has been received and read, provision of the gliflozin Sodium-Glucose Cotransport 2 inhibitor pharmaceutical composition to the subject (438) Upon confirmation from the subject that the over the counter drug facts label has been received and read, the subject is authorized for provision of a dosage from 5 mg to 10 mg per day of the gliflozin Sodium-Glucose Cotransport 2 inhibitor pharmaceutical composition (439) Upon confirmation from the subject that the over the counter drug facts label has been received and read, the subject is authorized for provision of a dosage from 5 mg per day of the gliflozin Sodium-Glucose Cotransport 2 inhibitor pharmaceutical composition (440) The fulfillment process further includes storing a destination associated with the subject in the subject profile (441) The fulfillment process further includes coordinating shipping of the gliflozin Sodium-Glucose Cotransport 2 inhibitor pharmaceutical composition to a physical address associated with the subject (442) Responsive to receiving a re-order request from the subject for the gliflozin Sodium-Glucose Cotransport 2 inhibitor pharmaceutical composition, performing a re-fulfillment procedure

Fig. 4E

(443) Conduct a second survey of the subject thereby obtaining a second plurality of survey results (444) The second plurality of survey results includes whether the subject is one of (i) pregnant, (ii) breastfeeding, or (iii) planning to become pregnant, whether the subject has experienced a symptom of ketoacidosis since receiving their last provision of the gliflozin Sodium-Glucose Cotransport 2 inhibitor pharmaceutical composition, whether the subject has experienced a symptom of a kidney problem since receiving their last provision of the gliflozin Sodium-Glucose Cotransport 2 inhibitor pharmaceutical composition, whether the subject has experienced a symptom of a urinary problem since receiving their last provision of the gliflozin Sodium-Glucose Cotransport 2 inhibitor pharmaceutical composition, whether the subject has experienced a liver problem since receiving their last provision of the gliflozin Sodium-Glucose Cotransport 2 inhibitor pharmaceutical composition, a surgery status of the subject, a dietary status of the subject, whether the subject has experienced a pancreatic problem since receiving their last provision of the gliflozin Sodium-Glucose Cotransport 2 inhibitor pharmaceutical composition, an alcohol consumption status of the subject, whether the subject has experienced a yeast infection since receiving their last provision of the gliflozin Sodium-Glucose Cotransport 2 inhibitor pharmaceutical composition, whether the subject has experienced a symptom of hypoglycemia since receiving their last provision of the gliflozin Sodium-Glucose Cotransport 2 inhibitor pharmaceutical composition, whether the subject is experiencing a bodily stress, and whether the subject is taking a diabetes medication

(445) Run all or a portion of the second plurality of survey results against a third plurality of filters of the first category class. When a respective filter in the third plurality of filters is fired, the subject is deemed not qualified for the gliflozin Sodium-Glucose Cotransport 2 inhibitor pharmaceutical composition and the re-fulfillment process is terminated without delivery of the gliflozin Sodium-Glucose Cotransport 2 inhibitor pharmaceutical composition to the subject (446) The third plurality of filters includes a second pregnancy filter that is fired at least when the second plurality of survey results indicates that the subject is pregnant or the subject is breastfeeding (447) The second pregnancy filter is also fired when the first plurality of survey results indicates that the subject plans to become pregnant within a predetermined period of time

*(448)* The third plurality of filters includes a ketoacidosis symptom filter that is fired at least when the second plurality of survey results indicates that the subject has experienced symptoms of ketoacidosis since receiving their last provision of the gliflozin Sodium-Glucose Cotransport 2 inhibitor pharmaceutical composition

*(449)* A symptom of ketoacidosis that is capable of firing the ketoacidosis symptom filter is selected from the group consisting of an increase of ketones in the blood of the subject, an increase of ketones in the urine of the subject, nausea, tiredness, vomiting, trouble breathing, and abdominal pain

*(450)* The third plurality of filters includes a kidney problem filter that is fired at least when the second plurality of survey results indicates that the subject has experienced symptoms of a kidney problem since receiving their last provision of the gliflozin Sodium-Glucose Cotransport 2 inhibitor pharmaceutical composition

*(451)* A symptom of a kidney problem that is capable of firing the kidney problem symptom filter is selected from the group consisting of the subject is eating less than before, the subject is drinking less than before, vomiting, diarrhea, dehydration, and being diagnosed with kidney disease

*(452)* The third plurality of filters includes a second urinary problem filter that is fired at least when the second plurality of survey results indicates that the subject has experienced symptoms of a urinary tract infection since receiving their last provision of the gliflozin Sodium-Glucose Cotransport 2 inhibitor pharmaceutical composition

*(453)* A symptom of a urinary problem that is capable of firing the urinary problem filter is selected from the group consisting of a burning sensation when passing urine, an increased urge to urinate, pelvic pain, blood in the urine, fever, back pain, nausea, and vomiting

*(454)* The third plurality of filters includes a bodily stress filter that is fired at least when the second plurality of survey results indicates that the subject is experiencing a bodily stress

*(455)* A bodily stress that is capable of firing the bodily stress filter is selected from the group consisting of fever, a recent trauma, an infection, and a recent surgery (G)

(456) The third plurality of filters includes a second diabetes medication filter that is fired at least when the second plurality of survey results indicates that the subject is taking a diabetes medication (457) Run all or a portion of the second plurality of survey results against a fourth plurality of filters of the second category class. When a respective filter in the fourth plurality of filters is fired, the subject is provided with a warning corresponding to the respective filter (458) The fourth plurality of filters includes a second liver disease filter that is fired at least when the second plurality of survey results indicates that the subject has developed a liver problem since receiving their last provision of the gliflozin Sodium-Glucose Cotransport 2 inhibitor pharmaceutical composition (459) The fourth plurality of filters includes a second surgery filter that is fired at least when the second plurality of survey results indicates that the subject is planning on undergoing surgery (460) The fourth plurality of filters includes a second dietary filter that is fired at least when the second plurality of survey results indicates that the subject is eating less than before receiving their last provision of the gliflozin Sodium-Glucose Cotransport 2 inhibitor pharmaceutical composition (461) The fourth plurality of filters includes a second pancreatic disease filter that is fired at least when the second plurality of survey results indicates that the subject has developed a pancreatic problem since receiving their last provision of the gliflozin Sodium-Glucose Cotransport 2 inhibitor pharmaceutical composition (462) The fourth plurality of filters includes a second alcohol consumption filter (463) The second alcohol consumption filter is fired when the second plurality of survey results indicates that the subject, on average, consumes at least a predetermined number of alcoholic drinks over a predetermined period of time (H)

*(463)* The fourth plurality of filters includes a yeast infection filter that is fired at least when the second plurality of survey results indicates that the subject has experiences symptoms of a yeast infection since receiving their last provision of the gliflozin Sodium-Glucose Cotransport 2 inhibitor pharmaceutical composition

*(464)* A yeast infection that is capable of firing the yeast infection filter is selected from the group consisting of a yeast infection of the penis, a yeast infection of the vagina, a sore throat, an increased urge to urinate, an increased volume of urine, and an increased urge to urinate at night

*(465)* The fourth plurality of filters includes a hypoglycemia symptom filter that is fired at least when the second plurality of survey results indicates that the subject has experienced symptoms of hypoglycemia since receiving their last provision of the gliflozin Sodium-Glucose Cotransport 2 inhibitor pharmaceutical composition

*(466)* A symptom of hypoglycemia that is capable of firing the hypoglycemia symptom filter is selected from the group consisting of shaking, sweating, rapid heartbeat, change in vision, increased hunger, headaches, and a change in mood

*(467)* Obtain acknowledgment from the subject for the warning issued to the subject by any filter in the fourth plurality of filters (I)

Fig. 4I

(468) Proceed with the re-fulfillment process when the re-fulfillment process is not already terminated by the firing of a filter in the third plurality of filters and the subject has acknowledged each warning associated with each filter in the fourth plurality of filters that was fired (469) The re-fulfillment process further includes storing an indication in the subject profile of a re-order for the gliflozin Sodium-Glucose Cotransport 2 inhibitor pharmaceutical composition, communicating the over the counter drug facts label for the gliflozin Sodium-Glucose Cotransport 2 inhibitor pharmaceutical composition to the subject, and authorizing, upon confirmation from the subject that the over the counter drug facts label has been received and read, a re-order provision of the gliflozin Sodium-Glucose Cotransport 2 inhibitor pharmaceutical composition to the subject (470) When the subject profile for the subject does not include a recent blood sugar status for the subject, the re-fulfillment process further includes obtaining in the second plurality of survey results a blood sugar status of the subject and including in the third plurality of filters of the first category class a second blood sugar filter that is fired at least when the second plurality of survey results indicates that the subject has a blood sugar level of at least a second baseline blood sugar level (471) The second baseline blood sugar level used in the second blood sugar filter is 7% glycated hemoglobin (472) The re-fulfillment process further includes obtaining in the second plurality of survey results a blood sugar status of the subject and including in the third plurality of filters of the first category class a second blood sugar filter that is fired at least when the second plurality of survey results indicates that the subject has a blood sugar level of at least a second baseline blood sugar level (473) The second baseline blood sugar level used in the second blood sugar filter is 7% glycated hemoglobin (474) Perform a re-fulfillment procedure where the second plurality of survey results further includes whether the subject has experienced a symptom of dehydration since receiving their last provision of the gliflozin Sodium-Glucose Cotransport 2 inhibitor pharmaceutical composition. And where the fourth plurality of filters further includes a dehydration filter that is fired at least when the second plurality of survey results indicates that the subject has experienced, since receiving their last provision of the gliflozin Sodium-Glucose Cotransport 2 inhibitor pharmaceutical composition a symptom of dehydration selected from the group consisting of dizziness, faintness, light-headedness, and weakness

(475) Perform a re-fulfillment procedure where the second plurality of survey results further includes a bladder cancer status of the subject. And where the third plurality of filters further includes a second bladder cancer filter that is fired at least when the second plurality of survey results indicates that the subject has developed bladder cancer since receiving their last provision of the gliflozin Sodium-Glucose Cotransport 2 inhibitor pharmaceutical composition (476) The gliflozin Sodium-Glucose Cotransport 2 inhibitor pharmaceutical composition is canagliflozin (477) The first plurality of survey results further includes one or more survey results selected from the group consisting of a heart failure history of the subject, an amputation history of the subject, a leg neuropathy history of the subject, a diabetic foot ulcer history of the subject, and a hyperkalemia history of the subject (478) The first plurality of filters and/or the second plurality of filters further includes one or more filters selected from the group consisting of a heart failure filter that is triggered at least when the first plurality of survey results indicates that the subject has a history of heart failure, an amputation filter that is triggered at least when the first plurality of survey results indicates that the subject has a body part amputated, a leg neuropathy filter that is triggered at least when the first plurality of survey results indicates that the subject has a leg neuropathy, a diabetic foot ulcer filter that is triggered at least when the first plurality of survey results indicates that the subject has a diabetic foot ulcer, and a hyperkalemia filter that is triggered at least when the first plurality of survey results indicates that the subject has hyperkalemia (479) The gliflozin Sodium-Glucose Cotransport 2 inhibitor pharmaceutical composition is ertugliflozin (480) The first plurality of survey results further includes one or more survey results selected from the group consisting of an amputation history of the subject, a leg neuropathy history of the subject, and a diabetic foot ulcer history of the subject (481) The first plurality of filters and/or the second plurality of filters further includes one or more filters selected from the group consisting of an amputation filter that is triggered at least when the first plurality of survey results indicates that the subject has a body part amputated, a leg neuropathy filter that is triggered at least when the first plurality of survey results indicates that the subject has a leg neuropathy, and a diabetic foot ulcer filter that is triggered at least when the first plurality of survey results indicates that the subject has a diabetic foot ulcer

Are you or do you plan to become pregnant? Are you breastfeeding or planning to breastfeed?

504

Dapagliflozin OTC should be used in pregnancy only if the potential benefits justifies the potential risk to the baby. Only a doctor can decide that. Do not breast-feed while taking Dapagliflozin OTC.

Thank you for visiting the site.

Are you taking a medication to treat diabetes? — 506

— 508

Input

HbA1c Level

Continue

Dapagliflozin OTC may not be right for you. Based on your answers, it is important to talk to your doctor about potential risks of taking Dapagliflozin OTC. It may be helpful to have your summary of answers when talking to your doctor.

Has your doctor said it is OK for you to take Dapagliflozin OTC?

[ Yes ]  [ No, View/Print Summary ]

Fig. 6

METHODS FOR LOWERING BLOOD SUGAR WITH A GLIFLOZIN SODIUM-GLUCOSE COTRANSPORT 2 INHIBITOR PHARMACEUTICAL COMPOSITION

CROSS REFERENCE TO RELATED APPLICATIONS

This application claims priority to U.S. Provisional Patent Application Ser. No. 62/685,202, filed Jun. 14, 2018, which is hereby incorporated by reference in its entirety.

TECHNICAL FIELD

The present disclosure relates generally to methods for lowering blood sugar, e.g., thereby treating Type 2 diabetes and/or maintaining sub-diabetic blood sugar levels, by administering an over-the-counter gliflozin Sodium-Glucose Cotransport 2 inhibitor pharmaceutical composition to a subject in need thereof, who has been qualified for over-the-counter access to the composition.

BACKGROUND

Diabetes is a leading cause of death and increasing health care costs worldwide. NCD Risk Factor Collaboration, The Lancet, 387:1513-1530 (2016). Since 1980, the number of people living with diabetes worldwide has nearly quadrupled. Id. As of 2015, according to the CDC, about 12% of all adults in the United States had diabetes and nearly 35% of all adults in the U.S. had prediabetes. Centers for Disease Control and Prevention, 'National Diabetes Statistics Report 2017' (2017). Further, nearly half of diabetes patients do not have their blood sugar under control. Polonsky et al., Patient Prefer. Adherence, 10:1299-1307 (2016). Moreover, diabetes poses a significant economical challenge. The American Diabetes Association estimated that in 2012, $245 billion was spent in direct and indirect medical expenses relating to diagnosed diabetes in the U.S. American Diabetes Association, Diabetes Care, 36(4):1033-46 (2013).

Fortunately, diabetes can be managed by, for example, using gliflozin Sodium-Glucose Cotransport 2 inhibitors, which are well established prescription pharmaceuticals used for lowering blood sugar, e.g., thereby treating Type 2 diabetes and/or maintaining sub-diabetic blood sugar levels. For instance, the efficacy of dapagliflozin, which was first approved in the U.S. for the treatment of diabetes in 2014, to lower blood sugar has been demonstrated in at least 14 double-blind, placebo-controlled, randomized studies. However, access to gliflozin Sodium-Glucose Cotransport 2 inhibitors is restricted by the requirement for a prescription. Unfortunately, long-term trends demonstrate many people avoid prescription medications, including gliflozin Sodium-Glucose Cotransport 2 inhibitors.

One approach to making gliflozin Sodium-Glucose Cotransport 2 inhibitors more accessible is to make then available without a prescription, e.g., over the counter ("OTC"). There are a variety of health benefits derived from switching a drug from prescription to OTC including, but not limited to, generating wider availably to therapies, providing a greater number of therapeutic approaches, providing direct and rapid access to treatments, providing patients with an active role in their own health care, and allowing patients to become self-reliant in preventing and relieving minor symptoms or conditions World Health Organization, "Guidelines for the Regulatory Assessment of Medicinal Products for use in Self-Medication," 2000. Given the large number of individuals with uncontrolled high blood sugar, providing access to OTC gliflozin Sodium-Glucose Cotransport 2 inhibitors could provide significant societal health benefits.

However, switching distribution of a pharmaceutical from prescription-only to OTC creates a significant risk that the patient population will be unable to appropriately self-select themselves for safe use of the pharmaceutical and then self-medicate using the drug in a responsible manner. The manifestations embodied within these concerns include incorrect self-diagnosis, incorrect drug-qualification, unrecognized drug-drug interactions (DDI), unanticipated adverse drug reactions and/or side-effects, improper dosing and/or administration, masking of a disease, addiction, inappropriate drug dependency, substance abuse, and patient delay in seeking necessary medical attention. Ruiz et al., Current Drug Safety, 5(4):315 (2010).

Because gliflozin Sodium-Glucose Cotransport 2 inhibitors cause adverse effects in certain patients, the population receiving the drug should be carefully selected and monitored. In order to ensure the safety of OTC distribution of gliflozin Sodium-Glucose Cotransport 2 inhibitor, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey," Oct. 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of drugs having potentially far-reaching benefits for societal health, from prescription-only to an OTC model, have repeatedly failed, in large part due to concerns over inappropriate patient selection and medication. Possibly the best documented cases relate to statins used to treat high cholesterol.

For instance, Merck has had at least three applications for sale of over the counter lovastatin rejected by the FDA, in 2000, 2005, and 2007. In 2005, their proposal to permit over the counter sales of lovastatin was rejected by an expert advisory panel at the FDA in 2005. The panel was concerned by a marketing study performed to support the proposal in which approximately one third of 3316 customers who were offered the drug over the counter decided they would purchase the drug. After reviewing the data, the panel concluded that 45% of the purchases would have been inappropriate for a variety of reasons, including the age of the subject, the subject's lack of knowledge about their condition, and contraindications associated with their condition. Dyer et al., BMJ, 330(7484):164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Non-prescription MEVACOR® 20 mg Joint Advisory Committee Meeting."

Similarly, Pfizer announced in 2011 its intention to switch LIPITOR® from prescription-only to OTC status. Sett OTC bulletin, 16 Nov. 2011, page 7. However, they abandoned their attempt in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly ⅙th of the adult population in the U.S. is eligible for cholesterol-lowering medications, under the current guidelines, but are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, what is needed in the art are systems and methods for qualifying a human subject for delivery of a gliflozin Sodium-Glucose Cotransport 2 inhibitor pharmaceutical composition over-the-counter to lower blood sugar, e.g., thereby treating Type 2 diabetes and/or maintaining sub-diabetic blood sugar levels.

The present disclosure addresses the need in the art for systems and methods configured for qualifying a human subject for over-the-counter delivery of a gliflozin Sodium-Glucose Cotransport 2 inhibitor pharmaceutical composition (e.g., dapagliflozin) in order to treat type 2 diabetes, e.g., by lowering blood sugar. In the present disclosure, systems and methods are provided for over-the-counter delivery of a gliflozin Sodium-Glucose Cotransport 2 inhibitor pharmaceutical composition to a subject. Survey results from the subject are run against a first plurality of filters. When a filter in the first plurality is fired, the subject is deemed not qualified for delivery of the gliflozin Sodium-Glucose Cotransport 2 inhibitor pharmaceutical composition. The survey results are also run against a second plurality of filters. When a respective filter in the second plurality is fired, the subject is provided with a corresponding warning. The method proceeds to a fulfillment process when no filter in the first plurality is fired and the subject has acknowledged each warning associated with each fired filter in the second plurality of filters. The fulfillment process stores the composition order, communicates a drug facts label for the gliflozin Sodium-Glucose Cotransport 2 inhibitor pharmaceutical composition to the subject, and authorizes, upon subject confirmation that the label has been read, provision of the gliflozin Sodium-Glucose Cotransport 2 inhibitor pharmaceutical composition to the subject.

Accordingly, one aspect of the present disclosure provides a method for qualifying a subject for over-the-counter delivery of a gliflozin Sodium-Glucose Cotransport 2 inhibitor pharmaceutical composition for lowering the blood sugar of the subject, e.g., thereby treating Type 2 diabetes and/or maintaining sub-diabetic blood sugar levels. The method includes conducting a first survey of the subject in order to obtain a variety of survey results. In some embodiments, the survey results indicate one or more of: whether the subject is pregnant, breastfeeding, or planning to become pregnant, a Type 1 diabetes status of the subject, a ketoacidosis status of the subject, a kidney disease status of the subject, an age of the subject, a blood sugar level of the subject, whether the subject has a liver problem, whether the subject has had a history of urinary problems, a surgery status of the subject, a dietary status of the subject, whether the subject has ever had a pancreatic problem, an alcohol consumption status of the subject, and whether the subject is taking a diabetes medication.

The method also includes running all or a portion of the survey results against a first plurality of filters of a first category class. Filters in the first category class correspond to contraindications. When a respective filter in the first plurality of filters is fired, the subject is deemed not qualified for delivery of the gliflozin Sodium-Glucose Cotransport 2 inhibitor pharmaceutical composition. The method is then terminated accordingly without delivery of the gliflozin Sodium-Glucose Cotransport 2 inhibitor pharmaceutical composition to the subject. In some embodiments, the first plurality of filters includes one or more of: a pregnancy filter, a Type 1 diabetes filter, a ketoacidosis filter, a kidney disease filter, an age filter, and a blood sugar filter.

The method also includes running all or a portion of the survey results against a second plurality of filters of a second category class. Filters in the second category class correspond to risk factors. When a respective filter in the second plurality of filters is fired, the subject is provided with a warning corresponding to the respective filter. In some embodiments, the second plurality of filters includes one or more of: a liver disease filter, a urinary problem filter, a surgery filter, a dietary filter, a pancreatic disease, an alcohol consumption filter, and a diabetes medication filter. However, unlike filters in the first plurality of filters, filters in the second plurality of filters do not automatically terminate the process without delivery of the gliflozin Sodium-Glucose Cotransport 2 inhibitor pharmaceutical composition to the subject The method continues by obtaining acknowledgment from the subject for the warning issued to the subject by any filter in the second plurality of filters. In some embodiments, acknowledgment from the subject is a written acknowledgement, a verbal acknowledgment, or an electronic acknowledgment such as an electronic signature.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the gliflozin Sodium-Glucose Cotransport 2 inhibitor pharmaceutical composition, communicating an over-the-counter drug label for the gliflozin Sodium-Glucose Cotransport 2 inhibitor pharmaceutical composition, and authorizing, upon confirmation from the subject that the over-the-counter drug label has been received and read, provision of the gliflozin Sodium-Glucose Cotransport 2 inhibitor pharmaceutical composition to the subject.

In some embodiments, the gliflozin Sodium-Glucose Cotransport 2 inhibitor pharmaceutical composition has the structure:

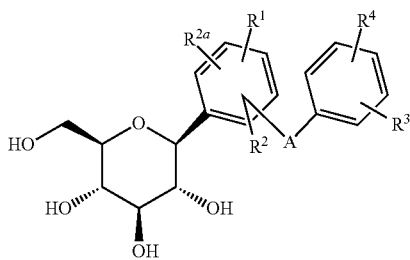

where, $R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^2$ and $R^{2a}$ together with the carbons to which they are attached can form an annelated five, six or seven membered carbocycle or heterocycle which may contain 1 to 4 heteroatoms in the ring which are N, O, S, SO, and/or $SO_2$;

$R_3$ and $R_4$ are independently hydrogen, OH, $OR^{5a}$, OAryl, $OCH_2$Aryl, alkyl, cycloalkyl, $CF_3$, $—OCHF_2$, $—OCF_3$, halogen, $—CN$, $—CO_2R^{5b}$, $—CO_2H$, $COR^{6b}$, $—CH(OH)R^{6c}$, $—CH(OR^{5h})R^{6d}$, $—CONR^6R^{6a}$, $—NHCOR^{5c}$, $—NHSO_2R^{5d}$, $—NHSO_2$Aryl, Aryl, $—SR^{5e}$, $—SOR^{5f}$, $—SO_2R^{5g}$, $—SO_2$Aryl, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$, and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$;

A is O, S, NH, or $(CH_2)_n$, where n is 0-3, or a pharmaceutically acceptable salt, stereoisomer, or prodrug ester thereof;

with the proviso that where A is $(CH_2)_n$ where n is 0, 1, 2, or 3 or A is O, and at least one of $R^1$, $R^2$, and $R^{2a}$ is OH or $OR^5$, then at least one of $R^1$, $R^2$, and $R^{2a}$ is $CF_3$, $OCF_3$, or $OCHF_2$ and/or at least one of $R^3$ and $R^4$ is $CF_3$, $—OCHF_2$, $—OCF_3$, $—CN$, $—CO_2R^{5b}$, $CH(OR^{5h})R^{6d}$, $CH(OH)R^{6c}$, $COR^{6b}$, $—NHCOR^{5c}$, $—NHSO_2R^{5d}$, $—NHSO_2$Aryl, Aryl, $—SR^{5e}$, $—SOR^{5f}$, $—SO_2R^{5g}$ or $—SO_2$Aryl.

In some embodiments, the gliflozin Sodium-Glucose Cotransport 2 inhibitor pharmaceutical composition includes dapagliflozin or a pharmaceutically acceptable salt thereof. In some embodiments, the gliflozin Sodium-Glucose Cotransport 2 inhibitor pharmaceutical composition includes dapagliflozin propanediol. In some embodiments, the gliflozin Sodium-Glucose Cotransport 2 inhibitor pharmaceutical composition includes empagliflozin, canagliflozin, or ertugliflozin.

In one aspect, the present disclosure provides a method for qualifying a subject (e.g., a subject who was previously qualified to receive a provision of the gliflozin Sodium-Glucose Cotransport 2 inhibitor pharmaceutical composition) for a re-order of the gliflozin Sodium-Glucose Cotransport 2 inhibitor pharmaceutical composition (e.g., which is optionally performed in conjunction with a method for qualifying the subject for a first order of the gliflozin Sodium-Glucose Cotransport 2 inhibitor pharmaceutical composition). The method includes a re-fulfillment procedure. The re-fulfillment procedure includes conducting a second survey of the subject in order to obtain a second plurality of survey results. In some embodiments, the second survey results indicates one or more of: whether the subject is one of pregnant, breastfeeding, or planning to become pregnant, whether the subject has developed ketoacidosis since receiving their last provision of the gliflozin Sodium-Glucose Cotransport 2 inhibitor pharmaceutical composition, whether the subject has developed a kidney problem since receiving their last provision of the gliflozin Sodium-Glucose Cotransport 2 inhibitor pharmaceutical composition, whether the subject has experienced a symptom of a urinary problem since receiving their last provision of the gliflozin Sodium-Glucose Cotransport 2 inhibitor pharmaceutical composition, whether the subject has developed a liver problem since receiving their last provision of the gliflozin Sodium-Glucose Cotransport 2 inhibitor pharmaceutical composition, a surgery status of the subject, a dietary status of the subject, whether the subject has developed a pancreatic problem since receiving their last provision of the gliflozin Sodium-Glucose Cotransport 2 inhibitor pharmaceutical composition, an alcohol consumption status of the subject, whether the subject has experienced a yeast infection since receiving their last provision of the gliflozin Sodium-Glucose Cotransport 2 inhibitor pharmaceutical composition, whether the subject has developed symptoms of hypoglycemia since receiving their last provision of the gliflozin Sodium-Glucose Cotransport 2 inhibitor pharmaceutical composition, whether the subject is experiencing a bodily stress, and whether the subject has started taking a diabetes medication since receiving their last provision of the gliflozin Sodium-Glucose Cotransport 2 inhibitor pharmaceutical composition.

The method also includes running all or a portion of the second plurality of survey results against a third plurality of filters of the first category class. Filters in the first category of filters correspond to contraindications. When a respective filter in the third plurality of filters is fired, the subject is deemed not qualified for the gliflozin Sodium-Glucose Cotransport 2 inhibitor pharmaceutical composition. Accordingly, the re-fulfillment process is terminated without delivery of the gliflozin Sodium-Glucose Cotransport 2 inhibitor pharmaceutical composition to the subject. In some embodiments, the third plurality of filters includes one or more of: a pregnancy filter, a ketoacidosis filter, a kidney problem filter, a urinary problem filter, a bodily stress filter, and a diabetes medication filter.

The method also includes running all or a portion of the second plurality of survey results against a fourth plurality of filters of the second category class. Filters in the second category of filters correspond to risk factors. When a respective filter in the fourth plurality of filters is fired the subject is provided with a warning corresponding to the respective filter. In some embodiments, the fourth plurality of filters includes one or more of: a liver disease filter, a surgery filter, a dietary filter, a pancreatic disease filter, an alcohol consumption filter, a yeast infection filter, and a hypoglycemia symptom filter.

The method continues by obtaining acknowledgment from the subject for the warning issued to the subject by any filter in the fourth plurality of filters. When the re-fulfillment process is not already terminated by the firing of a filter in the third plurality of filters and the subject has acknowledged each warning associated with each filter in the fourth plurality of filters that was fired, the method continues with a re-fulfillment procedure.

In some embodiments, the re-fulfillment procedure includes storing an indication in the subject profile of a re-order for the gliflozin Sodium-Glucose Cotransport 2 inhibitor pharmaceutical composition, communicating an over-the-counter drug facts label for the gliflozin Sodium-Glucose Cotransport 2 inhibitor pharmaceutical composition to the subject, and authorizing, upon confirmation from the subject that the over-the-counter drug facts label has been received and read, a re-order provision of the gliflozin Sodium-Glucose Cotransport 2 inhibitor pharmaceutical composition to the subject.

In some embodiments, when the subject profile for the subject does not include a recent blood sugar status for the subject, the method includes obtaining, in the second plurality of survey results, a blood sugar status of the subject and including, in the third plurality of filters of the first category class, a blood sugar filter.

In some embodiments, the method includes obtaining, in the second plurality of survey results, a blood sugar status of the subject and including, in the third plurality of filters of the first category class, a blood sugar filter.

In some embodiments, e.g., when the gliflozin Sodium-Glucose Cotransport 2 inhibitor pharmaceutical composition includes canagliflozin, the first plurality of survey results further includes one or more of: a heart failure history of the subject, an amputation history of the subject, a leg neuropathy history of the subject, a diabetic foot ulcer history of the subject, and a hyperkalemia history of the subject. Accordingly, the second plurality of filters includes one or more filters corresponding to the additional survey results, e.g., selected from a heart failure filter, an amputation, a leg neuropathy filter, a diabetic foot ulcer filter that is triggered at least when the first plurality of survey results indicates that the subject has, and a hyperkalemia filter.

In some embodiments, e.g., when the gliflozin Sodium-Glucose Cotransport 2 inhibitor pharmaceutical composition includes ertugliflozin, the first plurality of survey results further includes one or more of: an amputation history of the subject, a leg neuropathy history of the subject, and a diabetic foot ulcer history of the subject. Accordingly, the second plurality of filters includes one or more filters corresponding to the additional survey results, e.g., selected from an amputation filter, a leg neuropathy filter, and a diabetic foot ulcer filter.

In some embodiments, e.g., when the gliflozin Sodium-Glucose Cotransport 2 inhibitor pharmaceutical composition includes dapagliflozin, the first plurality of survey results further includes whether the subject has ever had bladder cancer, and the first plurality of filters includes a first bladder cancer filter.

In some embodiments, the warning corresponding to a respective filter in the second plurality of filters includes a prompt for the subject to indicate whether they have discussed the risk factor underlying the respective filter in the second plurality of filters that was fired with a health care professional. The method further includes that acknowledgement is obtained from the subject when the subject indicates that they have discussed the risk factor underlying the respective filter in the second plurality of filters that was fired with a health care professional.

In some embodiments, e.g., when the gliflozin Sodium-Glucose Cotransport 2 inhibitor pharmaceutical composition includes dapagliflozin, the second plurality of survey results further includes a bladder cancer status of the subject, and the third plurality of filters further includes a bladder cancer filter.

BRIEF DESCRIPTION OF THE DRAWINGS

FIGS. 4A, 4B, 4C, 4D, 4E, 4F, 4G, 4H, 4I, 4J, and 4K collectively provide a flow chart of processes for qualifying a human subject for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels, where elements in dashed boxes are optional, in accordance with various embodiments of the present disclosure.

FIG. 6 illustrates feedback from a first survey, in accordance with an embodiment of the present disclosure.

Figure 1:
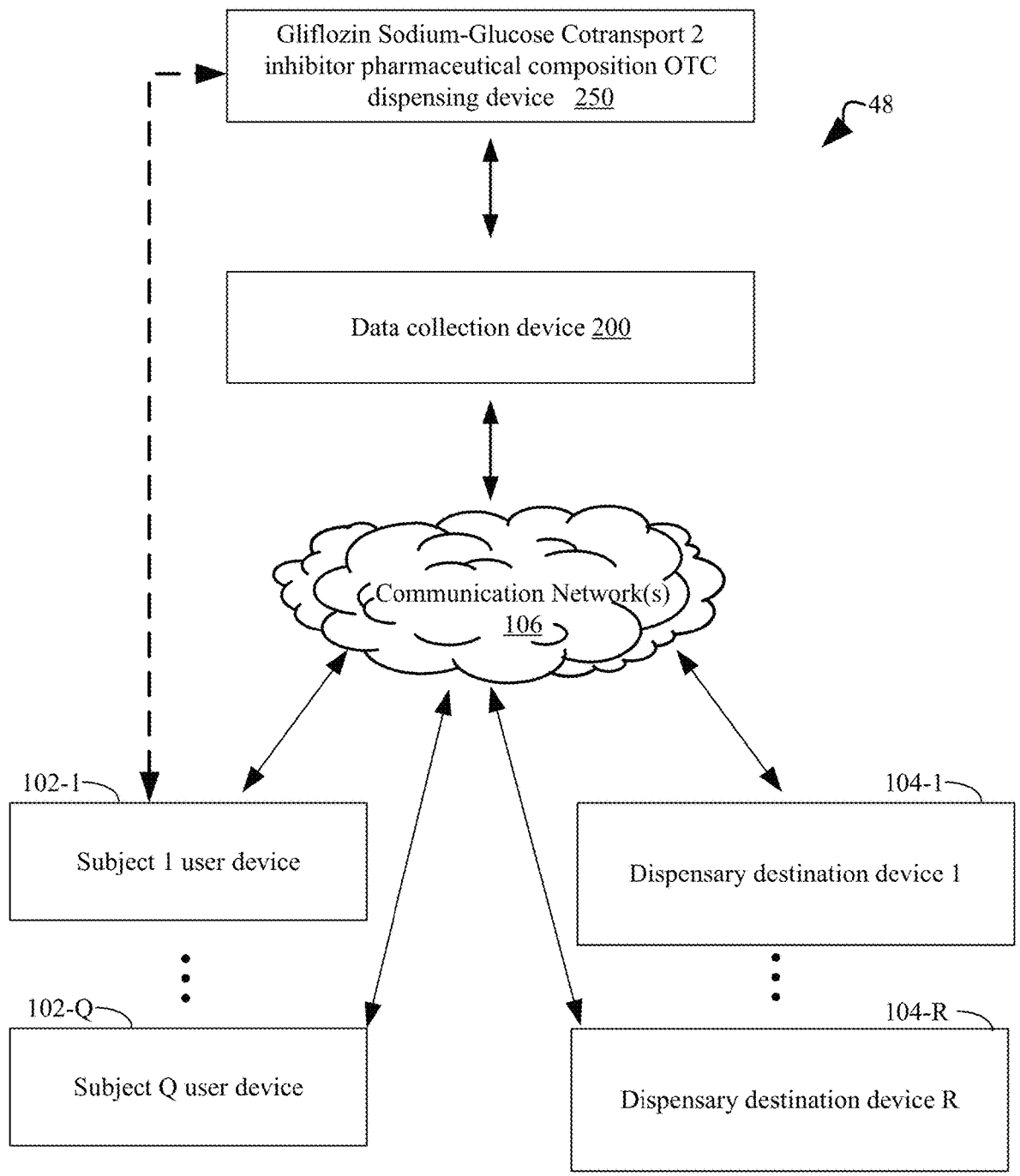
FIG. 1 illustrates an exemplary system topology that includes a gliflozin Sodium-Glucose Cotransport 2 inhibitor pharmaceutical composition over-the-counter (OTC) dispensing device for qualifying a human subject for over-the-counter delivery of a gliflozin Sodium-Glucose Cotransport 2 inhibitor pharmaceutical composition for lowering blood sugar e.g., thereby treating Type 2 diabetes and/or maintaining sub-diabetic blood sugar levels, a data collection device for collecting subject data, one or more user devices associated with human subjects, and one or more dispensary destination devices for distributing the gliflozin Sodium-Glucose Cotransport 2 inhibitor pharmaceutical composition over-the-counter, where the above-identified components are interconnected, optionally through a communications network, in accordance with an embodiment of the present disclosure.

In the figures, reference numbers refer to the same or equivalent parts of the present invention throughout the several figures of the drawing.

DETAILED DESCRIPTION

Diabetes is a growing health problem, in the United States and worldwide. Although diabetes can be effectively treated using established pharmaceutical compositions, access to these drugs is hindered by to the requirement for a prescription, as many individuals do not have adequate access and/or avoid the healthcare system for a variety of reasons. Accordingly, many people are not managing their diabetes conditions appropriately. While over-the-counter alternatives to these prescription pharmaceuticals would increase access to these compositions, thereby improving population management of diabetes around the world, patients often have difficulty self-selecting themselves for an appropriate over-the-counter medication. Because inappropriate use of these drugs can result in ineffective treatment and/or serious side-effects, better methods for selecting for, and treating patients with, other-the-counter diabetes medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include capsules, tablets, liquids, topical formulations, and inhaled formulations.

As used herein, the term "contraindication" refers to a condition that makes a treatment, e.g., over-the-counter use of a gliflozin Sodium-Glucose Cotransport 2 inhibitor pharmaceutical composition, inadvisable. Contraindications include physical characteristics of a subject, e.g., pregnancy or kidney disease, and contemporaneous drug use, e.g., gliflozin Sodium-Glucose Cotransport 2 inhibitor pharmaceutical composition use. In the present context, identification of a contraindication fires a filter of a first category class, which prevents authorizing provision of a gliflozin Sodium-Glucose Cotransport 2 inhibitor pharmaceutical composition, in accordance with some implementations of the methods, systems, and software disclosed herein.

As used herein, the term "risk factor" refers to a condition that makes a treatment, e.g., over-the-counter use of a gliflozin Sodium-Glucose Cotransport 2 inhibitor pharmaceutical composition, possibly inadvisable. Risk factors include physical characteristics of a subject, e.g., a blood sugar reading, and contemporaneous drug use, e.g., use of a diabetes medication. In the present context, identification of a risk factor fires a filter of a second category class, which prevents authorizing provision of a gliflozin Sodium-Glucose Cotransport 2 inhibitor pharmaceutical composition without confirmation that the subject has discussed the risk factor with a medical professional, in accordance with some implementations of the methods, systems, and software disclosed herein.

As used herein, "drug interactions," e.g., with a gliflozin Sodium-Glucose Cotransport 2 inhibitor, include pharmacokinetic drug interactions and pharmacodynamics drug interactions. Generally, a pharmacokinetic drug interaction is an interaction between two drugs (e.g., a gliflozin Sodium-Glucose Cotransport 2 inhibitor and a second drug) that result in alterations in the absorption, transport, distribution, metabolism, and/or excretion of either drug. Generally, a pharmacokinetic drug interaction is an interaction between two drugs (e.g., a gliflozin Sodium-Glucose Cotransport 2 inhibitor and a second drug) that result in a direct change in the effect or either drug. For a more comprehensive summary of pharmacokinetic drug interactions and pharmacodynamics drug interactions, see, Cascorbi, I, Dtsch Arztebl Int., 109(33-34):546-55 (2012), the content of which is hereby incorporated by reference.

In the context of the present disclosure, classification of a condition as either a contraindication or a risk factor is specific to a particular identity and dose of a gliflozin Sodium-Glucose Cotransport 2 inhibitor pharmaceutical composition being authorized for over-the-counter use. Classification of a particular condition, e.g., contemporaneous gliflozin Sodium-Glucose Cotransport 2 inhibitor pharmaceutical composition use, may vary between different gliflozin Sodium-Glucose Cotransport 2 inhibitor pharmaceutical compositions (e.g., it may be classified as a contraindication for a first gliflozin Sodium-Glucose Cotransport 2 inhibitor, a risk factor for a second gliflozin Sodium-Glucose Cotransport 2 inhibitor, and/or neither for a third gliflozin Sodium-Glucose Cotransport 2 inhibitor). Likewise, a particular condition may be classified as a contraindication for use of a particular gliflozin Sodium-Glucose Cotransport 2 inhibitor at a first over-the-counter dosage, classified as a risk factor for the same particular gliflozin Sodium-Glucose Cotransport 2 inhibitor at a second (e.g., lower) over-the-counter dosage, and/or classified as neither for the same particular gliflozin Sodium-Glucose Cotransport 2 inhibitor at a third (e.g., lowest) over-the-counter dosage.

As used herein, whether a subject "has developed" a condition since receiving their last provision of a gliflozin Sodium-Glucose Cotransport 2 inhibitor refers to both conditions that are new to the subject, i.e., a condition that the subject did not have at the time they received their last provision of the gliflozin Sodium-Glucose Cotransport 2 inhibitor, and conditions that have been newly diagnosed, regardless of whether the condition existed when the subject received their last provision of the gliflozin Sodium-Glucose Cotransport 2 inhibitor, i.e., a condition that the subject was not aware of when they received their last provision of the gliflozin Sodium-Glucose Cotransport 2 inhibitor.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (e.g. $C_1$-$C_{10}$ means one to ten carbons). Examples of saturated hydrocarbon radicals include, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$) alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy) propyl, and the like).

Each of the above terms (e.g., "alkyl," "heteroalkyl," "aryl, and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', —NR'R", —SR', halogen, —SiR'R"R''', —OC(O)R', —C(O)R', —CONR'R", —OC(O)NR'R", —NR"C(O)R', —NR'—C(O)NR"R''', —NR"C(O)$_2$R', —NR—C(NR'R"R''')=NR"", NR C(NR'R")=NR''', —S(O)R', —S(O)$_2$R', —S(O)$_2$NR'R", NRSO$_2$R', —CN and —NO$_2$ in a number ranging from zero to (2m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents," which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', NR' C(O)NR"R''', —NR"C(O)$_2$R', NR—C(NR'R"R''')=NR"", NR C(NR'R")=NR''', —S(O)R", —S(O)$_2$R', —S(O)2NR'R", NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system. Each of the above-named groups is attached to the heteroarene or heteroaryl nucleus directly or through a heteroatom (e.g., P, N, O, S, Si, or B); and where R', R", R''' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

As used herein, the term "heteroatom" includes oxygen (O), nitrogen (N), sulfur (S) and silicon (Si), boron (B) and phosphorous (P).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

In one aspect of the present disclosure a survey of a subject is conducted to obtain survey results, in order to determine if the subject qualifies for an over-the-counter (OTC) gliflozin Sodium-Glucose Cotransport 2 inhibitor pharmaceutical composition for lowering blood sugar, e.g., thereby, treating Type 2 diabetes and/or maintaining sub-diabetic blood sugar levels. The survey results are used as the basis for running filters of a first category class. If the triggering conditions of any of the filters in the first category class are fired, the subject does not qualify for the OTC gliflozin Sodium-Glucose Cotransport 2 inhibitor pharmaceutical composition. The survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired a fulfillment process is initiated for OTC delivery of the gliflozin Sodium-Glucose Cotransport 2 inhibitor pharmaceutical composition.

FIG. 1 illustrates an example of an integrated system 48 for conducting one or more surveys of subjects in order to qualifying the subjects for OTC delivery of a gliflozin Sodium-Glucose Cotransport 2 inhibitor pharmaceutical composition. The integrated system 48 includes one or more connected user devices 102. The user devices 102 are configured for entering survey data and making requests for the gliflozin Sodium-Glucose Cotransport 2 inhibitor pharmaceutical composition. The system 48 also includes one or more dispensary destination devices 104 that are configured to receive instructions in order to provide the gliflozin Sodium-Glucose Cotransport 2 inhibitor pharmaceutical composition to qualifying subjects. Furthermore, the system 48 includes a gliflozin Sodium-Glucose Cotransport 2 inhibitor pharmaceutical composition over-the-counter (OTC) dispensing device 250 and one or more data collection devices 200 that are configured for collecting subject data.

Throughout the present disclosure, the data collection device 200 and the gliflozin Sodium-Glucose Cotransport 2 inhibitor pharmaceutical composition OTC dispensing device 250 will be referenced as separate devices solely for purposes of clarity. That is, the disclosed functionality of the data collection device 200 and the disclosed functionality of the gliflozin Sodium-Glucose Cotransport 2 inhibitor pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the gliflozin Sodium-Glucose Cotransport 2 inhibitor pharmaceutical composition OTC dispensing device 250 are contained in a single device.

With the integrated system 48, survey results from the subjects are run against a first plurality of filters (e.g., filter 216-1, filter 216-2, filter 216-4, etc.) When a filter in the first plurality of filters (e.g., filter 216) is fired for a respective subject, the respective subject is deemed not qualified for the gliflozin Sodium-Glucose Cotransport 2 inhibitor pharmaceutical composition. The survey results are also run against a second plurality of filters (e.g., filter 222-1, filter 222-2, filter 222-6, etc.) When a respective filter in the second plurality is fired for a respective subject, the respective subject is provided with a warning (e.g., filter warning 226) associated with the respective filter. In some embodiments the survey results are run against the first plurality of filters and the second plurality of filters concurrently. In some embodiments the survey results are run against the first plurality of filters and then against the second plurality of filters. The method enabled by the integrated system 48 proceeds to a fulfillment process when no filter in the first plurality fires and the subject has acknowledged, or otherwise successfully addressed, each warning associated with each filter in the second plurality of filters that fired. As part of the fulfillment process, the composition order is stored (e.g., in a subject profile 232 associated with the subject to receive the drug), a drug facts label (e.g., over the counter drug facts label 230) for the gliflozin Sodium-Glucose Cotransport 2 inhibitor is communicated to the qualifying subject. Upon subject confirmation that the label has been read, authorization is granted to dispense the gliflozin Sodium-Glucose Cotransport 2 inhibitor.

Referring to FIG. 1, the gliflozin Sodium-Glucose Cotransport 2 inhibitor pharmaceutical composition OTC dispensing device 250 qualifies a subject for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels. To accomplish this, the data collection device 200, which is in electrical communication with the gliflozin Sodium-Glucose Cotransport 2 inhibitor pharmaceutical composition OTC dispensing device 250, receives survey results originating from one or more user devices 102 associated with corresponding subjects. In some embodiments, the data collection device 200 receives such survey results directly from the user devices 102. For instance, in some embodiments the data collection device 200 receives this data wirelessly through radio-frequency signals. In some embodiments, such signals are in accordance with an 802.11 (Wi-Fi), Bluetooth, or ZigBee standard. In some embodiments, the data collection device 200 receives such data directly, analyzes the data, and passes the analyzed data to the gliflozin Sodium-Glucose Cotransport 2 inhibitor pharmaceutical composition OTC dispensing device 250.

In some embodiments, the data collection device 200 and/or the gliflozin Sodium-Glucose Cotransport 2 inhibitor pharmaceutical composition OTC dispensing device 250 is not proximate to the subject and/or does not have wireless capabilities or such wireless capabilities are not used for the purpose of acquiring survey results. In such embodiments, a communication network 106 may be used to survey questions (e.g., survey questions 208, 212) from the gliflozin Sodium-Glucose Cotransport 2 inhibitor pharmaceutical composition OTC dispensing device 250 to user devices 102 and the answers to such survey questions from the user devices 102 to the data collection device 200 and/or the gliflozin Sodium-Glucose Cotransport 2 inhibitor pharmaceutical composition OTC dispensing device 250. Further, in some embodiments the communication network 106 is used to communicate authorization to dispense the gliflozin Sodium-Glucose Cotransport 2 inhibitor survey questions from the gliflozin Sodium-Glucose Cotransport 2 inhibitor pharmaceutical composition OTC dispensing device 250 to dispensary destination devices 104.

Examples of networks 106 include, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the gliflozin Sodium-Glucose Cotransport 2 inhibitor pharmaceutical composition OTC dispensing device 250. Further, the data collection device 200 and/or the gliflozin Sodium-Glucose Cotransport 2 inhibitor pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
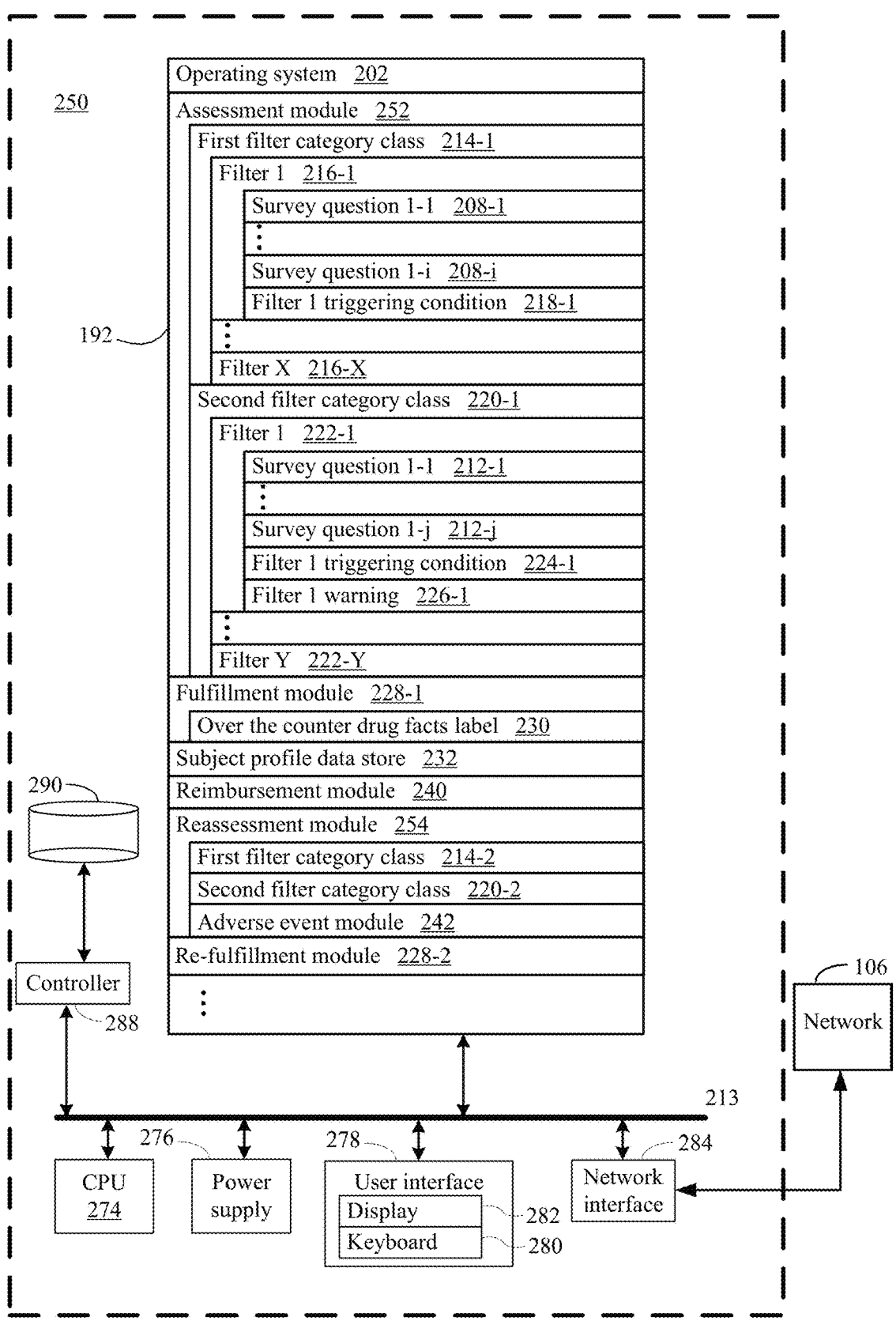
FIG. 2 illustrates an example device for qualifying a human subject for delivery of a gliflozin Sodium-Glucose Cotransport 2 inhibitor pharmaceutical composition over-the-counter for lowering blood sugar, e.g., thereby treating Type 2 diabetes and/or maintaining sub-diabetic blood sugar levels, in accordance with various embodiments of the present disclosure.

Turning to FIG. 2 with the foregoing in mind, an exemplary gliflozin Sodium-Glucose Cotransport 2 inhibitor pharmaceutical composition OTC dispensing device 250 configured for determining whether a subject is qualified for OTC delivery of a gliflozin Sodium-Glucose Cotransport 2 inhibitor is depicted. Referring to FIG. 2, in typical embodiments, the gliflozin Sodium-Glucose Cotransport 2 inhibitor pharmaceutical composition OTC dispensing device 250 includes one or more computers. For purposes of illustration in FIG. 2, the gliflozin Sodium-Glucose Cotransport 2 inhibitor pharmaceutical composition OTC dispensing device 250 is represented as a single computer that includes all of the functionality for qualifying a human subject for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels. However, the present disclosure is not limited thereto. In some embodiments, the functionality for qualifying a human subject for over-the-counter delivery of a gliflozin Sodium-Glucose Cotransport 2 inhibitor pharmaceutical composition for lowering blood sugar (e.g., thereby treating Type 2 diabetes and/or maintaining sub-diabetic blood sugar levels) is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the application and all such topologies are within the scope of the present disclosure.

The gliflozin Sodium-Glucose Cotransport 2 inhibitor pharmaceutical composition OTC dispensing device 250 of FIG. 2 is configured to conduct a first survey (e.g., using assessment module 252 to perform an initial qualification of the subject for provision of a gliflozin Sodium-Glucose Cotransport 2 inhibitor pharmaceutical composition) and/or a second survey (e.g., using reassessment module 254 to perform a re-qualification of the subject for provision of a gliflozin Sodium-Glucose Cotransport 2 inhibitor pharmaceutical composition). The first survey (e.g., the assessment) includes a variety of survey questions 208-1, 212-1 associated with filters 216, 222 within a plurality of filters of the first filter category class 214-1 and a plurality of filters in the second filter category class 220-1, respectively. Answers to the questions in the first survey received by the device are run against filters of a first category class 214-1, and filters of a second category class 220-1 within the first and second pluralities of filters 214-1, 216-1, respectively. Similarly, the second survey (e.g., the re-assessment) also includes a variety of questions associated with filters 216, 222 within a plurality of filters of a first category class 214-2 and a plurality of filters of a second category class 220-2, respectively. Answers to the questions in the second survey received by the device are run against filters of a first category class 216-2 and filters of a second category class 220-2, e.g., within the first and second pluralities of filters, respectively. Filters 216 of the first filter category class 214 are configured to terminate the qualification process when fired. Filters 222 of the second filter category class 220 are configured to provide the subject with a warning associated with a corresponding survey question. In other words, the device of FIG. 2 is configured to accumulate results from a survey (e.g., survey questions 208 and survey questions 212) and run the results against corresponding filters (e.g., filters 216 and filters 222, respectively) in order to determine if a subject is qualified for OTC delivery of a gliflozin Sodium-Glucose Cotransport 2 inhibitor pharmaceutical composition.

In the present disclosure, a plurality of filters refers to a series, or set, or filters in either the first filter category class or the second category class. For instance, in some embodiments, a plurality of filters of the first filter category class 214 can comprise any subset of filters 216 of the first filter category class. As an example, in some embodiments a plurality of filters of the first category class includes filters 216-1, 216-2, 216-3, . . . , 216-i, or any combination thereof. Similarly, a plurality of filters of the second filter category class 220 can comprise any set of filters 222 of the second filter category class. Moreover, in some embodiments a plurality of filters of the second category class includes filters 222-1, 222-2, 222-3, . . . , 222-i, or any combination thereof.

Continuing to refer to FIG. 2, in some embodiments, the dispensing device 250 includes one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the gliflozin Sodium-Glucose Cotransport 2 inhibitor pharmaceutical composition OTC dispensing device 250 but that can be electronically accessed by the gliflozin Sodium-Glucose Cotransport 2 inhibitor pharmaceutical composition OTC dispensing device 250 over an Internet, intranet, or other form of network or electronic cable (illustrated as element 106 in FIG. 2) using network interface 284.

In some embodiments, the memory 192 of the gliflozin Sodium-Glucose Cotransport 2 inhibitor pharmaceutical composition OTC dispensing device 250 stores one or more of:

an operating system 202 that includes procedures for handling various basic system services;

an assessment module 252 for qualifying a subject for an initial over-the-counter delivery of a gliflozin Sodium-Glucose Cotransport 2 inhibitor pharmaceutical composition for lowering blood sugar e.g., thereby treating Type 2 diabetes and/or maintaining sub-diabetic blood sugar levels, by communicating survey questions, obtaining results therefrom, and applying the results to qualifying filters, the assessment module including:

a first filter category class 214-1, including filters 216 (e.g., a first plurality of filters), each respective filter 216 in the first filter category class 214-1 associated with one or more survey questions 208 and one or more triggering conditions 218;

a second filter category class 220-1, including filters 222 (e.g., a second plurality of filters), each respective filter 222 in the second filter category class 220-1 associated with one or more survey questions 212, triggering conditions 224, and warnings 226;

a fulfillment module 228-1 for executing a fulfillment process when no filter 216 in the first filter category class 214-1 has been fired for a subject and the subject has acknowledged each warning 226 associated with each filter 222 in the second filter category class 220-1 that was fired as a result of answers by the subject to the survey questions 212, where the fulfillment process includes communicating an over-the-counter drug facts label 230 for the gliflozin Sodium-Glucose Cotransport 2 inhibitor pharmaceutical composition to the subject and receiving confirmation from the subject that the over-the-counter drug facts label has been received and read;

a reassessment module 254 for qualifying a subject for a subsequent over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels, by communicating survey questions, obtaining results therefrom, and applying the results to qualifying filters, the assessment module including:

a first filter category class 214-2, including filters 216 (e.g., a third plurality of filters), each respective filter 216 in the first filter category class 214-2 associated with one or more survey questions 208 and one or more triggering conditions 218;

a second filter category class 220-2, including filters 222 (e.g., a second plurality of filters), each respective filter 222 in the second filter category class 220-2 associated with one or more survey questions 212, triggering conditions 224, and warnings 226;

a re-fulfillment module 228-2 for executing a re-fulfillment process when no filter 216 in the first filter category class 214-2 has been fired for a subject and the subject has acknowledged each warning 226 associated with each filter 222 in the second filter category class 220-2 that was fired as a result of answers by the subject to the survey questions 212, where the fulfillment process includes communicating an over-the-counter drug facts label 230 for the gliflozin Sodium-Glucose Cotransport 2 inhibitor pharmaceutical composition to the subject and receiving confirmation from the subject that the over-the-counter drug facts label has been received and read;

a subject profile data store 232 comprising a subject profile 232 for each of a plurality of subjects, each respective subject profile 232 including information (e.g., shipping information, billing information, biometric information, etc.) about a corresponding subject in the plurality of subjects, an initial order date and destination 236, and any re-order date and the destination 238 for the gliflozin Sodium-Glucose Cotransport 2 inhibitor pharmaceutical composition made by the corresponding subject using the gliflozin Sodium-Glucose Cotransport 2 inhibitor pharmaceutical composition OTC dispensing device 250;

an adverse event module 242 for identifying and aggregating records of adverse events associated with a plurality of subjects, e.g., corresponding to the firing of a filter 216 in the first filter category class 214-2 during a re-fulfillment process;

a reimbursement module 240 for determining eligibility and/or communicating an insurance claim associated with delivery of the gliflozin Sodium-Glucose Cotransport 2 inhibitor, e.g., based on insurance information stored in a respective subject profile 232.

In some embodiments, the assessment module 252, reassessment module 254, and/or fulfillment module 228 are accessible within any browser (e.g., phone, tablet, laptop/desktop, or smartwatch). In some embodiments the assessment module 252, reassessment module 254, and/or fulfillment module 228 run on native device frameworks, and are available for download onto a user device 102 running an operating system 202 such as Android, iOS, or WINDOWS.

In some implementations, one or more of the above identified data elements or modules (e.g., assessment module 252, fulfillment module 228-1, etc.) of the gliflozin Sodium-Glucose Cotransport 2 inhibitor pharmaceutical composition OTC dispensing device 250 for qualifying a human subject for over-the-counter delivery of a gliflozin Sodium-Glucose Cotransport 2 inhibitor pharmaceutical composition for lowering blood sugar (e.g., thereby treating Type 2 diabetes and/or maintaining sub-diabetic blood sugar levels) are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a gliflozin Sodium-Glucose Cotransport 2 inhibitor pharmaceutical composition OTC dispensing device 250 for qualifying a human subject for over-the-counter delivery of a gliflozin Sodium-Glucose Cotransport 2 inhibitor pharmaceutical composition for lowering blood sugar (e.g., thereby treating Type 2 diabetes and/or maintaining sub-diabetic blood sugar levels) is a smart phone (e.g., an iPhone, Blackberry, etc.), a laptop, a tablet computer, a desktop computer, a smart watch, or another form of electronic device (e.g., a gaming console). In some embodiments, the gliflozin Sodium-Glucose Cotransport 2 inhibitor pharmaceutical composition OTC dispensing device 250 is not mobile. In some embodiments, the gliflozin Sodium-Glucose Cotransport 2 inhibitor pharmaceutical composition OTC dispensing device 250 is mobile.

In some embodiments, the gliflozin Sodium-Glucose Cotransport 2 inhibitor pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the gliflozin Sodium-Glucose Cotransport 2 inhibitor pharmaceutical composition OTC dispensing device 250 are shown in FIG. 2 in order to better emphasize the additional software modules that are installed on the gliflozin Sodium-Glucose Cotransport 2 inhibitor pharmaceutical composition OTC dispensing device 250.

Figure 3:
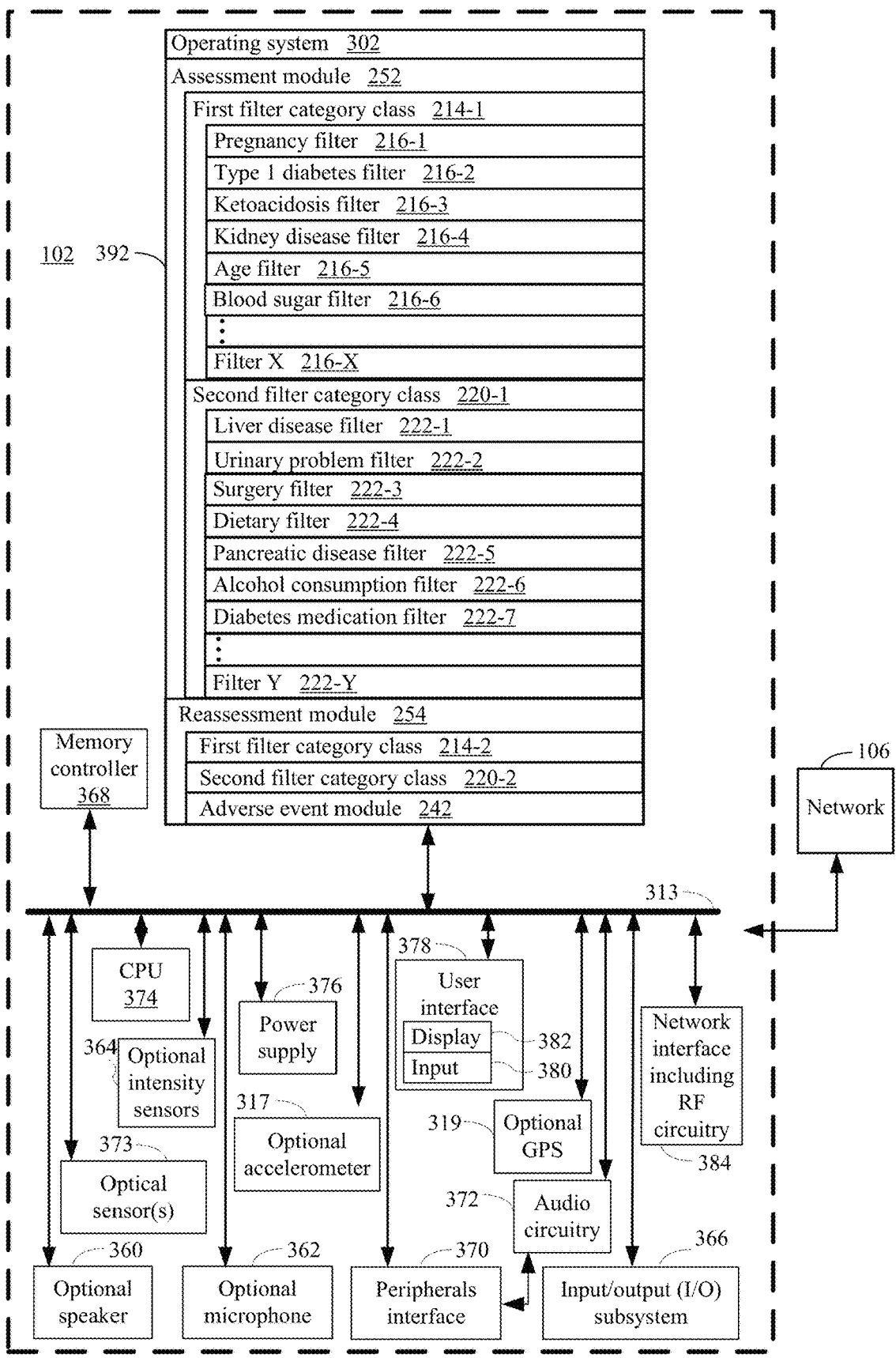
FIG. 3 illustrates an example device associated with a human subject for qualifying the human subject for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels, in accordance with an embodiment of the present disclosure, where it will be appreciated that the example device of FIG. 3 works in conjunction with the device of FIG. 2 to perform the methods illustrated in FIGS. 4 through 8 in some embodiments by, for instance providing the device of FIG. 2 with survey results and/or the results of firing filters of the present disclosure against such survey results but that, in alternative embodiments, the device of FIG. 2 performs all the methods of the present disclosure and the device of FIG. 3 is not used. In still further alternative embodiments, the device of FIG. 3 performs the methods of the present disclosure and the device of FIG. 2 is not used.

FIG. 3 provides a description of a user device 102 that can be used with the present disclosure. The user device 102 illustrated in FIG. 3 has one or more processing units (CPU's) 374, peripherals interface 370, memory controller 368, a network or other communications interface 384, a memory 392 (e.g., random access memory), a user interface 378, the user interface 378 including a display 382 and input 380 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey (e.g., first survey 206) in order to qualify for over-the-counter delivery of a gliflozin Sodium-Glucose Cotransport 2 inhibitor pharmaceutical composition for lowering blood sugar (e.g., thereby treating Type 2 diabetes and/or maintaining sub-diabetic blood sugar levels), and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 392 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 392 by other components of the gliflozin Sodium-Glucose Cotransport 2 inhibitor pharmaceutical composition OTC dispensing device 250, such as CPU(s) 374 is, optionally, controlled by the memory controller 368. In some embodiments, the memory 392 of the user device 102 illustrated in FIG. 3 optionally includes:

- an operating system 302 that includes procedures for handling various basic system services;
- the assessment module 252 described above in conjunction with the gliflozin Sodium-Glucose Cotransport 2 inhibitor pharmaceutical composition OTC dispensing device 250;
- the first category class 214 described above in conjunction with the gliflozin Sodium-Glucose Cotransport 2 inhibitor pharmaceutical composition OTC dispensing device 250 further comprising a first pregnancy filter 216-1, a Type 1 diabetes filter 216-2, a ketoacidosis filter 216-3, a first kidney disease filter 216-4, an age filter 216-5, and a first blood sugar filter 216-6; and
- the second category class 220 described above in conjunction with the gliflozin Sodium-Glucose Cotransport 2 inhibitor pharmaceutical composition OTC dispensing device 250 comprising a first liver disease filter 222-1, a first urinary problem filter 222-2, a surgery filter 222-3, a first dietary filter 222-4, a first pancreatic disease 222-5, an alcohol consumption filter 222-6, and a first diabetes medication filter 222-7;

In some embodiments, the optional accelerometer 317, optional GPS 319, and/or magnetometer (not shown) of the user device 102 or such components are used to recommend to qualifying subjects one or more suitable destinations for delivery of the gliflozin Sodium-Glucose Cotransport 2 inhibitor pharmaceutical composition over-the-counter. In some embodiments, the GPS 319 is used to determine if a subject is geographically restricted for OTC delivery of the gliflozin Sodium-Glucose Cotransport 2 inhibitor pharmaceutical composition. Geographical restrictions include a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are, optionally, implemented on a single chip. In some other embodiments, they are implemented on separate chips.

RF (radio frequency) circuitry of network interface 384 receives and sends RF signals, also called electromagnetic signals. In some embodiments, the survey module 204, survey questions 208/212, answers to survey questions 208/212, and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the gliflozin Sodium-Glucose Cotransport 2 inhibitor pharmaceutical composition OTC dispensing device 250 via the electromagnetic signals. The RF circuitry 384 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 360 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels, to help diagnose a subject's condition remotely, or to acquire visual physiological measurements of the subject, etc.).

As illustrated in FIG. 3, the user device 102 preferably includes an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with electronic medical record systems to exchange information in any way.

Now that details of a system 48 for qualifying a human subject for over-the-counter delivery of a gliflozin Sodium-Glucose Cotransport 2 inhibitor pharmaceutical composition for lowering blood sugar (e.g., thereby treating Type 2 diabetes and/or maintaining sub-diabetic blood sugar levels) have been disclosed, details regarding a method (400), including processes and features to be performed by the system, in accordance with an embodiment of the present disclosure, are disclosed with reference to FIGS. 4A through 4K. In some embodiments, such processes and features of the system are carried out by the assessment module 252, reassessment module 254, fulfillment module 228-1, and/or re-fulfillment module 228-2 illustrated in FIGS. 2 and 3. In some embodiments, the assessment module 252, reassessment module 254, fulfillment module 228-1, and/or re-fulfillment module 228-1 are a single software module. In the flow chart, elements in dashed boxes are considered to be optional.

Blocks 402-407.

Referring to block 402 of FIG. 4A, a goal of the present disclosure is to qualify subjects for over-the-counter delivery of a gliflozin Sodium-Glucose Cotransport 2 inhibitor pharmaceutical composition for lowering blood sugar, e.g., thereby, treating type 2 diabetes, using a computer system such as a gliflozin Sodium-Glucose Cotransport 2 inhibitor pharmaceutical composition OTC dispensing device 250. The gliflozin Sodium-Glucose Cotransport 2 inhibitor pharmaceutical composition OTC dispensing device (e.g., device 250) includes one or more processors (e.g., processor 274) and a memory (e.g., memory 192). The memory stores non-transitory instructions that, when executed by the one or more processors, perform a method.

Referring to block 403, in some embodiments the gliflozin Sodium-Glucose Cotransport 2 inhibitor pharmaceutical composition the gliflozin Sodium-Glucose Cotransport 2 inhibitor pharmaceutical composition has a structure of structure (I):

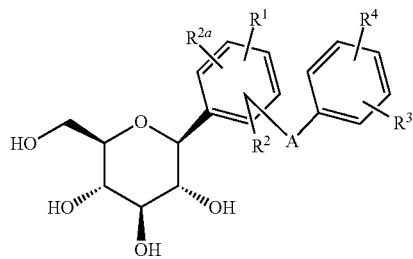

where:

$R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five, six or seven membered carbocycle or heterocycle which may contain 1 to 4 heteroatoms in the ring which are N, O, S, SO, and/or $SO_2$;

$R_3$ and $R_4$ are independently hydrogen, OH, $OR^{5a}$, OAryl, $OCH_2$Aryl, alkyl, cycloalkyl, $CF_3$, —$OCHF_2$, —$OCF_3$, halogen, —CN, —$CO_2R^{5b}$, —$CO_2H$, $COR^{6b}$, —CH(OH) $R^{6c}$, —CH($OR^{5h}$)$R^{6d}$, —$CONR^6R^{6a}$, —$NHCOR^{5c}$, —$NHSO_2R^{5d}$, —$NHSO_2$Aryl, Aryl, —$SR^{5e}$, —$SOR^{5f}$, —$SO_2R^{5g}$, —$SO_2$Aryl, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$, and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$;

A is O, S, NH, or $(CH_2)_n$, where n is 0-3, or a pharmaceutically acceptable salt, stereoisomer, or prodrug ester thereof;

with the proviso that where A is $(CH_2)_n$ where n is 0, 1, 2, or 3 or A is O, and at least one of $R^1$, $R^2$, and $R^{2a}$ is OH or $OR^5$, then at least one of $R^1$, $R^2$, and $R^{2a}$ is $CF_3$, $OCF_3$, or $OCHF_2$ and/or at least one of $R^3$ and $R^4$ is $CF_3$, —$OCHF_2$, —$OCF_3$, —CN, —$CO_2R^{5b}$, $CH(OR^{5h})R^{6d}$, $CH(OH)R^{6c}$, $COR^{6b}$, —$NHCOR^{5c}$, —$NHSO_2R^{5d}$, —$NHSO_2$Aryl, Aryl, —$SR^{5e}$, —$SOR^{5f}$, —$SO_2R^{5g}$ or —$SO_2$Aryl.

Referring to blocks 404-406, in some embodiments the gliflozin Sodium-Glucose Cotransport 2 inhibitor pharmaceutical composition includes dapagliflozin. In some embodiments, the gliflozin Sodium-Glucose Cotransport 2 inhibitor is a pharmaceutically acceptable salt of dapagliflozin. In some embodiments, the gliflozin Sodium-Glucose Cotransport 2 inhibitor pharmaceutical composition includes dapagliflozin propanediol.

In some embodiments, the gliflozin Sodium-Glucose Cotransport 2 inhibitor pharmaceutical composition includes one of dapagliflozin (e.g., (2S,3R,4R,5S,6R)-2-[4-chloro-3-[(4-ethoxyphenyl)methyl]phenyl]-6-(hydroxymethyl)oxane-3,4,5-triol), empagliflozin (e.g., (2S,3R,4R,5S,6R)-2-[4-chloro-3-[[4-[(3S)-oxolan-3-yl]oxyphenyl]methyl]phenyl]-6-(hydroxymethyl)oxane-3,4,5-triol), canagliflozin (e.g., (2S,3R,4R,5S,6R)-2-[3-[[5-(4-fluorophenyl)thiophen-2-yl]methyl]-4-methylphenyl]-6-(hydroxymethyl)oxane-3,4,5-triol), and/or ertugliflozin (e.g., (1S,2S,3S,4R,5S)-5-[4-chloro-3-[(4-ethoxyphenyl)methyl]phenyl]-1-(hydroxymethyl)-6,8-dioxabicyclo[3.2.1]octane-2,3,4-triol). These, and other, gliflozin Sodium-Glucose Cotransport 2 inhibitors are described, for example, in Dekkers et al., Curr. Diabetes Reports, 18:27 (2018), the content of which is hereby incorporated by reference.

In some embodiments, the gliflozin Sodium-Glucose Cotransport 2 inhibitor pharmaceutical composition includes any compound disclosed in U.S. Pat. No. 7,851,502, entitled "Pharmaceutical formulations containing an SGLT2 inhibitor," which is hereby incorporated by reference. In some embodiments, the gliflozin Sodium-Glucose Cotransport 2 inhibitor pharmaceutical composition includes any compound disclosed in U.S. Pat. No. 9,834,533, entitled "Process for preparing SGLT2 inhibitors and intermediates thereof," which is hereby incorporated by reference. In some embodiments, the gliflozin Sodium-Glucose Cotransport 2 inhibitor pharmaceutical composition includes any compound disclosed in U.S. Pat. No. 9,845,303, entitled "Process for the preparation of dapagliflozin," which is hereby incorporated by reference.

In some embodiments, the gliflozin Sodium-Glucose Cotransport 2 inhibitor pharmaceutical composition includes any compound disclosed in U.S. Pat. No. 8,853,412, entitled "Pyrrolidinone derivatives as GPR119 modulators for the treatment of diabetes, obesity, dyslipidemia and related disorders," which is hereby incorporated by reference.

In some embodiments, the gliflozin Sodium-Glucose Cotransport 2 inhibitor pharmaceutical composition includes any compound disclosed in U.S. Pat. No. 8,999,941, entitled "Crystalline and non-crystalline forms of SGLT2 inhibitors," which is hereby incorporated by reference. In some embodiments, the gliflozin Sodium-Glucose Cotransport 2 inhibitor pharmaceutical composition includes any compound disclosed in U.S. Pat. No. 9,695,159, entitled "Process for preparation of canagliflozin," which is hereby incorporated by reference In some embodiments, the gliflozin Sodium-Glucose Cotransport 2 inhibitor pharmaceutical composition includes any compound disclosed in U.S. Pat. No. 9,192,617, entitled "Pharmaceutical composition, methods for treating, and the uses thereof," which is hereby incorporated by reference. In some embodiments, the gliflozin Sodium-Glucose Cotransport 2 inhibitor pharmaceutical composition includes any compound disclosed in U.S. Pat. No. 9,902,751, entitled "Process for the preparation of empagliflozin," which is hereby incorporated by reference.

Referring to block 407, in some embodiments, the lowering of blood sugar is to treat type 2 diabetes. Typically, this is accomplished by a reduction in blood sugar amount or absorption.

In some embodiments, in response to receiving a first request from a user to be qualified for provision of a gliflozin Sodium-Glucose Cotransport 2 inhibitor pharmaceutical composition, the system creates a corresponding subject profile, e.g., containing biographic information about the subject, e.g., one or more of a subject name, date of birth, residence, delivery address, social security number, medical record number, insurance information, user name, identification password, etc. In some embodiments, the system registers a subject that has not previously received an over-the-counter provision of a gliflozin Sodium-Glucose Cotransport 2 inhibitor pharmaceutical composition as a new user of the gliflozin Sodium-Glucose Cotransport 2 inhibitor pharmaceutical composition, and the device will perform an initial assessment method for qualifying the subject for a provision of the gliflozin Sodium-Glucose Cotransport 2 inhibitor pharmaceutical composition, e.g., regardless of whether the subject previously received a provision of a gliflozin Sodium-Glucose Cotransport 2 inhibitor pharmaceutical composition via prescription.

In some embodiments, the system registers a subject that has previously received a provision of a gliflozin Sodium-Glucose Cotransport 2 inhibitor pharmaceutical composition via prescription as a previous user of the gliflozin Sodium-Glucose Cotransport 2 inhibitor pharmaceutical composition, and the device will perform a reassessment method for re-qualifying the subject for a provision of the gliflozin Sodium-Glucose Cotransport 2 inhibitor pharmaceutical composition.

In some embodiments, where the subject previously received a provision of a different gliflozin Sodium-Glucose Cotransport 2 inhibitor pharmaceutical composition via prescription, the system will perform a modified method for qualifying the subject for provision of the gliflozin Sodium-Glucose Cotransport 2 inhibitor pharmaceutical composition that accounts for differences in the contraindications and risk factors of the two gliflozin Sodium-Glucose Cotransport 2 inhibitor pharmaceutical compositions. For example, in response to receiving a request to qualify a user that previously received a provision of a pharmaceutical composition containing ertugliflozin via prescription, for an over-the-counter provision of dapagliflozin, the system performs a modified method for re-qualifying (e.g., a reassessment) the subject for the gliflozin Sodium-Glucose Cotransport 2 inhibitor pharmaceutical composition that includes a survey question and corresponding filter relating to whether the subject has had a body part amputated (e.g., regardless of whether a reassessment for a pharmaceutical composition containing ertugliflozin would normally consider a subject's history of amputation), because that factor would not have been considered when the subject received the prescription for the composition containing dapafliglozin.

In some embodiments, in response to receiving a second or subsequent request from a user to be qualified for provision of a gliflozin Sodium-Glucose Cotransport 2 inhibitor pharmaceutical composition, the system registers the subject as a returning customer, e.g., when the subject has previously received an over-the-counter provision of the gliflozin Sodium-Glucose Cotransport 2 inhibitor and a corresponding subject profile 232 already exists for the subject.

Figure 7A:
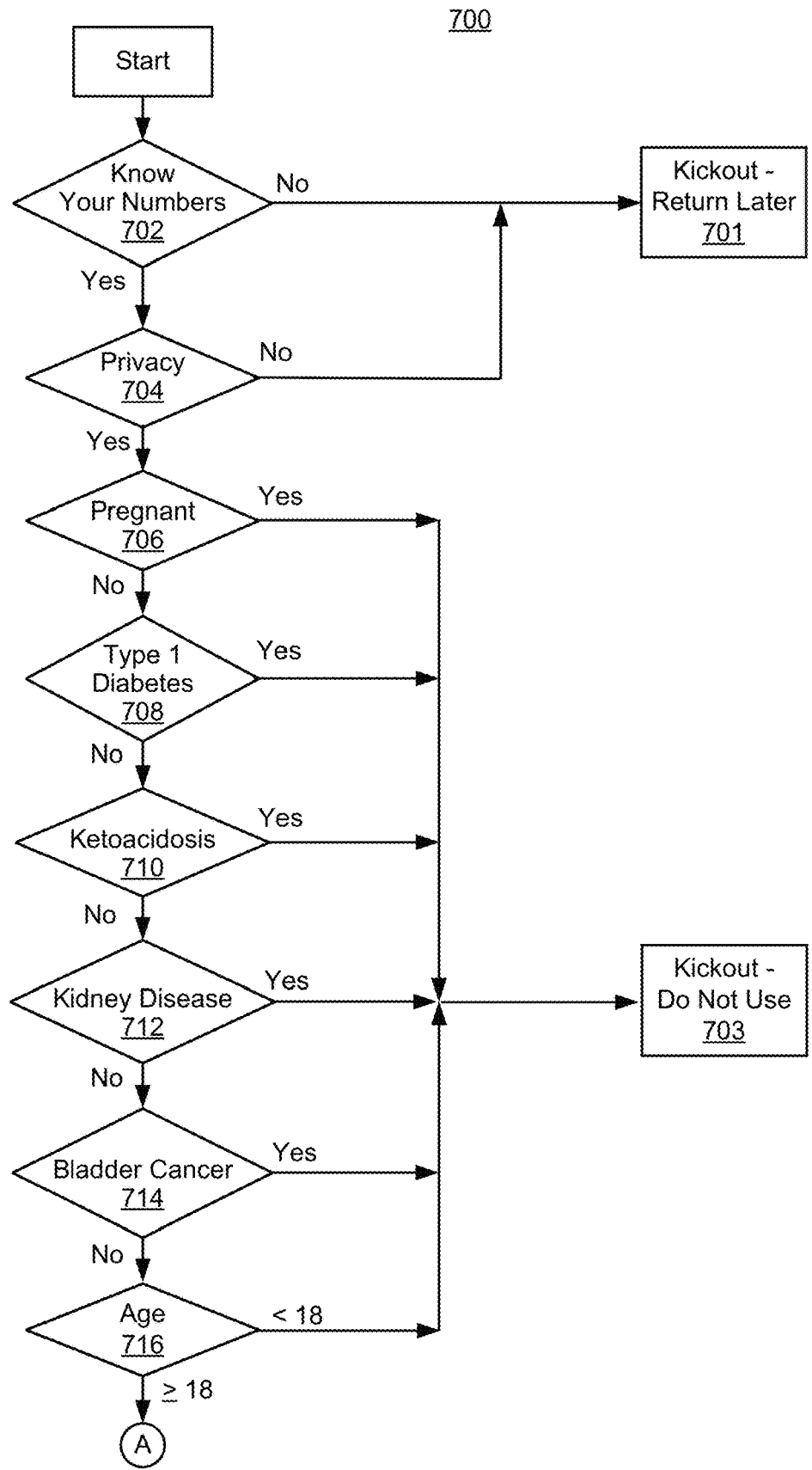
FIGS. 7A, 7B, and 7C collectively illustrate an example method for qualifying a subject for an over-the-counter provision of a gliflozin Sodium-Glucose Cotransport 2 inhibitor pharmaceutical composition, in accordance with an embodiment of the present disclosure.

In some embodiments, prior to proceeding with the qualification or re-qualification method, the device prompts (702, 704) the user to confirm that they have adequate privacy to provide sensitive medical information (e.g., prompt 704 in FIG. 7A) and/or that they are in possession of medical information required to complete the qualification process (e.g., prompt 702 to confirm that they have knowledge of their blood sugar level, in FIG. 7A).

Blocks 408-411.

Referring to block 408 of FIG. 4A, the method includes conducting a first survey of the subject thereby obtaining a first plurality of survey results (e.g., in response to survey questions 208, 212, e.g., one or more of the survey questions set forth in Table 1). In some embodiments, the device transmits one or more survey questions to the subject, prompting a response, and then receives a response to the one or more survey questions back from the subject. In some embodiments, the first survey results indicate some or all of the characteristics listed in Table 1. For example, in some embodiments, the first plurality of survey results indicates 2, 3, 4, 5, 6, 7, 8, 9, 10, 11, 12, 13, 14, 15, 16, 17, 18, 19, or all 20 of the characteristics listed in Table 1. In one embodiment, the first survey questions 208, 212 and results indicate at least characteristics 1-13 as provided in Table 1.

Figures 5A, 5B:
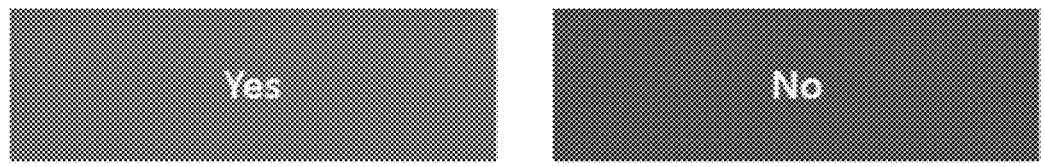
FIGS. 5A, 5B, 5C, and 5D collectively illustrates a first survey of a subject for obtaining a first plurality of survey results, in accordance with an embodiment of the present disclosure.
Figure 7B:
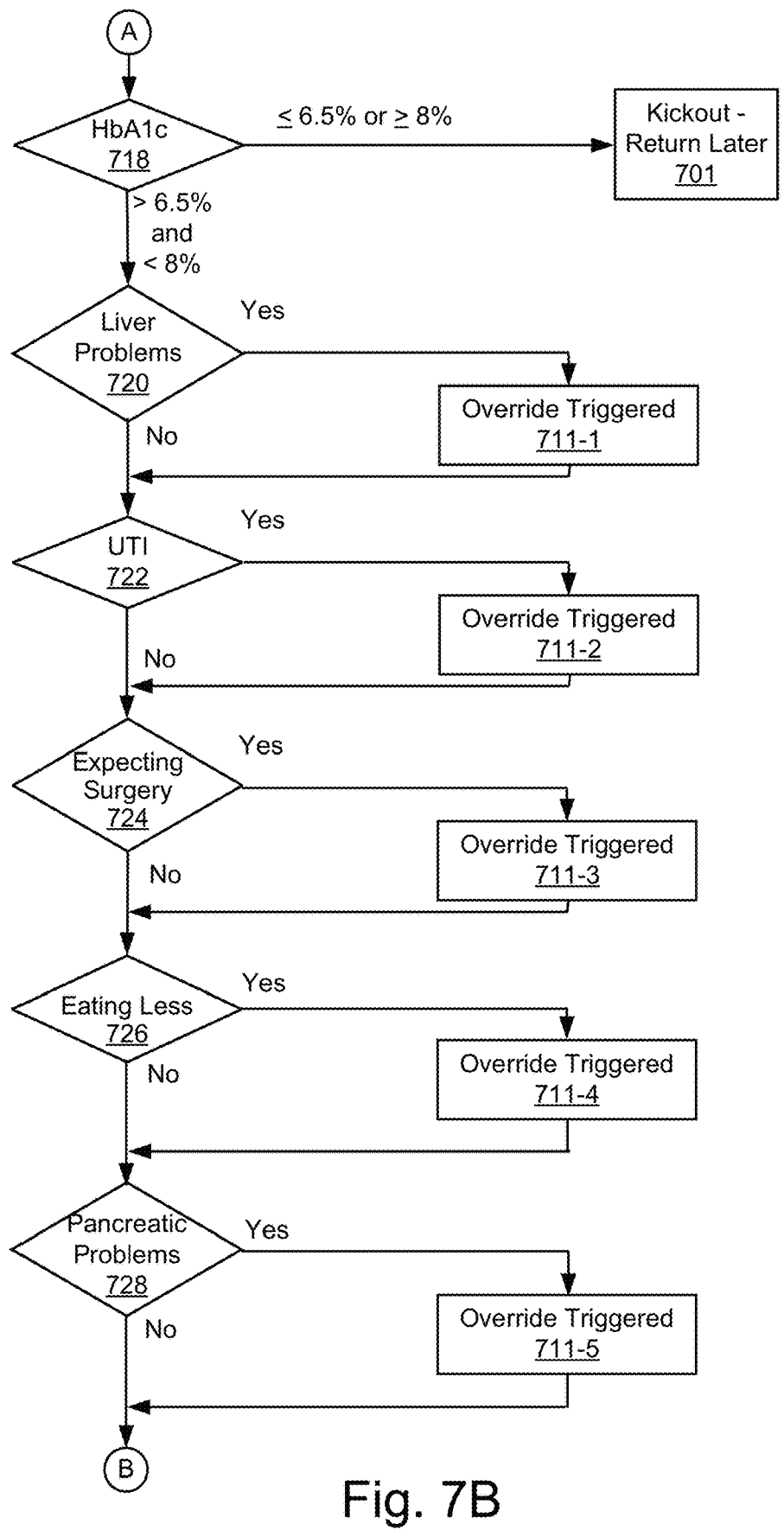
Figure 7C:
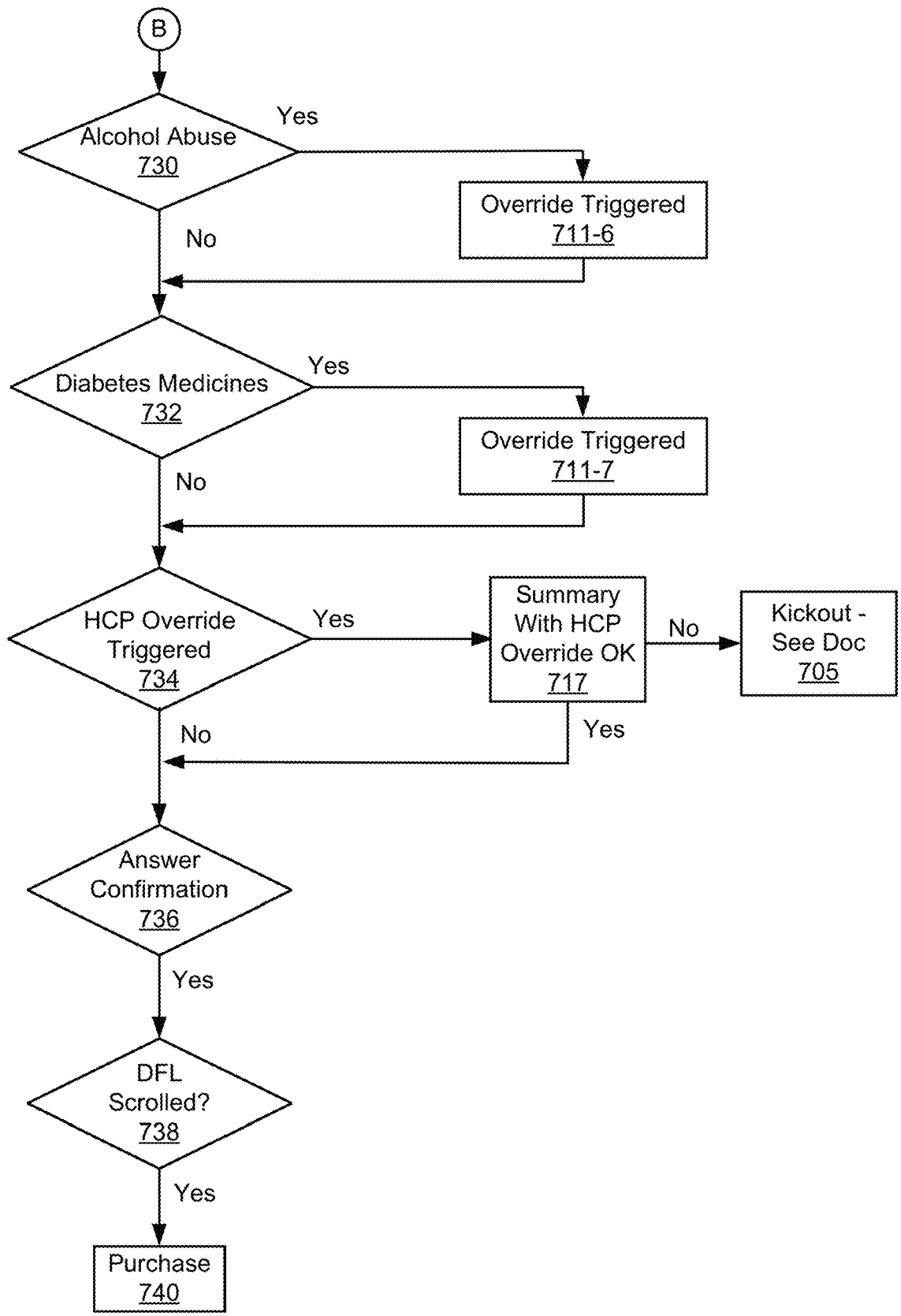

Referring to block 409, e.g., as illustrated in FIGS. 7A-7C, in some embodiments the first survey results indicate whether the subject is one of pregnant, breastfeeding, or planning to become pregnant (e.g., responsive to a survey question 208, such as question 502 illustrated in FIG. 5A, e.g., that is associated with and/or applied to (706) a pregnancy filter 216 of a first category class), whether the subject has Type 1 diabetes (e.g., responsive to a survey question 208 that is associated with and/or applied to (708) a Type 1 diabetes filter 216 of a first category class), a ketoacidosis status of the subject (e.g., responsive to a survey question 208 that is associated with and/or applied to (710) a ketoacidosis filter 216 of a first category class), a kidney disease status of the subject (e.g., responsive to a survey question 208 that is associated with and/or applied to (712) a kidney disease filter 216 of a first category class), an age of the subject (e.g., responsive to a survey question 208 that is associated with and/or applied to (716) an age filter 216 of a first category class), a blood sugar level of the subject (e.g., responsive to a survey question 208 that is associated with and/or applied to (718) a blood sugar filter 216 of a first category class), whether the subject has a liver problem (e.g., responsive to a survey question 212 that is associated with and/or applied to (720) a liver disease filter 222 of a second filter class category), whether the subject has a history of urinary problems (e.g., responsive to a survey question 212 that is associated with and/or applied to (722) a urinary problem filter 222 of a second category class), a surgery status of the subject, (e.g., responsive to a survey question 212 that is associated with and/or applied to (724) a surgery filter 222 of a second category class), a dietary status of the subject, (e.g., responsive to a survey question 212 that is associated with and/or applied to (726) a dietary filter 222 of a second category class), whether the subject has ever had a pancreatic problem, (e.g., responsive to a survey question 212 that is associated with and/or applied to (728) a pancreatic disease filter 222 of a second category class), an alcohol consumption status of the subject (e.g., responsive to a survey question 212 that is associated with and/or applied to (730) an alcohol consumption filter 222 of a second category class), and whether the subject is taking a diabetes medication (e.g., responsive to a survey question 212 that is associated with and/or applied to (732) a diabetes medication filter 222 of a second category class.

In some embodiments, e.g., when the gliflozin Sodium-Glucose Cotransport 2 inhibitor pharmaceutical composition includes dapagliflozin, the first plurality of survey results also includes whether the subject has ever had bladder cancer (e.g., responsive to a survey question 208 that is associated with and/or applied to (714) a bladder cancer filter 216 of a first category class).

In some embodiments, e.g., when the gliflozin Sodium-Glucose Cotransport 2 inhibitor pharmaceutical composition includes canagliflozin, the first plurality of survey results also includes a heart failure history of the subject, an amputation history of the subject, a leg neuropathy history of the subject, a diabetic foot ulcer history of the subject, and a hyperkalemia history of the subject (e.g., responsive to a survey question 210 that is associated with and/or applied to a heart failure, amputation, leg neuropathy, diabetic foot ulcer and/or hyperkalemia filter 220 of a second category class).

In some embodiments, e.g., when the gliflozin Sodium-Glucose Cotransport 2 inhibitor pharmaceutical composition includes ertugliflozin, the first plurality of survey results also includes an amputation history of the subject, a leg neuropathy history of the subject, and a diabetic foot ulcer history of the subject (e.g., responsive to a survey question 210 that is associated with and/or applied to an amputation, leg neuropathy, and/or diabetic foot ulcer filter 220 of a second category class).

In some embodiments, the first survey includes questions that elicit responses providing some or all of the characteristics listed in Table 1. In some embodiments, the survey includes questions corresponding to each of the survey results required for the methods described herein. In other embodiments, the survey includes questions corresponding to only a subset of the survey results required for the methods described herein. In some such embodiments, other survey results required for the methods described herein are acquired through other means (e.g., upon registration/subscription for a service associated with qualifying the subject for over-the-counter medication, from a healthcare professional, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare professional and information about the subject required for the methods described herein, e.g., one or more survey results, is acquired from a preexisting database associated with the personal medical identification (e.g., a last blood sugar measurement determined for the subject).

TABLE 1

Example characteristics for qualifying a subject for an over-the-counter provision of a gliflozin Sodium-Glucose Cotransport 2 inhibitor pharmaceutical composition

| Result | Example Characteristics |
|---|---|
| 1 | whether the subject is one of pregnant, breastfeeding, or planning to become pregnant |
| 2 | a Type 1 diabetes status of the subject |
| 3 | a ketoacidosis status of the subject |
| 4 | a kidney disease status of the subject |
| 5 | an age of the subject |
| 6 | a blood sugar level of the subject |
| 7 | whether the subject has a liver problem |
| 8 | whether the subject has ever had a urinary problem |
| 9 | a surgery status of the subject |
| 10 | a dietary status of the subject |
| 11 | whether the subject has ever had a pancreatic problem |
| 12 | an alcohol consumption status of the subject |
| 13 | whether the subject is taking a diabetes medication |
| 14 | a heart failure history of the subject |
| 15 | an amputation history of the subject |
| 16 | a leg neuropathy history of the subject |
| 17 | a diabetic foot ulcer history of the subject |
| 18 | a hyperkalemia history of the subject |
| 19 | whether the subject is allergic to the gliflozin Sodium-Glucose Cotransport 2 inhibitor pharmaceutical composition |
| 20 | whether the subject has ever had bladder cancer |

It is contemplated that, in some embodiments, any one or more of the survey questions 208, 212 provided in Table 1 will not be included in the first survey (e.g., will not be used for the assessment). For example, in some embodiments, a characteristic associated with a particular survey questions will be informative when qualifying a subject for one particular gliflozin Sodium-Glucose Cotransport 2 inhibitor but not for another gliflozin Sodium-Glucose Cotransport 2 inhibitor. For instance, in one embodiment, a process for qualifying a subject for a pharmaceutical composition containing dapagliflozin includes a survey question relating to whether the subject has ever had bladder cancer, while a process for qualifying a subject for a pharmaceutical composition containing ertugliflozin does not have such a questions, because prior bladder cancer is not contraindicated for ertugliflozin. The skilled artisan will recognize that different gliflozin Sodium-Glucose Cotransport 2 inhibitors carry different risks, contraindications, and drug interaction profiles. Accordingly, survey information required for qualifying a subject for access to one gliflozin Sodium-Glucose Cotransport 2 inhibitor with a known adverse drug interaction may not be necessary for qualifying the same subject for access to a second gliflozin Sodium-Glucose Cotransport 2 inhibitor.

Accordingly, it is contemplated that the first survey questions 208 include any subset of survey results provided in Table 1. For brevity, all possible combinations of the survey questions 208, 212 provided in Table 1 are not specifically delineated here. However, the skilled artisan will be able to envision any particular subset of the survey questions 208, 212 provided in Table 1. Likewise, the skilled artisan may know of other survey questions, not provided in Table 1, that may be combined with any subset of the survey questions provided in Table 1 to form the first survey questions used in the methods described herein.

In some embodiments, the first and/or second survey is conducted by transmitting a plurality of questions to the subject, e.g., some or all of the survey questions, and receiving answers to the plurality of survey questions before applying any of the answers to respective filters. For example, with reference to the workflow in FIG. 7, the device transmits questions relating to all of the filters of the first category class, all of the filters of the second category class, or all of the filters in the workflow (e.g., as a virtual survey where all of the questions are displayed in a single user interface, or as a series of questions displayed in consecutive user interfaces). After receiving answers to all of the survey questions, the device then applies the answers to all of the filters e.g., sequentially or concurrently) to determine whether the subject is qualified to receive provision of the gliflozin Sodium-Glucose Cotransport 2 inhibitor pharmaceutical composition. In alternative embodiments, the device transmits questions relating to just those filters of the first category class for which it could not obtain answers to the questions from an electronic database associated with the subject, such as electronic health record of the subject, and just those filters of the second category class it could not obtain answers to the questions from an electronic database associated with the subject (e.g., as a virtual survey where such unanswered questions are displayed in a single user interface, or as a series of questions displayed in consecutive user interfaces). After receiving answers to all of the survey questions, the device then applies the answers to all of the filters e.g., sequentially or concurrently, to determine whether the subject is qualified to receive provision of the gliflozin Sodium-Glucose Cotransport 2 inhibitor pharmaceutical composition.

In some embodiments, the first and/or second survey is conducted in a serial fashion, e.g., by transmitting a first question or a first group of survey questions (e.g., associated with a single filter) to the subject, receiving an answer to the single survey question or small group of survey questions, and applying the answer or answers to a filter, prior to transmitting a second question or second group of questions to the subject. For example, with reference to the workflow in FIG. 7, in some embodiments the device transmits a first question to the subject, relating to the pregnancy and/or breastfeeding status of the subject (e.g., question 502 'Are you or do you plan to become pregnant? Are you breastfeeding or planning to breastfeed?' in FIG. 5A). After receiving the answer to the survey question (e.g., 'yes or no'), the device applies the answer to a first pregnancy filter (704). If the first pregnancy filter is fired (e.g., in response to a "yes" answer), the device terminates (703) the process, and optionally provides the user with a message relating to why they are being denied a provision of the gliflozin Sodium-Glucose Cotransport 2 inhibitor pharmaceutical composition (e.g., as illustrated in FIG. 5B, message 504, advising the subject that taking the gliflozin Sodium-Glucose Cotransport 2 inhibitor pharmaceutical composition creates a risk for the fetus/baby).

In some embodiments, the first survey includes questions that elicit responses providing some or all of the characteristics listed in Table 1. In some embodiments, the survey includes questions corresponding to each of the survey results required for the methods described herein. In other embodiments, the survey includes questions corresponding to only a subset of the survey results required for the methods described herein. In some embodiments, the other survey results required for the methods described herein are acquired through other means (e.g., upon registration/subscription for a service associated with qualifying the subject for over-the-counter medication, from a healthcare professional, from a prior survey, from a database associated with a pharmacy, etc.) For example, in some embodiments, the subject provides a personal medical identification associated with an insurer, a hospital, or other healthcare professional and information about the subject required for the methods described herein, e.g., one or more survey results, is acquired from a preexisting database associated with the personal medical identification (e.g., a last blood sugar measurement determined for the subject). The same applies to the second survey 210 and corresponding results applied to the first survey 206.

Referring to block 410, in some embodiments the first plurality of survey results further includes whether the subject is allergic to the gliflozin Sodium-Glucose Cotransport 2 inhibitor pharmaceutical composition. In some embodiments, and the first plurality of filters further includes an adverse reaction filter that is fired when the first plurality of survey results indicates that the subject is allergic to the gliflozin Sodium-Glucose Cotransport 2 inhibitor pharmaceutical composition.

Referring to block 411, in some embodiments the first plurality of survey results further includes whether the subject has ever had bladder cancer (e.g., filter 7a in Table 2). In some embodiments, and the first plurality of filters further includes a bladder cancer filter that is fired when the first plurality of survey results indicates that the subject has had bladder cancer.

Blocks 412-422.

Referring to block 412 of FIG. 4B-4C, all or a portion of the first survey results are run against a first plurality of filters of a first category class 214. As previously described, the first plurality of filters includes a subset of filters 216 of the first filter category class 214. When a respective filter in the first plurality of filters is fired (e.g., when a survey result indicates that a triggering condition 218 has been met), the subject is deemed not qualified for delivery of the gliflozin Sodium-Glucose Cotransport 2 inhibitor pharmaceutical composition and the method is terminated without delivery of the gliflozin Sodium-Glucose Cotransport 2 inhibitor pharmaceutical composition.

In some embodiments, when the method is terminated without delivery of the gliflozin Sodium-Glucose Cotransport 2 inhibitor pharmaceutical composition, the subject is prevented from attempting to requalify for the gliflozin Sodium-Glucose Cotransport 2 inhibitor pharmaceutical composition for a predetermined period of time, e.g., at least a day, at least a week, at least a month, etc. This prevents the subject from abusing the systems and methods of the present disclosure.

Referring to blocks 413-422, specific filters 216 in the first plurality of filters and their exemplary triggering conditions 218 that cause the corresponding filter to fire are detailed below.

In some embodiments, the first plurality of filters of the first category class 214 includes some or all of the filters 216 listed in Table 2. For example, in some embodiments, the first plurality of filters results indicates 2, 3, 4, 5, 6, or all 7 of the filters listed in Table 2. In one embodiment, the first plurality of filters includes at least filters 1-6 as provided in Table 2.

TABLE 2

Example filters for contraindications associated with qualifying a subject for an over-the-counter provision of a gliflozin Sodium-Glucose Cotransport 2 inhibitor pharmaceutical composition

| Filter | Example Criteria |
|---|---|
| 1a | a first pregnancy filter |
| 2a | a Type 1 diabetes filter |
| 3a | a first ketoacidosis filter |
| 4a | a kidney disease filter |
| 5a | an age filter |
| 6a | a first blood sugar filter |
| 7a | a bladder cancer filter |

It is contemplated that, in some embodiments, any one or more of the filters 216 provided in Table 2 will not be included in the first plurality of filters. For example, in some embodiments, a characteristic associated with a particular survey result will be informative when qualifying a subject for one particular gliflozin Sodium-Glucose Cotransport 2 inhibitor but not for another gliflozin Sodium-Glucose Cotransport 2 inhibitor. For example, whether the subject has a history of diabetic foot ulcers is informative when qualifying a subject for a composition containing ertugliflozin, but not when qualifying a subject for a composition containing dapagliflozin.

Accordingly, it is contemplated that the first plurality of filters includes any sub-set of filters 216 provided in Table 2. Likewise, the skilled artisan may know of other filters 216, not provided in Table 2, which may be combined with any subset of the filters 216 provided in Table 2 to form the first plurality of filters results used in the methods described herein. For brevity, all possible combinations of the filters 216 provided in Table 2 are not specifically delineated here.

Referring to blocks 413-414 of FIG. 4B, in some embodiments the first plurality of filters includes a first pregnancy filter (e.g., first pregnancy filter 216-1 in FIG. 3 and/or filter 1a in Table 2). In some embodiments, the first pregnancy filter is configured to be fired at least when the first plurality of survey results indicates that the subject is pregnant or the subject is breastfeeding. In some embodiments, the first pregnancy filter is also configured to be fired when the subject is planning on becoming pregnant within a predetermined period of time. When the first pregnancy filter is fired, the subject is not permitted to obtain the gliflozin Sodium-Glucose Cotransport 2 inhibitor pharmaceutical composition over-the-counter (e.g., the method is terminated without authorizing provision of the gliflozin Sodium-Glucose Cotransport 2 inhibitor pharmaceutical composition to the subject). For example, the device transmits prompt 502, as illustrated in FIG. 5A, to the subject and the device applies the subject's answer to the first pregnancy filter. If the subject's answer indicates that they are pregnant, they are planning on becoming pregnant, they are breastfeeding, or they are planning to breastfeeding, the pregnancy filter is fired, and the method is terminated without authorizing provision of the gliflozin Sodium-Glucose Cotransport 2 inhibitor pharmaceutical composition to the subject. In some embodiments, the device transmits a message explaining why authorization was denied, e.g., message 504 illustrated in FIG. 5B.

Referring to block 415 of FIG. 4B, in some embodiments the first plurality of filters includes a Type 1 diabetes filter (e.g., Type 1 diabetes 216-2 in FIG. 3 and/or filter 2a in Table 2). The Type 1 diabetes filter is configured to be fired at least when the first plurality of survey results indicates that the subject has Type 1 diabetes. If the Type 1 diabetes filter is fired, the subject is not permitted to obtain the gliflozin Sodium-Glucose Cotransport 2 inhibitor pharmaceutical composition pharmaceutical composition over-the-counter (e.g., the method is terminated without authorizing provision of the gliflozin Sodium-Glucose Cotransport 2 inhibitor pharmaceutical composition to the subject).

Referring to block 416 of FIG. 4B, in some embodiments the first plurality of filters includes a first ketoacidosis filter (e.g., first ketoacidosis filter 216-3 in FIG. 3 and/or filter 3a in Table 2). The first ketoacidosis filter is configured to be fired at least when the first plurality of survey results indicates that the subject has ketoacidosis. If the ketoacidosis filter is fired, the subject is not permitted to obtain the gliflozin Sodium-Glucose Cotransport 2 inhibitor pharmaceutical composition pharmaceutical composition over-the-counter (e.g., the method is terminated without authorizing provision of the gliflozin Sodium-Glucose Cotransport 2 inhibitor pharmaceutical composition to the subject).

Referring to block 417 of FIG. 4B, in some embodiments the first plurality of filters includes a kidney disease filter (e.g., kidney disease filter 216-4 in FIG. 3 and/or filter 4a in Table 2). In some embodiments, the kidney disease filter is fired when the first plurality of survey results indicates that the subject has kidney disease. If the kidney disease filter is fired, the subject is not permitted to obtain the gliflozin Sodium-Glucose Cotransport 2 inhibitor pharmaceutical composition pharmaceutical composition over-the-counter (e.g., the method is terminated without authorizing provision of the gliflozin Sodium-Glucose Cotransport 2 inhibitor pharmaceutical composition to the subject).

Referring to blocks 418-419 of FIG. 4B, in some embodiments the first plurality of filters includes an age filter (e.g., age filter 216-5 in FIG. 3 and/or filter 5a in Table 2). In some embodiments, the age filter is fired when the first plurality of survey results indicates that the subject is less than eighteen years old. If the age filter is fired, the subject is not permitted to obtain the gliflozin Sodium-Glucose Cotransport 2 inhibitor pharmaceutical composition pharmaceutical composition over-the-counter (e.g., the method is terminated without authorizing provision of the gliflozin Sodium-Glucose Cotransport 2 inhibitor pharmaceutical composition to the subject).

Referring to blocks 420-422 of FIG. 4B, in some embodiments the first plurality of filters includes a first blood sugar filter (e.g., first blood sugar filter 216-6 in FIG. 3 and/or filter 6a in Table 2). In some embodiments, the first blood sugar filter is fired when the first plurality of survey results indicates that the subject has a blood sugar level that is either below a first baseline blood sugar level or above a ceiling blood sugar level. If the first blood sugar filter is fired, the subject is not permitted to obtain the gliflozin Sodium-Glucose Cotransport 2 inhibitor pharmaceutical composition pharmaceutical composition over-the-counter (e.g., the method is terminated without authorizing provision of the gliflozin Sodium-Glucose Cotransport 2 inhibitor pharmaceutical composition to the subject). In some embodiments, the first baseline blood sugar level used in the first blood sugar filter is 6.5% glycated hemoglobin. In some embodiments, the ceiling blood sugar level used in the first blood sugar filter is from 7.5% glycated hemoglobin to 8% glycated hemoglobin.

Blocks 423-434, and 476-481.

Referring to block 423 of FIGS. 4C-4D, the method also includes running all or a portion of the first survey results against a second plurality of filters of a second category class 220. When a respective filter in the second plurality of filters is fired, the subject is provided with a warning 226 corresponding to the respective filter (e.g., filter warning 226-4 corresponds to filter 222-4). In some embodiments, the warning 226 is provided as a next step, e.g., prior to applying survey results to any subsequent filters, after the corresponding filter is fired. For example, with respect to FIG. 7B-7C in some embodiments, when the liver disease filter is triggered at 720, the device would provide the subject with a warning prior to proceeding to the drug interaction filter at 711, e.g., requiring the subject confirm they have discussed their history of liver disease with a health care professional, e.g., and the healthcare professional still recommends taking a gliflozin Sodium-Glucose Cotransport 2 inhibitor pharmaceutical composition. In some embodiments the warning 226 is provided after applying survey results to all subsequent filters. For example, as illustrated in FIG. 7B, in some embodiments, when the lever disease filter is triggered at 770, the device would proceed to the urinary problem filter at 722 prior to transmitting a warning to the subject, and then transmit all warnings corresponding to filters of the second category class, at 736, as illustrated in FIG. 7C, after survey results have been applied to all subsequent filters.

In some embodiments, the second plurality of filters 222 of the second category class 220 includes some or all of the filters listed in Table 3. For example, in some embodiments, the first plurality of filters includes 2, 3, 4, 5, 6, 7, 8, 9, 10, 11, 12, or all 13 of the filters listed in Table 3. In one embodiment, the first plurality of filters includes at least filters 1-7 as provided in Table 3

TABLE 3

Example filters for risk factors associated with qualifying a subject for an over-the-counter provision of a gliflozin Sodium-Glucose Cotransport 2 inhibitor pharmaceutical composition

| Filter | Example Criteria |
|--------|------------------|
| 1a | a first liver disease filter |
| 2a | a first urinary problem filter |
| 3a | a first surgery filter |
| 4a | a first dietary filter |
| 5a | a first pancreatic disease filter |
| 6a | a first alcohol consumption filter |
| 7a | a first diabetes medication filter |
| 8a | a bladder cancer filter |
| 9a | a heart failure filter |
| 10a | an amputation filter |
| 11a | a leg neuropathy filter |
| 12a | a diabetic foot ulcer filter |
| 13a | a hyperkalemia filter |

Referring to block 425, in some embodiments, the second plurality of filters includes a first liver disease filter (e.g., first liver disease filter 222-1 in FIG. 3 and/or filter 1a in Table 3). The first liver disease filter is configured to be fired at least when the first plurality of survey results indicate that the subject has had a liver problem. In some embodiments, liver problems that are capable of triggering the first liver disease filter include impaired hepatic function, acute liver failure, and cholestasis. When the first liver disease filter is fired, the device transmits a warning corresponding to the first liver disease filter, and requires the user to acknowledge the warning before authorizing a provision of the gliflozin Sodium-Glucose Cotransport 2 inhibitor pharmaceutical composition.

Referring to blocks 426-427, in some embodiments, the second plurality of filters includes a first urinary problem filter (e.g., first urinary problem filter 222-2 in FIG. 3 and/or filter 2a in Table 3). The first urinary problem filter is configured to be fired at least when the first plurality of survey results indicates that the subject has a history of urinary problems. When the first urinary problem filter is fired, the device transmits a warning corresponding to the first urinary problem filter, and requires the user to acknowledge the warning before authorizing a provision of the gliflozin Sodium-Glucose Cotransport 2 inhibitor pharmaceutical composition. In some embodiments, the first urinary problem filter is also fired when the first plurality of survey results indicates that the subject has a history of urinary tract infections or problems urinating.

Referring to block 428, in some embodiments, the second plurality of filters includes a first surgery filter (e.g., first surgery filter 222-3 in FIG. 3 and/or filter 3a in Table 3). The first surgery filter is configured to be fired at least when the first plurality of survey results indicates that the subject is planning on undergoing surgery. When the first surgery filter is fired, the device transmits a warning corresponding to the first surgery filter, and requires the user to acknowledge the warning before authorizing a provision of the gliflozin Sodium-Glucose Cotransport 2 inhibitor pharmaceutical composition.

Referring to blocks 429-430 in FIG. 4D, in some embodiments, the second plurality of filters includes a first dietary filter (e.g., first dietary filter 222-4 in FIG. 3 and/or filter 4a in Table 3). The first dietary filter is configured to be fired at least when the first plurality of survey results indicates that the subject is eating less than before. When the first dietary filter is fired, the device transmits a warning corresponding to the first dietary filter, and requires the user to acknowledge the warning before authorizing a provision of the gliflozin Sodium-Glucose Cotransport 2 inhibitor pharmaceutical composition. In some embodiments, the first dietary filter is fired when the first plurality of survey results indicates that the subject is eating less due to illness, surgery, or a recent change in diet.

Referring to block 431, in some embodiments, the second plurality of filters includes a first pancreatic disease filter (e.g., first pancreatic disease filter 222-5 in FIG. 3 and/or filter 5a in Table 3). The first pancreatic disease filter is configured to be fired at least when the first plurality of survey results indicates that the subject has a pancreatic problem. When the first pancreatic disease filter is fired, the device transmits a warning corresponding to the first pancreatic disease filter, and requires the user to acknowledge the warning before authorizing a provision of the gliflozin Sodium-Glucose Cotransport 2 inhibitor pharmaceutical composition.

Referring to blocks 432-433, in some embodiments, the second plurality of filters includes a first alcohol consumption filter (e.g., first alcohol consumption filter 222-6 in FIG. 3 and/or filter 6a in Table 3). When the first alcohol consumption filter is fired, the device transmits a warning corresponding to the first alcohol consumption filter, and requires the user to acknowledge the warning before authorizing a provision of the gliflozin Sodium-Glucose Cotransport 2 inhibitor pharmaceutical composition. In some embodiments, the first alcohol consumption filter is fired when the first plurality of survey results indicates that the subject, on average, consumes at least a predetermined number of alcoholic drinks over a predetermined period of time.

Referring to block 434, in some embodiments, the second plurality of filters includes a first diabetes medication filter (e.g., first diabetes medication filter 222-7 in FIG. 3 and/or filter 7a in Table 3). The first diabetes medication filter is configured to be fired at least when the first plurality of survey results indicates that the subject is taking a diabetes medication. When the first diabetes medication filter is fired, the device transmits a warning corresponding to the first diabetes medication filter, and requires the user to acknowledge the warning before authorizing a provision of the gliflozin Sodium-Glucose Cotransport 2 inhibitor pharmaceutical composition.

Referring to blocks 476-478 of FIG. 4K, in some embodiments the gliflozin Sodium-Glucose Cotransport 2 inhibitor pharmaceutical composition includes canagliflozin. When gliflozin Sodium-Glucose Cotransport 2 inhibitor pharmaceutical composition includes canagliflozin, the second plurality of filters further includes a heart failure filter (e.g., filter 9a in Table 3), an amputation filter (e.g., filter 10a in Table 3), a leg neuropathy filter (e.g., filter 11a in Table 3), a diabetic foot ulcer filter (e.g., filter 12a in Table 3), and a hyperkalemia filter (e.g., filter 13a in Table 3). In some embodiments, the heart failure filter is fired when the first plurality of survey results indicates that the subject has a history of heart failure. In some embodiments, the amputation filter is triggered at least when the first plurality of survey results indicates that the subject has had a body part amputated. In some embodiments, the leg neuropathy filter is triggered at least when the first plurality of survey results indicates that the subject has a leg neuropathy. In some embodiments, the diabetic foot ulcer filter is triggered at least when the first plurality of survey results indicates that the subject has had a diabetic foot ulcer. In some embodiments, the hyperkalemia filter is triggered at least when the first plurality of survey results indicates that the subject has hyperkalemia.

Referring to blocks 479-481 of FIG. 4K, in some embodiments the gliflozin Sodium-Glucose Cotransport 2 inhibitor pharmaceutical composition includes ertugliflozin. When gliflozin Sodium-Glucose Cotransport 2 inhibitor pharmaceutical composition includes ertugliflozin, the second plurality of filters further includes an amputation filter (e.g., filter 10a in Table 3), a leg neuropathy filter (e.g., filter 11a in Table 3), and a diabetic foot ulcer filter (e.g., filter 12a in Table 3). In some embodiments, the amputation filter is triggered at least when the first plurality of survey results indicates that the subject has had a body part amputated. In some embodiments, the leg neuropathy filter is triggered at least when the first plurality of survey results indicates that the subject has a leg neuropathy. In some embodiments, the diabetic foot ulcer filter is triggered at least when the first plurality of survey results indicates that the subject has had a diabetic foot ulcer.

It is contemplated that, in some embodiments, any one or more of the filters provided in Table 3 will not be included in the second plurality of filters. For example, in some embodiments, a characteristic associated with a particular survey result will be informative when qualifying a subject for one particular gliflozin Sodium-Glucose Cotransport 2 inhibitor pharmaceutical composition but not for another gliflozin Sodium-Glucose Cotransport 2 inhibitor pharmaceutical composition. Accordingly, it is contemplated that the second plurality of filters includes any sub-set of filters provided in Table 3. Likewise, the skilled artisan may know of other filters, not provided in Table 3, that may be combined with any subset of the filters provided in Table 3 to form the second plurality of filters results used in the methods described herein.

Contraindications and risk factors described in the present disclosure are non-exhaustive. The skilled artisan may know of other contraindications for a particular the gliflozin Sodium-Glucose Cotransport 2 inhibitor pharmaceutical composition and/or treat risk factors as contraindications dependent upon the intended use of the gliflozin Sodium-Glucose Cotransport 2 inhibitor pharmaceutical composition. In some embodiments, contraindications for use of a prescription-strength pharmaceutical agent are treated only as risk factors, or not at all, when qualifying a subject for a lower-dose OTC use of a gliflozin Sodium-Glucose Cotransport 2 inhibitor pharmaceutical composition.

Accordingly, it will be appreciated that the survey questions 208, 212, and filters 216, 222 applied to the survey answers thereof, may vary depending upon the gliflozin Sodium-Glucose Cotransport 2 inhibitor pharmaceutical composition being distributed. This is due to differences in the contraindication profiles of the various the gliflozin Sodium-Glucose Cotransport 2 inhibitor pharmaceutical compositions, e.g., due to different drug-drug interactions, routes of drug clearance, etc. of the different the gliflozin Sodium-Glucose Cotransport 2 inhibitor pharmaceutical compositions. For example, administration of canagliflozin to patients with moderate renal impairment results in a higher incidence of hyperkalemia. Mikhail. Curr. Drug Safety. 9:127-132 (2014). However, administration of dapagliflozin is not correlated with an increased risk of hyperkalemia. As such, in some embodiments, a survey qualifying a subject for OTC use of canagliflozin may ask whether the subject has a history of hyperkalemia, while a survey qualifying a subject for OTC use of dapagliflozin may not.

Referring to block 435 of FIG. 4D, the method includes obtaining acknowledgment from the subject for any warning 226 issued to the subject by any filter 222 in the second plurality of filters.

Referring to block 424, in some embodiments the warning 226 corresponding to a respective filter 222 in the second plurality of filters includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a gliflozin Sodium-Glucose Cotransport 2 inhibitor pharmaceutical composition in view of the underlying risk factor. Accordingly, acknowledgement is obtained from the subject when the subject indicates that they have discussed the risk factor underlying the respective filter in the second plurality of filters that was fired with a health care professional. For example, message 602 in FIG. 6 illustrates a warning that is generic to any fired filters. In some embodiments, the warning is specific to a particular filter (e.g., filter warning 226 in FIG. 2), communicating to the user why the filter was fired.

In some embodiments, an acknowledgment from the user is verified by the health care practitioner (e.g., the method requires verification in order for authorization of the provision of the gliflozin Sodium-Glucose Cotransport 2 inhibitor pharmaceutical composition), for example in order to verify an accuracy of the survey results of the subject. In some embodiments, when the acknowledgment is verified by the heath care practitioner, the subject is deemed a trusted subject, such that verification of future results is not required.

Blocks 436-441.

Referring to blocks 436-439 of FIG. 4E, the process control proceeds to the fulfillment process when no filter 216 in the first plurality of filters has been fired and the subject has acknowledged each warning 226 associated with each filter 222 in the second plurality of filters that was fired. In some embodiments, the fulfillment process includes storing an indication in a subject profile 232 of an initial order date and/or destination for the gliflozin Sodium-Glucose Cotransport 2 inhibitor pharmaceutical composition. The initial order date is utilized, for example, to verify at least a refill status of a provision of the gliflozin Sodium-Glucose Cotransport 2 inhibitor. The initial order date is also utilized, for example, to verify at least an elapsed period of time between an initial order and a future re-order. Such verification is required in order to ensure that certain tests (e.g., blood sugar tests) are taken regularly.

The fulfillment process further includes communicating an over-the-counter drug facts label 230 for the gliflozin Sodium-Glucose Cotransport 2 inhibitor pharmaceutical composition to the subject. In some embodiments, the drug facts label is communicated to the subject in real-time, e.g., within the same user interface as used for the qualification process. In some embodiments, the over-the-counter drug facts label 230 specifies what the gliflozin Sodium-Glucose Cotransport 2 inhibitor pharmaceutical composition is for (e.g., for lowering blood sugar, treating diabetes, etc.) and any risks associated with taking the gliflozin Sodium-Glucose Cotransport 2 inhibitor pharmaceutical composition (e.g., drug-drug interactions, pharmacokinetic interactions, adverse reactions, etc.). For instance, in some embodiments, the over-the-counter drug facts label 230 specifies that the gliflozin Sodium-Glucose Cotransport 2 inhibitor pharmaceutical composition is to be taken by the subject at a predetermined dosage per day that is from 5 mg to 10 mg per day (block 438). In another example embodiment, the over-the-counter drug facts label 230 specifies that the gliflozin Sodium-Glucose Cotransport 2 inhibitor pharmaceutical composition is to be taken by the subject at a predetermined dosage per day that is 5 mg per day (block 439).

Referring to blocks 440-441 of FIG. 4E, in some embodiments the fulfillment process further includes authorizing provision of the gliflozin Sodium-Glucose Cotransport 2 inhibitor pharmaceutical composition to the subject. The authorization occurs upon confirmation from the subject that the over-the-counter drug facts label 230 has been received and read by the subject. In some embodiments, this authorization includes a destination associated with the subject. In some embodiments, the destination associated with the subject is stored in the subject profile 232. In some embodiments, the destination associated with the subject is a physical address including a street address, a Post Office box, a pharmacy associated with the subject, a health care professional associated with the subject, and/or one or more coordinates (e.g., longitude, latitude, elevation). In some embodiments, the provision of the gliflozin Sodium-Glucose Cotransport 2 inhibitor pharmaceutical composition to the subject includes shipping the gliflozin Sodium-Glucose Cotransport 2 inhibitor pharmaceutical composition to the physical address associated with the subject (block 441). In some embodiments, the provision of the gliflozin Sodium-Glucose Cotransport 2 inhibitor pharmaceutical composition to the subject includes shipping the gliflozin Sodium-Glucose Cotransport 2 inhibitor pharmaceutical composition to a pharmacy associated and/or a location associated with a health care professional of the subject and/or an office of a medical practitioner associated with the subject.

Blocks 442-475.

Referring to blocks 442-475 of FIGS. 4E-4K, a re-fulfillment process will be described infra. In some embodiments, the present disclosure provides a method for qualifying a subject for a refill of a gliflozin Sodium-Glucose Cotransport 2 inhibitor pharmaceutical composition. In some embodiments, the qualification for a refill of the gliflozin Sodium-Glucose Cotransport 2 inhibitor pharmaceutical composition follows an initial qualification of the subject, as described herein. In some embodiments, the qualification for a refill of the gliflozin Sodium-Glucose Cotransport 2 inhibitor pharmaceutical composition follows issuance of a prescription to the subject for the gliflozin Sodium-Glucose Cotransport 2 inhibitor pharmaceutical composition. For example, in some embodiments, a subject who is new to the qualification process is asked whether they previously received a prescription for the gliflozin Sodium-Glucose Cotransport 2 inhibitor pharmaceutical composition and, if the subject indicates that they have not previously received a prescription, the subject is directed to an initial qualification method and, if the subject indicates that they have previously received a prescription, the subject is directed to the refill qualification method, e.g., as described below.

Referring to block 442 of FIG. 4E, in some embodiments a re-fulfillment procedure is performed. The re-fulfillment procedure is responsive to receiving a re-order request from the subject for the gliflozin Sodium-Glucose Cotransport 2 inhibitor pharmaceutical composition. In some embodiments, a prompt to initiate the re-fulfillment procedure is sent to user device 102 associated with the subject after a predetermined amount of time associated with a duration of dosages previously delivered to the subject (e.g., the user is reminded to fulfill their order of the gliflozin Sodium-Glucose Cotransport 2 inhibitor pharmaceutical composition just before, or just after, the user is scheduled to run out of a previously delivered provision.

Referring to blocks 443-444 of FIG. 4F, in some embodiments the re-fulfillment procedure includes conducting a second survey of the subject. The second survey is configured to obtain a second plurality of survey results. These results are derived from corresponding survey questions (e.g., the device transmits one or more survey questions to the user, prompting a response, and then receives a response to the one or more survey questions back from the subject). In some embodiments, the second plurality of survey results indicate some or all of the characteristics listed in Table 4. For example, in some embodiments, the second plurality of survey results indicates 1, 2, 3, 4, 5, 6, 7, 8, 9, 10, 11, 12, 13, 14, 15, 16, 17, 18, 19, 20, or all 21 of the characteristic listed in Table 4. In one embodiment, the second survey questions and results indicate at least characteristics 1-11 as provided in Table 4.

In some embodiments, the second survey results includes at least one of: whether the subject is one of pregnant, breastfeeding, or planning to become pregnant (e.g., responsive to a survey question that is associated with and/or applied to (812) a second pregnancy filter of a first category class 214-2), whether the subject has developed ketoacidosis since receiving their last provision of the gliflozin Sodium-Glucose Cotransport 2 inhibitor pharmaceutical composition (e.g., responsive to a survey question that is associated with and/or applied to (814), a ketoacidosis filter of a first category class 214-2), whether the subject has developed a kidney problem since receiving their last provision of the gliflozin Sodium-Glucose Cotransport 2 inhibitor pharmaceutical composition (e.g., responsive to a survey question that is associated with and/or applied to (816), a kidney problem filter of a first category class 214-2), whether the subject has developed a urinary tract infection since receiving their last provision of the gliflozin Sodium-Glucose Cotransport 2 inhibitor pharmaceutical composition (e.g., responsive to a survey question that is associated with and/or applied to (818), a second urinary problem filter of a first category class 214-2), whether the subject is experiencing a bodily stress (e.g., responsive to a survey question that is associated with and/or applied to (838), a bodily stress filter of a first category class 214-2), whether the subject is taking a diabetes medication (e.g., responsive to a survey question that is associated with and/or applied to (840), a second diabetes medication filter of a first category class 214-2), whether the subject has developed a liver problem since receiving their last provision of the gliflozin Sodium-Glucose Cotransport 2 inhibitor pharmaceutical composition (e.g., responsive to a survey question that is associated with and/or applied to (824) a second liver disease filter of a second category class 220-2), whether the subject is planning on undergoing surgery (e.g., responsive to a survey question that is associated with and/or applied to (826) a second surgery filter of a second category class 220-2), whether the subject is eating less since receiving their last provision of the gliflozin Sodium-Glucose Cotransport 2 inhibitor pharmaceutical composition (e.g., responsive to a survey question that is associated with and/or applied to (828) a second dietary filter of a second category class 220-2), whether the subject has developed a pancreatic problem since receiving their last provision of the gliflozin Sodium-Glucose Cotransport 2 inhibitor pharmaceutical composition (e.g., responsive to a survey question that is associated with and/or applied to (830) a second pancreatic disease filter of a second category class 220-2), an alcohol consumption status of the subject (e.g., responsive to a survey question that is associated with and/or applied to (832) a second alcohol consumption filter of a second category class 220-2), whether the subject has experienced a yeast infection since receiving their last provision of the gliflozin Sodium-Glucose Cotransport 2 inhibitor pharmaceutical composition (e.g., responsive to a survey question that is associated with and/or applied to (834) a yeast infection filter of a second category class 220-2), and whether the subject has developed hypoglycemia since receiving their last provision of the gliflozin Sodium-Glucose Cotransport 2 inhibitor pharmaceutical composition (e.g., responsive to a survey question that is associated with and/or applied to (836) a hypoglycemia symptom filter of a second category class 220-2).

In some embodiments, e.g., when the gliflozin Sodium-Glucose Cotransport 2 inhibitor pharmaceutical composition includes canagliflozin, the second plurality of survey results further includes one or more of: whether the subject has developed heart failure since receiving their last provision of the gliflozin Sodium-Glucose Cotransport 2 inhibitor pharmaceutical composition, whether the subject has had a body part amputated since receiving their last provision of the gliflozin Sodium-Glucose Cotransport 2 inhibitor pharmaceutical composition, whether the subject has developed leg neuropathy since receiving their last provision of the gliflozin Sodium-Glucose Cotransport 2 inhibitor pharmaceutical composition, whether the subject has developed a diabetic foot ulcer since receiving their last provision of the gliflozin Sodium-Glucose Cotransport 2 inhibitor pharmaceutical composition, and whether the subject has developed hyperkalemia since receiving their last provision of the gliflozin Sodium-Glucose Cotransport 2 inhibitor pharmaceutical composition.

In some embodiments, e.g., when the gliflozin Sodium-Glucose Cotransport 2 inhibitor pharmaceutical composition includes ertugliflozin, the second plurality of survey results further includes one or more of: whether the subject has had a body part amputated since receiving their last provision of the gliflozin Sodium-Glucose Cotransport 2 inhibitor pharmaceutical composition, whether the subject has developed leg neuropathy since receiving their last provision of the gliflozin Sodium-Glucose Cotransport 2 inhibitor pharmaceutical composition, whether the subject has developed a diabetic foot ulcer since receiving their last provision of the gliflozin Sodium-Glucose Cotransport 2 inhibitor pharmaceutical composition.

In some embodiments, e.g., when the gliflozin Sodium-Glucose Cotransport 2 inhibitor pharmaceutical composition includes dapagliflozin, the first plurality of survey results further includes whether the subject has developed bladder cancer since receiving their last provision of the gliflozin Sodium-Glucose Cotransport 2 inhibitor pharmaceutical composition.

In some embodiments, the second survey includes questions that elicit responses providing some or all of the characteristics listed in Table 4. In some embodiments, the second survey includes questions corresponding to each of the survey results required for the methods described herein. In other embodiments, the second survey includes questions corresponding to only a subset of the survey results required for the methods described herein. In such embodiments, other survey results required for the methods described herein are acquired through other means (e.g., upon registration/subscription for a service associated with qualifying the subject for over-the-counter medication, from a healthcare professional, from a prior survey, from a database associated with a pharmacy, etc.) For example, in some embodiments, the subject provides a personal medical identification associated with an insurer, a hospital, or other healthcare professional and information about the subject required for the methods described herein, e.g., one or more survey results, is acquired from a preexisting database associated with the personal medical identification (e.g., a last blood sugar measurement determined for the subject).

TABLE 4

Example characteristics for qualifying a subject for an over-the-counter provision of a gliflozin Sodium-Glucose Cotransport 2 inhibitor pharmaceutical composition

| Result | Example Characteristics |
|---|---|
| 1 | whether the subject is pregnant or breastfeeding |
| 2 | whether the subject has developed ketoacidosis |
| 3 | whether the subject has developed a kidney problem |
| 4 | whether the subject has developed a urinary problem |
| 5 | whether the subject has developed a liver problem |
| 6 | a surgery status of the subject |
| 7 | a dietary status of the subject |
| 8 | whether the subject has developed a pancreatic problem |
| 9 | an alcohol consumption status of the subject, |
| 10 | whether the subject has experienced a yeast infection since receiving their last provision of the gliflozin Sodium-Glucose Cotransport 2 inhibitor pharmaceutical composition |
| 11 | whether the subject has developed hypoglycemia since receiving their last provision of the gliflozin Sodium-Glucose Cotransport 2 inhibitor pharmaceutical composition |
| 12 | whether the subject is experiencing a bodily stress |
| 13 | whether the subject is taking a diabetes medication |
| 14 | a blood sugar level of the subject |
| 15 | whether the subject has experienced a symptom of dehydration since receiving their last provision of the gliflozin Sodium-Glucose Cotransport 2 inhibitor pharmaceutical composition |
| 16 | whether the subject has developed bladder cancer since receiving their last provision of the gliflozin Sodium-Glucose Cotransport 2 inhibitor pharmaceutical composition |
| 17 | whether the subject has developed heart failure since receiving their last provision of the gliflozin Sodium-Glucose Cotransport 2 inhibitor pharmaceutical composition |
| 18 | whether the subject has had a body part amputated since receiving their last provision of the gliflozin Sodium-Glucose Cotransport 2 inhibitor pharmaceutical composition |

TABLE 4-continued

Example characteristics for qualifying a subject for an over-the-counter provision of a gliflozin Sodium-Glucose Cotransport 2 inhibitor pharmaceutical composition

| Result | Example Characteristics |
|---|---|
| 19 | whether the subject has developed leg neuropathy since receiving their last provision of the gliflozin Sodium-Glucose Cotransport 2 inhibitor pharmaceutical composition |
| 20 | whether the subject has developed a diabetic foot ulcer since receiving their last provision of the gliflozin Sodium-Glucose Cotransport 2 inhibitor pharmaceutical composition |
| 21 | whether the subject has hyperkalemia |

It is contemplated that, in some embodiments, any one or more of the survey questions provided in Table 4 will not be included in the second survey (e.g., will not be used for the reassessment). For example, in some embodiments, a characteristic associated with a particular survey questions will be informative when qualifying a subject for one particular gliflozin Sodium-Glucose Cotransport 2 inhibitor but not for another gliflozin Sodium-Glucose Cotransport 2 inhibitor. For instance, a survey question is queried for canagliflozin qualifying surveys but not for ertugliflozin qualifying surveys. The skilled artisan will recognize that different gliflozin Sodium-Glucose Cotransport 2 inhibitor carry different risk and drug interaction profiles. Accordingly, survey information required for qualifying a subject for access to one gliflozin Sodium-Glucose Cotransport 2 inhibitor with a known adverse drug interaction may not be necessary for qualifying the same subject for access to a second gliflozin Sodium-Glucose Cotransport 2 inhibitor.

Accordingly, it is contemplated that the second survey questions elicit responses to any sub-set of survey results provided in Table 4. For brevity, all possible combinations of the characteristics provided in Table 4 are not specifically delineated here. However, the skilled artisan will easily be able to envision any particular subset of survey questions designed to elicit responses to any subset of characteristics provided in Table 4. Likewise, the skilled artisan may know of other survey questions, not provided in Table 4, that may be combined with any subset of the survey questions provided in Table 4 to form the second survey questions used in the methods described herein.

Referring to block 445 of FIG. 4F, all or a portion the results are run against a third plurality of filters of the first category class. When a respective filter in the third plurality of filters is fired (e.g., when a survey result indicates that a triggering condition 218 has been met), the subject is deemed not qualified for the gliflozin Sodium-Glucose Cotransport 2 inhibitor pharmaceutical composition and the method is terminated without delivery of the gliflozin Sodium-Glucose Cotransport 2 inhibitor pharmaceutical composition.

Referring to blocks 445-456 of FIG. 4F-4H, specific filters in the third plurality of filters and their exemplary triggering conditions that cause the corresponding filter to fire are detailed.

In some embodiments, the third plurality of filters of the first category class 214 includes some or all of the filters 216 listed in Table 5. For example, in some embodiments, the first plurality of filters includes 2, 3, 4, 5, 6, or all 7 of the filters listed in Table 5. In one embodiment, the first plurality of filters includes at least filters 1-6 as provided in Table 5.

TABLE 5

Example filters for contraindications associated with re-qualifying a subject for an over-the-counter provision of a gliflozin Sodium-Glucose Cotransport 2 inhibitor pharmaceutical composition

| Filter | Example Criteria |
| --- | --- |
| 1a | a pregnancy filter |
| 2a | a ketoacidosis filter |
| 3a | a kidney problem filter |
| 4a | a urinary problem filter |
| 5a | a bodily stress filter |
| 6a | a diabetes medication filter |
| 7a | a blood sugar status filter |

In one embodiment, the third plurality of filters includes at least filters 1a-6a as provided in Table 5. In another embodiment, the third plurality of filters includes at least filters 1a-7a as provided in Table 5.

It is contemplated that, in some embodiments, any one or more of the filters provided in Table 5 will not be included in the third plurality of filters. For example, in some embodiments, a characteristic associated with a particular survey result will be informative when qualifying a subject for one particular gliflozin Sodium-Glucose Cotransport 2 inhibitor but not for another gliflozin Sodium-Glucose Cotransport 2 inhibitor. Likewise, the skilled artisan may know of other filters, not provided in Table 5, which may be combined with any subset of the filters provided in Table 5 to form the third plurality of filters results used in the methods described herein. For brevity, all possible combinations of the filters provided in Table 5 are not specifically delineated here.

Referring to blocks 446-447, in some embodiments the third plurality of filters includes a pregnancy filter, e.g., as described above in relation to the first pregnancy filter 216-1. In some embodiments, the second pregnancy filter is configured to be fired at least when the first plurality of survey results indicates that the subject is pregnant or the subject is breastfeeding. In some embodiments, the second pregnancy filter is also configured to be fired when the subject is planning on becoming pregnant within a predetermined period of time. When the second pregnancy filter is fired, the subject is not permitted to obtain the gliflozin Sodium-Glucose Cotransport 2 inhibitor pharmaceutical composition over-the-counter (e.g., the method is terminated without authorizing re-provision of the gliflozin Sodium-Glucose Cotransport 2 inhibitor pharmaceutical composition to the subject).

Referring to blocks 448-449, in some embodiments the third plurality of filters includes a ketoacidosis filter. In some embodiments, the ketoacidosis filter is configured to be fired at least when the second plurality of survey results indicates that the subject has developed ketoacidosis since receiving their last provision of the gliflozin Sodium-Glucose Cotransport 2 inhibitor pharmaceutical composition. In some embodiments, the second plurality of survey results indicates that the subject has developed ketoacidosis when the second plurality of survey results indicate that the subject has been diagnosed with ketoacidosis since receiving their last provision of the gliflozin Sodium-Glucose Cotransport 2 inhibitor pharmaceutical composition. In some embodiments, the second plurality of survey results indicates that the subject has developed ketoacidosis when the second plurality of survey results indicate that the subject has experienced a symptom (e.g., a new and/or worsening symptom) of ketoacidosis since receiving their last provision of the gliflozin Sodium-Glucose Cotransport 2 inhibitor pharmaceutical composition, e.g., an increase of ketones in the blood of the subject, an increase of ketones in the urine of the subject, nausea, tiredness, vomiting, trouble breathing, and/or abdominal pain.

Referring to blocks 450-451, in some embodiments the third plurality of filters includes a kidney problem filter. In some embodiments, the kidney problem filter is configured to be fired at least when the second plurality of survey results indicates that the subject has developed a kidney problem since receiving their last provision of the gliflozin Sodium-Glucose Cotransport 2 inhibitor pharmaceutical composition. In some embodiments, the second plurality of survey results indicates that the subject has developed a kidney problem when the survey results indicate that the subject has been diagnosed with a kidney problem since receiving their last provision of the gliflozin Sodium-Glucose Cotransport 2 inhibitor pharmaceutical composition. In some embodiments, the second plurality of survey results indicates that the subject has developed a kidney problem when the survey results indicate that the subject has experienced a symptom (e.g., a new and/or worsening symptom) of a kidney problem, e.g., that the subject is eating less than before, the subject is drinking less than before, vomiting, diarrhea, and/or dehydration.

Referring to blocks 452-453, in some embodiments the third plurality of filters includes a second urinary problem filter, e.g. as described above in relation to the first urinary problem filter 222-2. In some embodiments, the second urinary problem filter is configured to be fired at least when the second plurality of survey results indicates that the subject has experienced symptoms of a urinary tract infection problem since receiving their last provision of the gliflozin Sodium-Glucose Cotransport 2 inhibitor pharmaceutical composition. In some embodiments, a symptom of a urinary problem that is capable of firing the urinary problem filter is selected from the group consisting of a burning sensation when passing urine, an increased urge to urinate, pelvic pain, blood in the urine, fever, back pain, nausea, and vomiting. In some embodiments, the second plurality of survey results indicates that the subject has experienced symptoms of a urinary tract infection when the survey results indicate that the subject has been diagnosed with a urinary tract infection since receiving their last provision of the gliflozin Sodium-Glucose Cotransport 2 inhibitor pharmaceutical composition.

Referring to blocks 454-455, in some embodiments the third plurality of filters includes a bodily stress filter. In some embodiments, the bodily stress filter is configured to be fired at least when the second plurality of survey results indicates that the subject is experiencing a bodily stress. In some embodiments, a bodily stress that is capable of firing the bodily stress filter is selected from the group consisting of fever, a recent trauma, an infection, and a recent surgery.

Referring to block 456 of FIG. 4H, in some embodiments the third plurality of filters includes a second diabetes medication filter, e.g. as described above in relation to the first diabetes medication filter 222-7. In some embodiments, the second diabetes medication filter is configured to be fired at least when the second plurality of survey results indicates that the subject is taking a diabetes medication.

Referring to blocks 457-466 of FIG. 4H-4I, the method also includes running all or a portion of the second survey results against a fourth plurality of filters of the second category class 220-2. When a respective filter in the fourth plurality of filters is fired, the subject is provided with a warning corresponding to the respective filter. In some embodiments, the warning is provided as a next step, e.g., prior to applying survey results to any subsequent filters, after the corresponding filter is fired. For example, with respect to FIGS. 8A-8D, in some embodiments, when the bladder cancer filter is triggered at 818, the device would provide the subject with a warning prior to proceeding to the kidney problem filter at 820, e.g., requiring the subject confirm they have discussed their bladder cancer with a health care professional and the healthcare professional still recommends taking a gliflozin Sodium-Glucose Cotransport 2 inhibitor pharmaceutical composition at 803. In some embodiments the warning is provided after applying survey results to all subsequent filters. For example, in some embodiments, when the alcohol consumption filter is triggered at 832, the device would proceed to the urinary problem filter at 834 prior to transmitting a warning to the subject, and then transmit all warnings corresponding to filters of the second category class, at 844, after survey results have been applied to all subsequent filters.

In some embodiments, the fourth plurality of filters of the second category class 220-2 includes some or all of the filters listed in Table 6. For example, in some embodiments, the fourth plurality of filters includes 2, 3, 4, 5, 6, 7, 8, 9, 10, 11, 12, or all 13 of the filters listed in Table 6.

TABLE 6

Example filters for risk factors associated with re-qualifying a subject for an over-the-counter provision of a gliflozin Sodium-Glucose Cotransport 2 inhibitor pharmaceutical composition

| Filter | Example Criteria |
|---|---|
| 1a | a liver disease filter |
| 2a | a surgery filter |
| 3a | a dietary filter |
| 4a | an alcohol consumption filter |
| 5a | a yeast infection filter |
| 6a | a hypoglycemia symptom filter |
| 7a | a dehydration filter |
| 8a | a bladder cancer filter |
| 9a | a heart failure filter |
| 10a | an amputation filter |
| 11a | a leg neuropathy filter |
| 12a | a diabetic foot ulcer filter |
| 13a | a hyperkalemia filter |

In one embodiment, the fourth plurality of filters includes at least filters 1a-6a as provided in Table 6. It is contemplated that, in some embodiments, any one or more of the filters provided in Table 6 will not be included in the fourth plurality of filters. For example, in some embodiments, a characteristic associated with a particular survey result will be informative when qualifying a subject for one particular gliflozin Sodium-Glucose Cotransport 2 inhibitor pharmaceutical composition but not for another gliflozin Sodium-Glucose Cotransport 2 inhibitor pharmaceutical composition. Accordingly, it is contemplated that the fourth plurality of filters includes any sub-set of filters provided in Table 6. Likewise, the skilled artisan may know of other filters, not provided in Table 6, that may be combined with any subset of the filters 222 provided in Table 6 to form the fourth plurality of filters results used in the methods described herein.

Referring to block 458 of FIG. 4H, in some embodiments, the fourth plurality of filters includes a second liver disease filter, e.g. as described above in relation to the first liver disease filter 222-1. In some embodiments, the second liver disease filter is configured to be fired at least when the second plurality of survey results indicates that the subject has developed a liver problem since receiving their last provision of the gliflozin Sodium-Glucose Cotransport 2 inhibitor pharmaceutical composition. In some embodiments, the second plurality of survey results indicates that the subject has developed a liver problem when the second plurality of survey results indicate that the subject has been diagnosed with a liver problem since receiving their last provision of the gliflozin Sodium-Glucose Cotransport 2 inhibitor pharmaceutical composition.

Referring to block 459, in some embodiments, the fourth plurality of filters includes a second surgery filter, e.g., as described above in relation to the first surgery filter 222-3. In some embodiments, the second surgery filter is configured to be fired at least when the second plurality of survey results indicates that the subject is planning on undergoing surgery.

Referring to block 460, in some embodiments, the fourth plurality of filters includes a second dietary filter, e.g., as described above in relation to the first dietary filter 222-4. In some embodiments, the second dietary filter is configured to be fired at least when the second plurality of survey results indicates that the subject is eating less than they were before receiving their last provision of the gliflozin Sodium-Glucose Cotransport 2 inhibitor pharmaceutical composition.

Referring to block 461, in some embodiments, the fourth plurality of filters includes a second pancreatic disease filter, e.g., as described above in relation to the first pancreatic disease filter 222-5. In some embodiments, the second pancreatic disease filter is configured to be fired at least when the second plurality of survey results indicates that the subject has developed a pancreatic problem since receiving their last provision of the gliflozin Sodium-Glucose Cotransport 2 inhibitor pharmaceutical composition. In some embodiments, the second plurality of survey results indicates that the subject has developed a pancreatic problem when the survey results indicate that the subject has been diagnosed with a pancreatic problem since receiving their last provision of the gliflozin Sodium-Glucose Cotransport 2 inhibitor pharmaceutical composition. In some embodiments, the second plurality of survey results indicates that the subject has developed a pancreatic problem when the survey results indicate that the subject has experienced a symptom (e.g., a new and/or worsening symptom) of a pancreatic problem, e.g., abdominal tenderness and swelling, nausea and vomiting, and/or upper abdominal pain— including pain that radiates to the subject's back.

Referring to block 462, in some embodiments, the fourth plurality of filters includes a second alcohol consumption filter, e.g., as described above in relation to the first alcohol consumption filter 222-6. In some embodiments, the second alcohol consumption filter is configured to be fired at least when the second plurality of survey results indicates that the subject, on average, consumes at least a predetermined number of alcoholic drinks over a predetermined period of time. In some embodiments, the second alcohol consumption filter is configured to be fired at least when the second plurality of survey results indicates that the subject is abusing alcohol.

Referring to blocks 463-464 of FIG. 4I, in some embodiments, the fourth plurality of filters includes a yeast infection filter that is configured to be fired at least when the second plurality of survey results indicates that the subject has experienced a yeast infection since receiving their last provision of the gliflozin Sodium-Glucose Cotransport 2 inhibitor pharmaceutical composition. In some embodiments, the second plurality of survey results indicates that the subject has experienced a yeast infection when the survey results indicate that the subject has been diagnosed with a yeast infection problem since receiving their last provision of the gliflozin Sodium-Glucose Cotransport 2 inhibitor pharmaceutical composition. In some embodiments, the second plurality of survey results indicates that the subject has experienced a yeast infection when the survey results indicate that the subject has experienced a symptom (e.g., a new and/or worsening symptom) of a yeast infection, e.g., a sore throat, an increased urge to urinate, an increased volume of urine, and/or an increased urge to urinate at night.

Referring to blocks 465-466, in some embodiments, the fourth plurality of filters includes a hypoglycemia symptom filter that is configured to be fired at least when the second plurality of survey results indicates that the subject has developed hypoglycemia since receiving their last provision of the gliflozin Sodium-Glucose Cotransport 2 inhibitor pharmaceutical composition. In some embodiments, the second plurality of survey results indicates that the subject has developed hypoglycemia when the survey results indicate that the subject has experienced a symptom (e.g., a new and/or worsening symptom) of hypoglycemia, e.g., shaking, sweating, rapid heartbeat, change in vision, increased hunger, headaches, and/or a change in mood.

Referring to block 467, in some embodiments the method also includes obtaining acknowledgment from the subject for each warning issued to the subject by any filter in the fourth plurality of filters. As described with respect to the warnings issued in conjunction with the second plurality of filters of the second category class, in some embodiments, the warning includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should continue to take the gliflozin Sodium-Glucose Cotransport 2 inhibitor pharmaceutical composition in view of the underlying risk factor. Accordingly, acknowledgement is obtained from the subject when the subject indicates that they have discussed the risk factor underlying the respective filter in the fourth plurality of filters that was fired with a health care professional.

In some embodiments, when a respective filter in the third plurality of filters or fourth plurality of filters is fired, a record associated with the firing of the respective filter is created (e.g., memorializing an adverse event that is required to be reported to a regulatory agency). This record is stored in an adverse event module 242 which includes records of filter firing events associated with a plurality of subjects (e.g., an aggregation of adverse events associated with the gliflozin Sodium-Glucose Cotransport 2 inhibitor pharmaceutical composition across a population of subjects taking the gliflozin Sodium-Glucose Cotransport 2 inhibitor pharmaceutical composition over-the-counter). In some embodiments, an indication the adverse event is communicated to a third party (e.g., a medical practitioner associated with the subject, a health care professional of the subject, and/or a manufacturer/promoter of the gliflozin Sodium-Glucose Cotransport 2 inhibitor pharmaceutical composition). In some embodiments, the indication is automatically stored in the adverse event module 242 when submitted by a subject as part of the second survey.

Referring to block 468 of FIG. 4J, in some embodiments the procedure further includes proceeding with the re-fulfillment process when the re-fulfillment process is not already terminated by the firing of a filter in the third plurality of filters (e.g., the second pregnancy filter). In order for the re-fulfillment process to complete the subject is required to acknowledge each warning associated with each filter 222 in the fourth plurality of filters that was fired.

Referring to block 469, in some embodiments the re-fulfillment process also includes storing an indication in the subject profile 232 of the subject of a re-order for the gliflozin Sodium-Glucose Cotransport 2 inhibitor pharmaceutical composition. The re-fulfillment process further includes communicating an over-the-counter drug facts label 230 for the gliflozin Sodium-Glucose Cotransport 2 inhibitor pharmaceutical composition to the subject. As previously described, the communication of the over-the-counter drug facts label 230 can occur in a variety of means. Upon confirmation from the subject that the over-the-counter drug facts label 230 has been received and read, the method includes authorizing a re-order provision of the gliflozin Sodium-Glucose Cotransport 2 inhibitor pharmaceutical composition to the subject. In some embodiments, this re-order provision includes the destination of the subject.

Figure 8A:
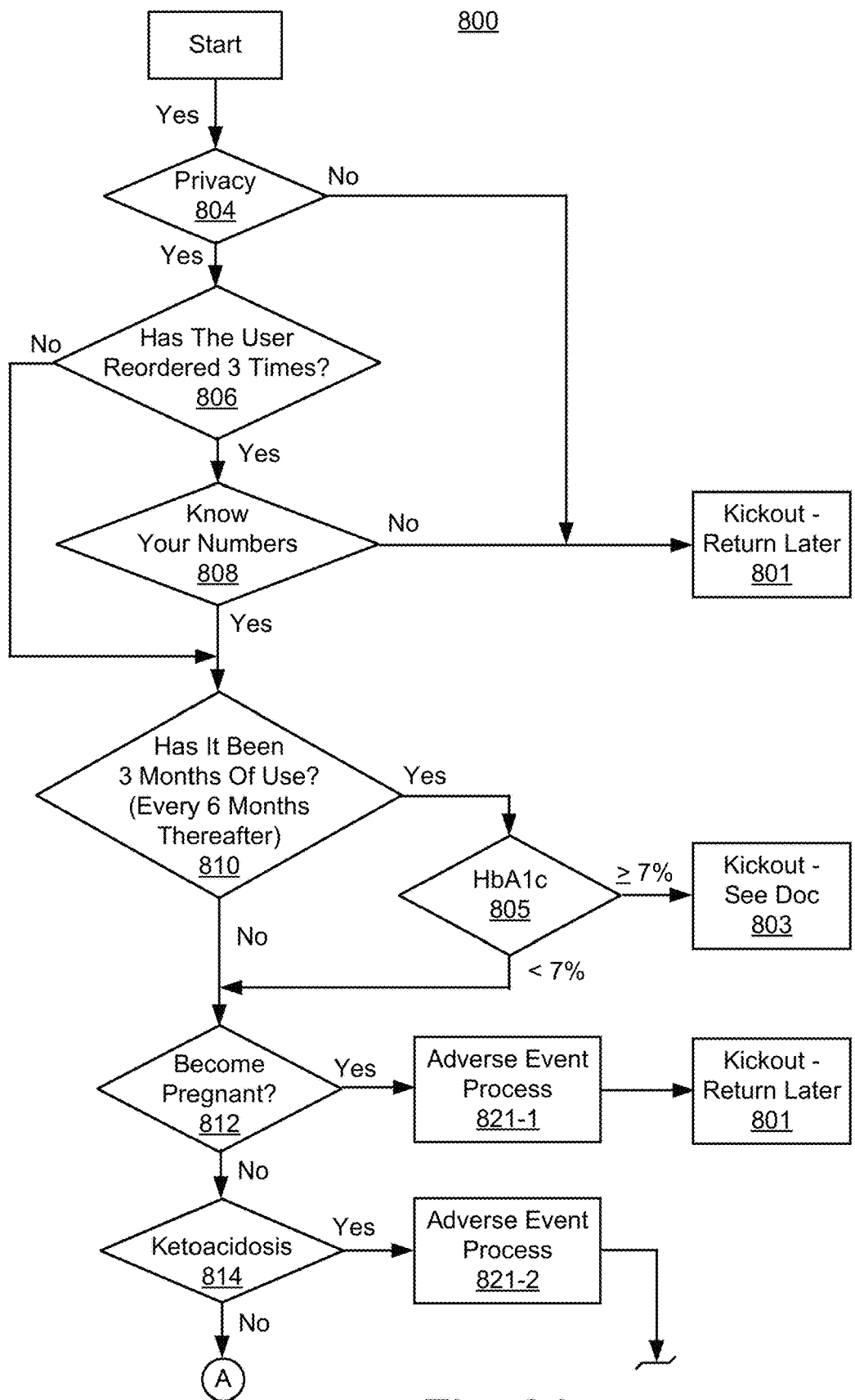
FIGS. 8A, 8B, 8C, and 8D collectively illustrate an example method for qualifying a subject for a refill of an over-the-counter provision of a gliflozin Sodium-Glucose Cotransport 2 inhibitor pharmaceutical composition, in accordance with an embodiment of the present disclosure.
Figure 8B:
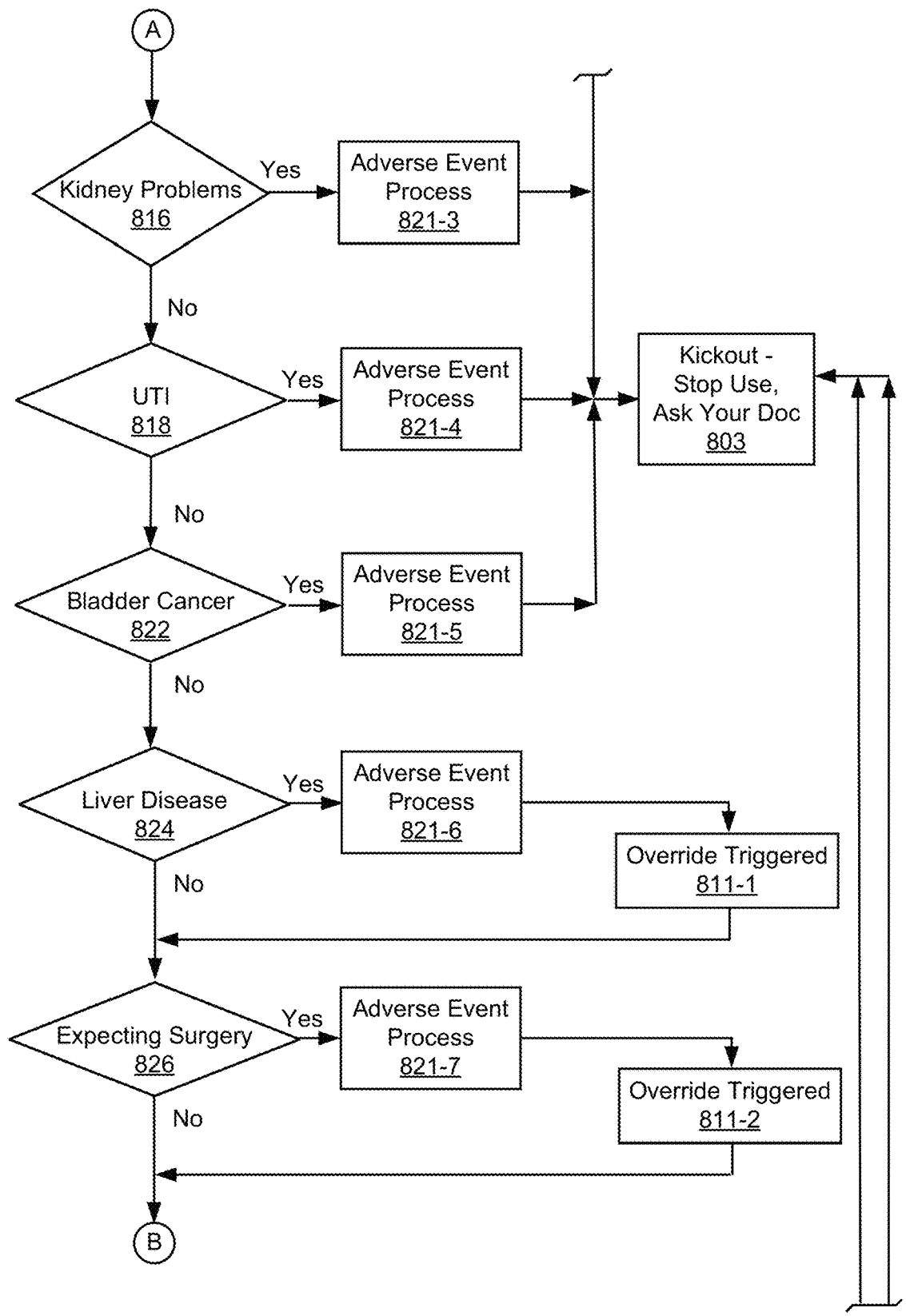
Figure 8C:
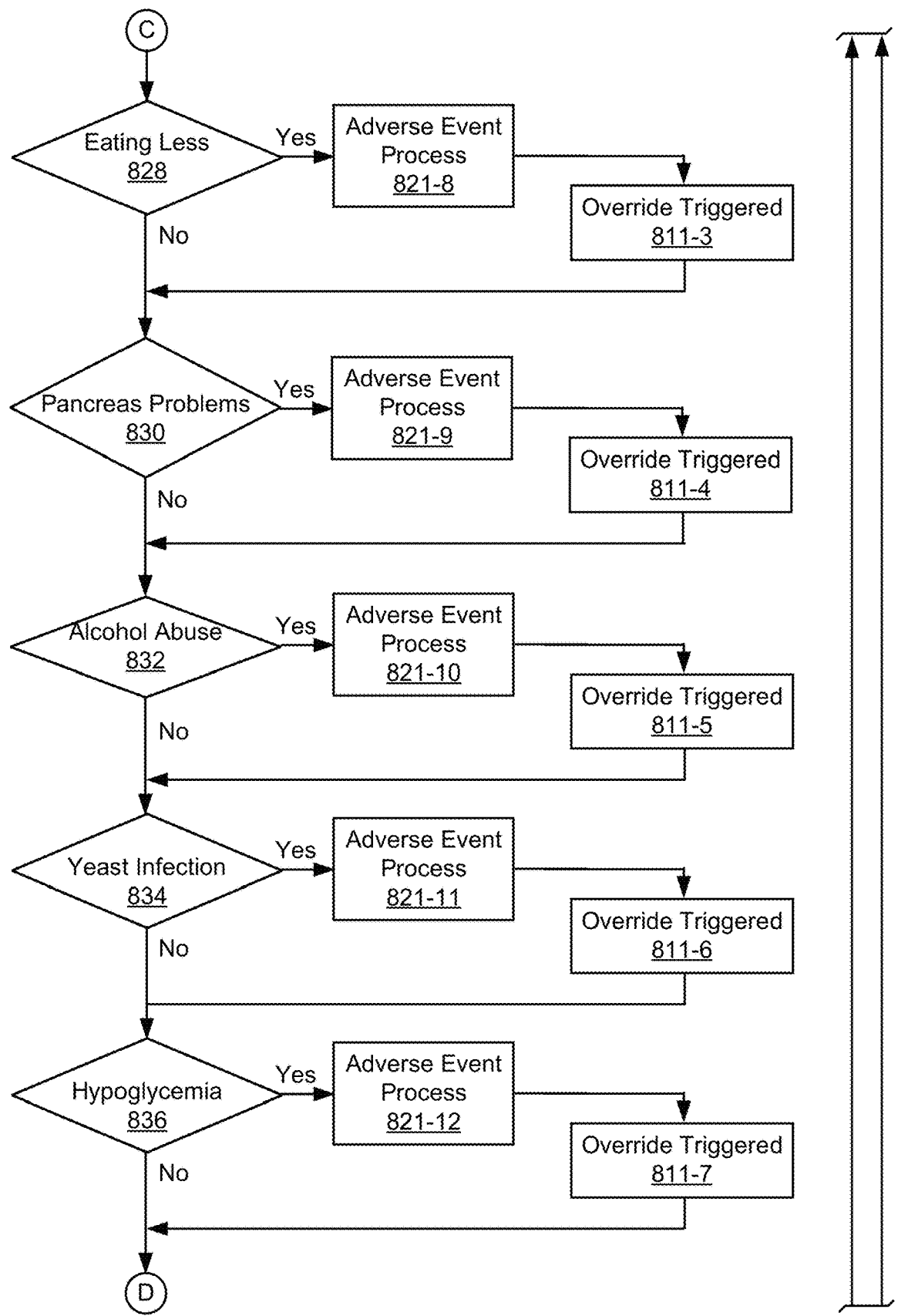
Figure 8D:
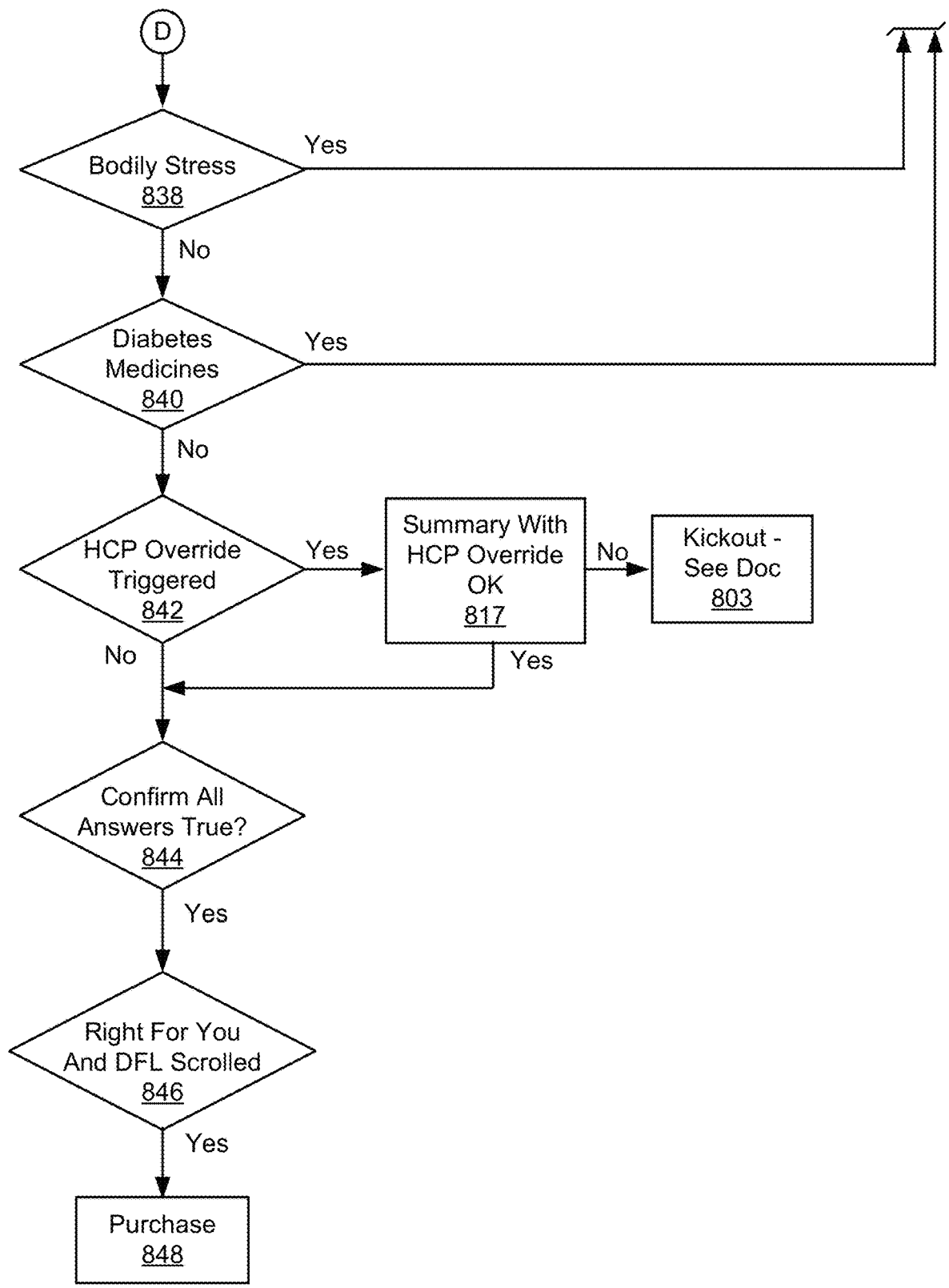

Referring to blocks 470-471, in some embodiments when the subject profile 232 does not include a recent blood sugar status for the subject (e.g., a blood sugar status obtained within three months after the subject's first order, or within six months thereafter, e.g., as illustrated at 810 in FIG. 8A), the re-fulfillment process also includes obtaining in the second plurality of survey results a blood sugar status of the subject and further including in the third plurality of filters a second blood sugar filter, e.g., as described above in relation to the first blood sugar status of the subject 216-6. In some embodiments, the second blood sugar status is configured to be fired at least when the second plurality of survey results indicates that the subject has a blood sugar level of at least a second ceiling blood sugar level. In some embodiments, the second ceiling blood sugar level used in the second blood sugar filter is a value selected from 6.5% to 7.5% glycated hemoglobin. In some embodiments, the second ceiling blood sugar level used in the second blood sugar filter is 7% glycated hemoglobin.

Referring to blocks 472-473, in some embodiments the re-fulfillment process also includes obtaining in the second plurality of survey results a blood sugar status of the subject and further including in the third plurality of filters a second blood sugar filter, e.g., as described above in relation to the first blood sugar status of the subject 216-6. In some embodiments, the second blood sugar status is configured to be fired at least when the second plurality of survey results indicates that the subject has a blood sugar level of at least a second ceiling blood sugar level. In some embodiments, the second ceiling blood sugar level used in the second blood sugar filter is a value selected from 6.5% to 7.5% glycated hemoglobin. In some embodiments, the second ceiling blood sugar level used in the second blood sugar filter is 7% glycated hemoglobin.

Referring to block 474, in some embodiments the second plurality of survey results further includes whether the subject has experienced a symptom of dehydration since receiving their last provision of the gliflozin Sodium-Glucose Cotransport 2 inhibitor pharmaceutical composition. In some embodiments the fourth plurality of filters further includes a dehydration filter that is fired at least when the second plurality of survey results indicates that the subject has experienced a symptom of dehydration since receiving their last provision of the gliflozin Sodium-Glucose Cotransport 2 inhibitor pharmaceutical composition. In some embodiments, a symptom of dehydration that is capable of firing the dehydration filter is selected from the group consisting of dizziness, faintness, light-headedness, and weakness.

Referring to block 475 of FIG. 4K, in some embodiments, e.g., where the gliflozin Sodium-Glucose Cotransport 2 inhibitor pharmaceutical composition includes dapagliflozin, the second plurality of survey results further includes a bladder cancer status of the subject and, accordingly, the third plurality of filters further includes a second bladder cancer filter that is fired at least when the second plurality of survey results indicates that the subject has developed bladder cancer since receiving their last provision of the gliflozin Sodium-Glucose Cotransport 2 inhibitor pharmaceutical composition.

FIG. 7 illustrates an example method (700) (e.g., performed at an electric device) for qualifying a subject for an over-the-counter gliflozin Sodium-Glucose Cotransport 2 inhibitor pharmaceutical composition. In some embodiments, the method of FIG. 7 is utilized when the subject has not been previously qualified for the medication. In some embodiments, the method of FIG. 7 is utilized when the subject was previously qualified for the gliflozin Sodium-Glucose Cotransport 2 inhibitor pharmaceutical composition but a predetermined period of time elapsed since the previous qualification occurred (e.g., the most recent qualification of the subject was greater than one year ago).

Referring to FIG. 7, the device prompts (702) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the device prompts (704) the user to confirm that they know their blood sugar levels (e.g., because the subject must know their blood values in order to complete the qualification process). If the subject indicates they do not know their blood sugar level, the process terminates 701 without authorizing provision of the gliflozin Sodium-Glucose Cotransport 2 inhibitor pharmaceutical agent, and optionally transmits advice to the user to return later, e.g., once they know their blood sugar levels. In some embodiments, the device does not prompt the user to confirm they know their numbers, but includes a selection for indicating they don't know a value when asking the subject for a particular value. If the subject indicates they know their blood sugar levels, the process continues.

The device prompts the subject to provide information about their pregnancy status and then applies (706) the answer received from the subject to a pregnancy filter. When the pregnancy filter is fired (e.g., when the answer indicates the subject is pregnant, breastfeeding, or planning to become pregnant), the device terminates (703) the qualification process without authorizing provision of the gliflozin Sodium-Glucose Cotransport 2 inhibitor pharmaceutical agent and, optionally, transmits advice to the user as to why they should not take the gliflozin Sodium-Glucose Cotransport 2 inhibitor pharmaceutical agent.

When the pregnancy filter is not fired, the device proceeds with the qualification process, prompting the subject to indicate whether they have type 1 diabetes and then applies (708) the answer received from the subject to a type 1 diabetes filter. When the type 1 diabetes filter is fired (e.g., when the answer indicates the subject has type 1 diabetes), the device terminates (703) the qualification process without authorizing provision of the gliflozin Sodium-Glucose Cotransport 2 inhibitor pharmaceutical agent and, optionally, transmits advice to the user as to why they should not take the gliflozin Sodium-Glucose Cotransport 2 inhibitor pharmaceutical agent.

When the type 1 diabetes filter is not fired, the device proceeds with the qualification process, prompting the subject to provide their ketoacidosis status and then applies (710) the answer received from the subject to a ketoacidosis filter. When the ketoacidosis filter is fired (e.g., when the answer indicates the subject has ketoacidosis), the device terminates (703) the qualification process without authorizing provision of the gliflozin Sodium-Glucose Cotransport 2 inhibitor pharmaceutical agent and, optionally, transmits advice to the user as to why they should not take the gliflozin Sodium-Glucose Cotransport 2 inhibitor pharmaceutical agent.

When the ketoacidosis filter is not fired, the device proceeds with the qualification process, prompting the subject to indicate whether they have kidney disease (712). When the kidney disease filter is fired (e.g., when the answer to the prompt indicates the subject has kidney disease), the device terminates (703) the qualification process without authorizing provision of the gliflozin Sodium-Glucose Cotransport 2 inhibitor pharmaceutical agent and, optionally, transmits advice to the user as to why they should not take the gliflozin Sodium-Glucose Cotransport 2 inhibitor pharmaceutical agent.

When the kidney disease filter is not fired, the device proceeds with the qualification process, prompting the subject to indicate whether they have bladder cancer and then applies (714) the answer received from the subject to a bladder cancer filter. When the bladder cancer filter is fired (e.g., when the answer to the prompt indicates the subject has bladder cancer), the device terminates (703) the qualification process without authorizing provision of the gliflozin Sodium-Glucose Cotransport 2 inhibitor pharmaceutical agent and, optionally, transmits advice to the user as to why they should not take the gliflozin Sodium-Glucose Cotransport 2 inhibitor pharmaceutical agent.

When the bladder cancer filter is not fired, the device proceeds with the qualification process, prompting the subject to indicate their age and then applies (716) the answer received from the subject to an age filter. When the age filter is fired (e.g., when the answer indicates the subject is less than eighteen years old), the device terminates (703) the qualification process without authorizing provision of the gliflozin Sodium-Glucose Cotransport 2 inhibitor pharmaceutical agent and, optionally, transmits advice to the user as to why they should not take the gliflozin Sodium-Glucose Cotransport 2 inhibitor pharmaceutical agent and/or to return once they have obtained an age at which it would be appropriate to take a gliflozin Sodium-Glucose Cotransport 2 inhibitor pharmaceutical agent.

The device proceeds with the qualification process, prompting the subject to provide information about their blood sugar level and then applies (718) the answer received from the subject to a blood sugar filter. When the blood sugar filter is fired (e.g., when the answer indicates the subject has a blood sugar level that is either below a floor blood sugar level or above a first ceiling blood sugar level), the process terminates (701) without authorizing provision of the gliflozin Sodium-Glucose Cotransport 2 inhibitor pharmaceutical agent and, optionally, transmits advice to the user to return later when their blood sugar level is within the floor and ceiling levels.

The device proceeds with the qualification process, prompting the subject to indicate whether they have liver disease and then applies (720) the answer received from the subject to a first liver disease filter. When the first liver disease filter is fired (e.g., when the answer indicates the subject has liver disease), an override procedure (711-1) is initiated (e.g., the device creates a record indicating that the user must confirm they have discussed taking a gliflozin Sodium-Glucose Cotransport 2 inhibitor pharmaceutical composition with a health care professional).

The device proceeds with the qualification process, prompting the subject to indicate whether they have a urinary problem and then applies (722) the answer received from the subject to a first urinary problem filter. When the first urinary problem filter is fired (e.g., when the answer indicates the subject has a urinary problem), an override procedure (711-2) is initiated (e.g., the device creates a record indicating that the user must confirm they have discussed taking a gliflozin Sodium-Glucose Cotransport 2 inhibitor pharmaceutical composition with a health care professional).

The device proceeds with the qualification process, prompting the subject to indicate their surgery status and then applies (724) the answer received from the subject to a first surgery filter. When the first surgery filter is fired (e.g., when the answer indicates the subject is planning to undergo surgery), an override procedure (711-3) is initiated (e.g., the device creates a record indicating that the user must confirm they have discussed taking a gliflozin Sodium-Glucose Cotransport 2 inhibitor pharmaceutical composition with a health care professional).

The device proceeds with the qualification process, prompting the subject to indicate their dietary status and then applies (726) the answer received from the subject to a first dietary filter. When the first dietary filter is fired (e.g., when the answer indicates the subject has recently been eating less due to illness, surgery, or a change in diet), an override procedure (711-4) is initiated (e.g., the device creates a record indicating that the user must confirm they have discussed taking a gliflozin Sodium-Glucose Cotransport 2 inhibitor pharmaceutical composition with a health care professional).

The device proceeds with the qualification process, prompting the subject to indicate whether they have ever had a pancreatic problem and then applies (728) the answer received from the subject to a first pancreatic disease filter. When the first pancreatic disease filter is fired (e.g., when the answer indicates the subject has had a pancreatic problem), an override procedure (711-5) is initiated (e.g., the device creates a record indicating that the user must confirm they have discussed taking a gliflozin Sodium-Glucose Cotransport 2 inhibitor pharmaceutical composition with a health care professional).

The device proceeds with the qualification process, prompting the subject to indicate their alcohol consumption status and then applies (730) the answer received from the subject to a first alcohol consumption filter. When the first alcohol consumption disease filter is fired (e.g., when the answer indicates the subject abuses alcohol), an override procedure (711-6) is initiated (e.g., the device creates a record indicating that the user must confirm they have discussed taking a gliflozin Sodium-Glucose Cotransport 2 inhibitor pharmaceutical composition with a health care professional).

The device proceeds with the qualification process, prompting the subject to indicate whether they are taking a diabetes medication and then applies (732) the answer received from the subject to a first diabetes medication filter. When the first diabetes medication filter is fired (e.g., when the answer indicates the subject is taking a diabetes medication), an override procedure (711-7) is initiated (e.g., the device creates a record indicating that the user must confirm they have discussed taking a gliflozin Sodium-Glucose Cotransport 2 inhibitor pharmaceutical composition with a health care professional).

The device proceeds with the qualification process, determining (734) whether the override procedure has been triggered (e.g., by firing of any one of the first liver disease filter, the first urinary problem filter, the first surgery filter, the first dietary filter, the first pancreatic disease filter, the first alcohol consumption filter, or the first diabetes medication filter). If the override procedure has been triggered, the device prompts (717) the user to confirm that they have spoken with a medical professional about taking a gliflozin Sodium-Glucose Cotransport 2 inhibitor pharmaceutical composition (e.g., in view of the underlying risk factor that triggered the first liver disease filter, first urinary problem filter, first surgery filter, first dietary filter, first pancreatic disease filter, first alcohol consumption filter, and/or first diabetes medication filter) and the medical professional recommended taking the gliflozin Sodium-Glucose Cotransport 2 inhibitor pharmaceutical composition. If the user's responses indicate they have not spoken with a medical professional or the medical professional did not recommend taking the gliflozin Sodium-Glucose Cotransport 2 inhibitor pharmaceutical composition, the device terminates (705) the process and, optionally, transmits advice for the subject to consult a medical professional.

If the override procedure was not triggered, or the override procedure was triggered and the subject's response (717) indicated that a medical professional recommended they take a gliflozin Sodium-Glucose Cotransport 2 inhibitor pharmaceutical composition (e.g., in view of the underlying risk factor triggering the override procedure), the device proceeds with the qualification process, prompting (736) the subject to confirm their answers. If the user confirms their answers, the device transmits (738) a drug facts label for the gliflozin Sodium-Glucose Cotransport 2 inhibitor pharmaceutical composition and prompts the user to read the drug facts label. If the subject confirms they have read the drug facts label (e.g., the subject scrolls through the drug facts label), the device proceeds to authorize (740) purchase of the gliflozin Sodium-Glucose Cotransport 2 inhibitor pharmaceutical composition.

FIG. 8 illustrates an example method (800) for qualifying a subject for a refill of an over-the-counter gliflozin Sodium-Glucose Cotransport 2 inhibitor pharmaceutical composition (e.g., following a prescription from a medical professional or initial qualification by a method described herein). Referring to FIG. 8, the device prompts (802) the subject to acknowledge a privacy notice. Once the subject has acknowledged they have the requisite privacy for continuing, the device determines (806) whether the user (e.g., the subject) has already reordered the over-the-counter gliflozin Sodium-Glucose Cotransport 2 inhibitor pharmaceutical composition three previous times. When the device determines that the subject has reordered the over-the-counter gliflozin Sodium-Glucose Cotransport 2 inhibitor pharmaceutical composition three previous times, the device prompts (808) the user to confirm that they know their blood sugar levels (e.g., because the subject must know their blood values in order to complete the re-qualification process). If the subject indicates they do not know their blood sugar level, the process terminates 801 without authorizing provision of the gliflozin Sodium-Glucose Cotransport 2 inhibitor pharmaceutical agent, and optionally transmits advice to the user to return later, e.g., once they know their blood sugar levels.

If the device determines the subject has not reordered the over-the-counter gliflozin Sodium-Glucose Cotransport 2 inhibitor pharmaceutical composition three previous times, or if the subject indicates they know their blood sugar levels, the device determines whether a blood sugar level has been checked within a predetermined period of time (e.g., within three months of an initial order or within six months thereafter). When a new blood sugar input is required (e.g., when the subject's profile does not include a record of the subject's blood sugar taken within the past three months (and every six months thereafter, e.g., for a subsequent reorder process)), the device proceeds with the process, prompting the user to indicate whether their blood sugar is below a threshold target level (e.g., 7% glycated hemoglobin) and applies (805) the answer received from the subject to a blood sugar filter. When the blood sugar filter is fired (e.g., when the answer indicates the subject has a blood sugar not below the target level, e.g., 7% glycated hemoglobin), the device terminates (803) the qualification process, optionally transmitting advice for the subject to discuss taking a prescription-strength gliflozin Sodium-Glucose Cotransport 2 inhibitor pharmaceutical agent with a medical professional.

When the blood sugar filter is not fired, the device prompts the subject to provide information about their pregnancy status and then applies (812) the answer received from the subject to a pregnancy filter. When the pregnancy filter is fired (e.g., when the answer indicates the subject is pregnant, breastfeeding, or planning to become pregnant), the device creates (821-1) a record of an adverse event (e.g., aggregated in an adverse event data store having records of adverse events from a plurality of users), terminates (801) the qualification process and, optionally, transmits advice to the user as to why they should not take the gliflozin Sodium-Glucose Cotransport 2 inhibitor pharmaceutical composition and/or to return once they are not pregnant, breastfeeding, or planning on becoming pregnant.

When the pregnancy filter is not fired, the device proceeds with the qualification process, prompting the subject to provide information indicating whether they have developed ketoacidosis and applies (814) the answer to a ketoacidosis symptom filter. When the ketoacidosis symptom filter is fired (e.g., when the subject's answer indicates the subject has developed ketoacidosis since receiving their last provision of the gliflozin Sodium-Glucose Cotransport 2 inhibitor pharmaceutical composition), the device creates (821-2) a record of an adverse event (e.g., aggregated in an adverse event data store having records of adverse events from a plurality of users) and the device terminates (803) the qualification process, optionally transmitting advice for the subject to discuss taking a gliflozin Sodium-Glucose Cotransport 2 inhibitor pharmaceutical agent with a medical professional.

When the ketoacidosis symptom filter is not fired, the device proceeds with the qualification process, prompting the subject to provide information indicating whether they have developed a kidney problem and applies (816) the answer to a kidney problem filter. When the kidney problem filter is fired (e.g., when the subject's answer indicates the subject has developed a kidney problem symptom since receiving their last provision of the gliflozin Sodium-Glucose Cotransport 2 inhibitor pharmaceutical composition), the device creates (821-3) a record of an adverse event (e.g., aggregated in an adverse event data store having records of adverse events from a plurality of users) and the device terminates (803) the qualification process, optionally transmitting advice for the subject to discuss taking a gliflozin Sodium-Glucose Cotransport 2 inhibitor pharmaceutical agent with a medical professional.

When the kidney problem filter is not fired, the device proceeds with the qualification process, prompting the subject to provide information indicating whether they have developed a urinary problem and applies (818) the answer to a second urinary problem filter. When the second urinary problem filter is fired (e.g., when the subject's answer indicates the subject has developed a symptom of a urinary problem since receiving their last provision of the gliflozin Sodium-Glucose Cotransport 2 inhibitor pharmaceutical composition), the device creates (821-4) a record of an adverse event (e.g., aggregated in an adverse event data store having records of adverse events from a plurality of users) and the device terminates (803) the qualification process, optionally transmitting advice for the subject to discuss taking a gliflozin Sodium-Glucose Cotransport 2 inhibitor pharmaceutical agent with a medical professional.

When the second urinary problem filter is not fired, the device proceeds with the qualification process, prompting the subject to provide information indicating whether they have developed bladder cancer and applies (822) the answer to a bladder cancer filter. When the bladder cancer filter is fired (e.g., when the subject's answer indicates the subject has developed bladder cancer since receiving their last provision of the gliflozin Sodium-Glucose Cotransport 2 inhibitor pharmaceutical composition), the device creates (821-5) a record of an adverse event (e.g., aggregated in an adverse event data store having records of adverse events from a plurality of users) and the device terminates (803) the qualification process, optionally transmitting advice for the subject to discuss taking a gliflozin Sodium-Glucose Cotransport 2 inhibitor pharmaceutical agent with a medical professional.

When the bladder cancer filter is not fired, the device proceeds with the qualification process, prompting the subject to provide information indicating whether they have developed a liver problem and then applies (824) the answer received from the subject to a second liver disease filter. When the second liver disease filter is fired (e.g., when the answer indicates the subject has developed a liver problem since receiving their last provision of the gliflozin Sodium-Glucose Cotransport 2 inhibitor pharmaceutical composition), the device creates (821-6) a record of an adverse event (e.g., aggregated in an adverse event data store having records of adverse events from a plurality of users) and initiates (811-1) an override procedure (e.g., creates a record indicating that the user must confirm they have discussed taking a gliflozin Sodium-Glucose Cotransport 2 inhibitor pharmaceutical composition with a health care professional).

The device proceeds with the qualification process, prompting the subject to indicate whether they are planning on undergoing surgery and then applies (826) the answer received from the subject to a second surgery filter. When the second surgery filter is fired (e.g., when the answer indicates the subject is planning on undergoing surgery), the device creates (821-7) a record of an adverse event (e.g., aggregated in an adverse event data store having records of adverse events from a plurality of users) and initiates (811-2) an override procedure (e.g., creates a record indicating that the user must confirm they have discussed taking a gliflozin Sodium-Glucose Cotransport 2 inhibitor pharmaceutical composition with a health care professional).

The device proceeds with the qualification process, prompting the subject to indicate whether they are eating less and then applies (828) the answer received from the subject to a second dietary filter. When the second dietary filter is fired (e.g., when the answer indicates the subject is eating less since receiving their last provision of the gliflozin Sodium-Glucose Cotransport 2 inhibitor pharmaceutical composition), the device creates (821-8) a record of an adverse event (e.g., aggregated in an adverse event data store having records of adverse events from a plurality of users) and initiates (811-3) an override procedure (e.g., creates a record indicating that the user must confirm they have discussed taking a gliflozin Sodium-Glucose Cotransport 2 inhibitor pharmaceutical composition with a health care professional).

The device proceeds with the qualification process, prompting the subject to provide information indicating whether they have developed a pancreatic problem and then applies (830) the answer received from the subject to a second pancreatic disease filter. When the second pancreatic disease filter is fired (e.g., when the answer indicates the subject has developed a pancreatic problem since receiving their last provision of the gliflozin Sodium-Glucose Cotransport 2 inhibitor pharmaceutical composition), the device creates (821-9) a record of an adverse event (e.g., aggregated in an adverse event data store having records of adverse events from a plurality of users) and initiates (811-4) an override procedure (e.g., creates a record indicating that the user must confirm they have discussed taking a gliflozin Sodium-Glucose Cotransport 2 inhibitor pharmaceutical composition with a health care professional).

The device proceeds with the qualification process, prompting the subject to indicate their alcohol consumption status and then applies (832) the answer received from the subject to a second alcohol consumption filter. When the second alcohol consumption filter is fired (e.g., when the answer indicates the subject has begun abusing alcohol), the device creates (821-10) a record of an adverse event (e.g., aggregated in an adverse event data store having records of adverse events from a plurality of users) and initiates (811-5) an override procedure (e.g., creates a record indicating that the user must confirm they have discussed taking a gliflozin Sodium-Glucose Cotransport 2 inhibitor pharmaceutical composition with a health care professional).

The device proceeds with the qualification process, prompting the subject to providing information indicating whether they have experienced a yeast infection and then applies (834) the answer received from the subject to a yeast infection filter. When the yeast infection filter is fired (e.g., when the answer indicates the subject has experienced a yeast infection since receiving their last provision of the gliflozin Sodium-Glucose Cotransport 2 inhibitor pharmaceutical composition), the device creates (821-11) a record of an adverse event (e.g., aggregated in an adverse event data store having records of adverse events from a plurality of users) and initiates (811-6) an override procedure (e.g., creates a record indicating that the user must confirm they have discussed taking a gliflozin Sodium-Glucose Cotransport 2 inhibitor pharmaceutical composition with a health care professional).

The device proceeds with the qualification process, prompting the subject to provide information indicating whether they have developed hypoglycemia and then applies (836) the answer received from the subject to a hypoglycemia symptom filter. When the hypoglycemia symptom filter is fired (e.g., when the answer indicates the subject has developed hypoglycemia since receiving their last provision of the gliflozin Sodium-Glucose Cotransport 2 inhibitor pharmaceutical composition), the device creates (821-12) a record of an adverse event (e.g., aggregated in an adverse event data store having records of adverse events from a plurality of users) and initiates (811-7) an override procedure (e.g., creates a record indicating that the user must confirm they have discussed taking a gliflozin Sodium-Glucose Cotransport 2 inhibitor pharmaceutical composition with a health care professional).

The device proceeds with the qualification process, prompting the subject to indicate whether they are experiencing a bodily stress and then applies (838) the answer received from the subject to a bodily stress filter. When the bodily stress filter is fired (e.g., when the answer indicates the subject is experiencing a bodily stress, such as fever, trauma, or infection), the device terminates (803) the qualification process, optionally transmitting advice for the subject to discuss taking a gliflozin Sodium-Glucose Cotransport 2 inhibitor pharmaceutical agent with a medical professional.

When the bodily stress filter is not fired the device proceeds with the qualification process, prompting the subject to indicate whether they taking a diabetes medication and then applies (840) the answer received from the subject to a diabetes medication filter. When the diabetes medication filter is fired (e.g., when the answer indicates the subject is taking diabetes medication), the device terminates (803) the qualification process, optionally transmitting advice for the subject to discuss taking a gliflozin Sodium-Glucose Cotransport 2 inhibitor pharmaceutical agent with a medical professional.

The device proceeds with the qualification process, determining (842) whether the override procedure has been triggered (e.g., by firing of any one of the second liver disease filter, the second surgery filter, the second dietary filter, the second pancreatic disease filter, the second alcohol consumption filter, the yeast infection filter, or the hypoglycemia symptom filter). If the override procedure has been triggered, the device prompts (817) the user to confirm that they have spoken with a medical professional about taking a gliflozin Sodium-Glucose Cotransport 2 inhibitor pharmaceutical composition (e.g., in view of the underlying risk factor that triggered the second liver disease filter, the second surgery filter, the second dietary filter, the second pancreatic disease filter, the second alcohol consumption filter, the yeast infection filter, and/or the hypoglycemia symptom filter) and the medical professional recommended taking the gliflozin Sodium-Glucose Cotransport 2 inhibitor pharmaceutical composition. If the user's response indicates they have not spoken with a medical professional or the medical professional did not recommend taking the gliflozin Sodium-Glucose Cotransport 2 inhibitor pharmaceutical composition, the device terminates (803) the process and, optionally, transmits advice for the subject to consult a medical professional.

If the override procedure was not triggered, or the override procedure was triggered and the subject's response (817) indicated that a medical professional recommended they take a gliflozin Sodium-Glucose Cotransport 2 inhibitor pharmaceutical composition (e.g., in view of the underlying risk factor triggering the override procedure), the device proceeds with the re-qualification process, prompting (844) the subject to confirm their answers. If the user confirms their answers, the device transmits (846) a drug facts label for the gliflozin Sodium-Glucose Cotransport 2 inhibitor pharmaceutical composition and prompts the user to read the drug facts label. If the subject confirms they have read the drug facts label, the device proceeds to authorize purchase of the gliflozin Sodium-Glucose Cotransport 2 inhibitor pharmaceutical composition.

SPECIFIC EMBODIMENTS

In one aspect, the disclosure provides methods, software, and computer systems for qualifying a human subject for over-the-counter delivery of a gliflozin Sodium-Glucose Cotransport 2 inhibitor pharmaceutical composition for lower blood sugar, e.g., thereby treating Type 2 diabetes and/or maintaining sub-diabetic blood sugar levels. In one embodiment, a computer system (e.g., computer system 250 in FIG. 2) includes instructions for conducting a survey of the subject (e.g., including survey questions 208 and 212 administered via assessment module 252 in FIG. 2) to obtain information about the subject necessary to run against at least two series of filters (e.g., filters 216 and 222 in first filter category class 214-1 and second filter category class 220-1, respectively, in FIG. 2). The computer system also includes instructions for running the survey results against the filters. Filters 216 in the first series of filters 214 prevent authorization of a provision of the OTC gliflozin Sodium-Glucose Cotransport 2 inhibitor where the subject's survey results identify a contraindication for the OTC gliflozin Sodium-Glucose Cotransport 2 inhibitor. Filters 222 in the second series of filters 220 generate a warning 226 where the subject's survey results identify a risk factor for the OTC gliflozin Sodium-Glucose Cotransport 2 inhibitor. In some embodiments, the warning 226 includes a prompt requiring the subject to confirm they have discussed the risk factor with a physician in order to proceed with qualification for the OTC gliflozin Sodium-Glucose Cotransport 2 inhibitor.

In one aspect, the disclosure provides methods, software, and computer systems for re-qualifying a human subject for over-the-counter delivery of a gliflozin Sodium-Glucose Cotransport 2 inhibitor pharmaceutical composition for lower blood sugar, e.g., thereby treating Type 2 diabetes and/or maintaining sub-diabetic blood sugar levels. In one embodiment, a computer system (e.g., computer system 250 in FIG. 2) includes instructions for conducting a survey of the subject (e.g., administered via reassessment module 254 in FIG. 2) to obtain information about the subject necessary to run against at least two series of filters. The computer system also includes instructions for running the survey results against the filters. Filters 216 in the third series of filters 214-2 prevent authorization for delivery of the OTC gliflozin Sodium-Glucose Cotransport 2 inhibitor where the subject's survey results identify a contraindication for the OTC gliflozin Sodium-Glucose Cotransport 2 inhibitor. Filters 222 in the fourth series of filters 220-2 generate a warning 226 where the subject's survey results identify a risk factor for the OTC gliflozin Sodium-Glucose Cotransport 2 inhibitor. In some embodiments, the warning 226 includes a prompt requiring the subject to confirm they have discussed the risk factor with a physician in order to proceed with qualification for the OTC gliflozin Sodium-Glucose Cotransport 2 inhibitor.

In one aspect, the disclosure provides a computer system for qualifying a human subject for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels. The computer system comprising one or more processors and a memory, the memory comprising non-transitory instructions which, when executed by the one or more processor, perform a method for qualifying a human subject for over-the-counter delivery of the gliflozin Sodium-Glucose Cotransport 2 inhibitor pharmaceutical composition. The method includes conducting a first survey of the subject thereby obtaining a first plurality of survey results necessary to run against a first plurality of filters of a first category class and a second plurality of filters of a second category class. The method then includes running all or a portion of the first plurality of survey results against a first plurality of filters of a first category class, wherein, when a respective filter in the first plurality of filters is fired, the subject is deemed not qualified for delivery of the gliflozin Sodium-Glucose Cotransport 2 inhibitor pharmaceutical composition and the method is terminated without delivery of the gliflozin Sodium-Glucose Cotransport 2 inhibitor pharmaceutical composition to the subject. The method then includes running all or a portion of the first plurality of survey results against a second plurality of filters of a second category class, wherein, when a respective filter in the second plurality of filters is fired, the subject is provided with a warning corresponding to the respective filter. The method also includes obtaining acknowledgment from the subject for the warning issued to the subject by any filter in the second plurality of filters. The method also includes proceeding with a fulfillment process when no filter in the first plurality of filters has been fired and the subject has acknowledged each warning associated with each filter in the second plurality of filters that was fired. The fulfillment process includes: storing an indication in a subject profile of an initial order for the gliflozin Sodium-Glucose Cotransport 2 inhibitor pharmaceutical composition, communicating an over-the-counter drug facts label for the gliflozin Sodium-Glucose Cotransport 2 inhibitor pharmaceutical composition to the subject, and authorizing, upon confirmation from the subject that the over-the-counter drug facts label has been received and read, provision of the gliflozin Sodium-Glucose Cotransport 2 inhibitor pharmaceutical composition to the subject. In some embodiments, the authorization includes a destination associated with the subject.

In some embodiments, the first plurality of survey results indicates a plurality of survey results selected from the survey results listed in Table 1. In one embodiment, the first plurality of survey results indicates: whether the subject is one of (i) pregnant, (ii) breastfeeding, or (iii) planning to become pregnant, a Type 1 diabetes status of the subject, a ketoacidosis status of the subject, a kidney disease status of the subject, an age of the subject, a blood sugar level of the subject, whether the subject has a liver problem, whether the subject has ever had a urinary problem, a surgery status of the subject, a dietary status of the subject, whether the subject has ever had a pancreatic problem, an alcohol consumption status of the subject, and whether the subject is taking a diabetes medication.

In some embodiments, the first plurality of filters includes a plurality of filters selected from the filters listed in Table 2. In one embodiment, the first plurality of filters includes a first pregnancy filter, a Type 1 diabetes, a ketoacidosis filter, a first kidney disease filter, an age filter, and a first blood sugar filter.

In some embodiments, the second plurality of filters includes a plurality of filters selected from the filters listed in Table 3. In one embodiment, the second plurality of filters includes a first liver disease filter, a first urinary problem filter, a first surgery filter, a first dietary filter, a first pancreatic disease filter, a first alcohol consumption filter, and a first diabetes medication filter.

In some embodiments, the first and second plurality of filters includes filters selected from the filters listed in Table 7. In some embodiments, the first plurality of filters of the first category class include a first sub-plurality of the filters listed in Table 7, for example, 2, 3, 4, 5, 6, 7, 8, 9, 10, 11, 12, 13, 14, 15, 16, 17, or all 18 of the filters listed in Table 7, and the second plurality of filters of the first category class include a second sub-plurality of the filters listed in Table 7, which is different from the first sub-plurality of filters, for example, 2, 3, 4, 5, 6, 7, 8, 9, 10, 11, 12, 13, 14, 15, 16, 17, or all 18 of the filters listed in Table 7. In some embodiments, each of the filters in the first sub-plurality of filters is different from each of the filters in the second sub-plurality of filters (e.g., no filter listed in Table 7 is included in both the first sub-plurality and the second sub-plurality of filters). In some embodiments, a system for qualifying a subject for delivery of an over-the-counter gliflozin Sodium-Glucose Cotransport 2 inhibitor pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 7, e.g., at least 2, 3, 4, 5, 6, 7, 8, 9, 10, 11, 12, 13, 14, 15, 16, 17, or all 18 of the filters listed in Table 7. In some embodiments, where a filter listed in Table 7 corresponds to a filter listed in Table 2 or Table 3, a threshold level sufficient to fire the corresponding filter listed in Table 2 or Table 3, as described in detail above, is sufficient to fire the filter listed in Table 7.

TABLE 7

Example filters for contraindications and risk factors associated with qualifying a subject for an over-the-counter provision of a gliflozin Sodium-Glucose Cotransport 2 inhibitor pharmaceutical composition

| Filter | Example Criteria |
|---|---|
| 1b | a pregnancy filter |
| 2b | a Type 1 diabetes filter |
| 3b | a ketoacidosis filter |
| 4b | a kidney disease filter |
| 5b | an age filter |
| 6b | a blood sugar filter |
| 7b | a liver disease filter |
| 8b | a urinary problem filter |
| 9b | a surgery filter |
| 10b | a dietary filter |
| 11b | a pancreatic disease filter |
| 12b | an alcohol consumption filter |
| 13b | a diabetes medication filter |
| 14b | an amputation filter |
| 15b | a leg neuropathy filter |
| 16b | a diabetic foot ulcer filter |
| 17b | an adverse reaction filter |
| 18b | a bladder cancer filter |

In one aspect, the disclosure provides methods, software, and computer systems for qualifying a human subject for a re-order for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels. In one embodiment, a computer system includes instructions, responsive to receiving a re-order request from the subject for the gliflozin Sodium-Glucose Cotransport 2 inhibitor pharmaceutical composition, performing a re-fulfillment procedure comprising conducting a second survey of the subject thereby obtaining a second plurality of survey results necessary to run against a third plurality of filters of a first category class and a fourth plurality of filters of a second category class. The method then includes running all or a portion of the second plurality of survey results against a third plurality of filters of a first category class, wherein, when a respective filter in the third plurality of filters is fired, the subject is deemed not qualified for delivery of the gliflozin Sodium-Glucose Cotransport 2 inhibitor pharmaceutical composition and the method is terminated without delivery of the gliflozin Sodium-Glucose Cotransport 2 inhibitor pharmaceutical composition to the subject. The method then includes running all or a portion of the second plurality of survey results against a fourth plurality of filters of a second category class, wherein, when a respective filter in the fourth plurality of filters is fired, the subject is provided with a warning corresponding to the respective filter. The method also includes obtaining acknowledgment from the subject for the warning issued to the subject by any filter in the fourth plurality of filters. The method also includes proceeding with a re-fulfillment process when no filter in the third plurality of filters has been fired and the subject has acknowledged each warning associated with each filter in the fourth plurality of filters that was fired. The re-fulfillment process includes: storing an indication in a subject profile of a re-order for the gliflozin Sodium-Glucose Cotransport 2 inhibitor pharmaceutical composition, communicating the over-the-counter drug facts label for the gliflozin Sodium-Glucose Cotransport 2 inhibitor pharmaceutical composition to the subject, and authorizing, upon confirmation from the subject that the over-the-counter drug facts label has been received and read, provision of the gliflozin Sodium-Glucose Cotransport 2 inhibitor pharmaceutical composition to the subject. In some embodiments, the third series of filters includes one or more filters listed in Table 5.

In some embodiments, the third plurality of filters includes a second pregnancy filter, a ketoacidosis symptom filter, a kidney problem filter, a second urinary problem filter, a bodily stress filter, and a second diabetes medication filter.

In some embodiments, the fourth series of filters includes one or more filters listed in Table 6. In some embodiments, the fourth plurality of filters includes a second surgery filter, a second dietary filter, a second pancreatic disease filter, a second alcohol consumption filter, a yeast infection filter, and a hypoglycemia symptom filter.

In some embodiments, the third and fourth plurality of filters includes filters selected from the filters listed in Table 8. In some embodiments, the third plurality of filters of the first category class include a third sub-plurality of the filters listed in Table 8, for example, 2, 3, 4, 5, 6, 7, 8, 9, 10, 11, 12, 13, 14, 15, 16, 17, 18, 19 or all 20 of the filters listed in Table 8, and the fourth plurality of filters of the first category class include a fourth sub-plurality of the filters listed in Table 8, which is different from the third sub-plurality of filters, for example, 2, 3, 4, 5, 6, 7, 8, 9, 10, 11, 12, 13, 14, 15, 16, 17, 18, 19 or all 20 of the filters listed in Table 8. In some embodiments, each of the filters in the third sub-plurality of filters is different from each of the filters in the fourth sub-plurality of filters (e.g., no filter listed in Table 8 is included in both the first sub-plurality and the second sub-plurality of filters). In some embodiments, a system for qualifying a subject for delivery of an over-the-counter gliflozin Sodium-Glucose Cotransport 2 inhibitor pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 8, e.g., at least 2, 3, 4, 5, 6, 7, 8, 9, 10, 11, 12, 13, 14, 15, 16, 17, 18, 19 or all 20 of the filters listed in Table 8. In some embodiments, where a filter listed in Table 8 corresponds to a filter listed in Table 2, Table 3, Table 5, or Table 6, a threshold level sufficient to fire the corresponding filter listed in Table 2, Table 3, Table 5, or Table 6, as described in detail above, is sufficient to fire the filter listed in Table 8.

TABLE 8

Example filters for contraindications and risk factors associated with qualifying a subject for an over-the-counter provision of a gliflozin Sodium-Glucose Cotransport 2 inhibitor pharmaceutical composition

| Filter | Example Criteria |
|---|---|
| 1b | a pregnancy filter |
| 2b | a ketoacidosis symptom filter |
| 3b | a kidney problem filter |
| 4b | a urinary problem filter |
| 5b | a bodily stress filter |
| 6b | a diabetes medication filter |
| 7b | a liver disease filter |
| 8b | a surgery filter |
| 9b | a dietary filter |
| 10b | a pancreatic disease filter |
| 11b | an alcohol consumption filter |
| 12b | a yeast infection filter |
| 13b | a hypoglycemia filter |
| 14b | a bladder cancer filter |
| 15b | a dehydration filter |
| 16b | a heart failure filter |
| 17b | an amputation filter |
| 18b | a leg neuropathy filter |
| 19b | a diabetic foot ulcer filter |
| 20b | a hyperkalemia filter |

In one aspect, the present disclosure provides a computer system for qualifying a human subject for over-the-counter delivery of a gliflozin Sodium-Glucose Cotransport 2 inhibitor pharmaceutical composition for lowering blood sugar, the computer system comprising one or more processors and a memory, the memory comprising non-transitory instructions which, when executed by the one or more processor, perform a method comprising: a) conducting a first survey of the subject thereby obtaining a first plurality of survey results, wherein the first plurality of survey results comprises: whether the subject is one of (i) pregnant, (ii) breastfeeding, or (iii) planning to become pregnant, a Type 1 diabetes status of the subject, a ketoacidosis status of the subject, a kidney disease status of the subject, an age of the subject, a blood sugar level of the subject, whether the subject has a liver problem, whether the subject has ever had a urinary problem, a surgery status of the subject, a dietary status of the subject, whether the subject has ever had a pancreatic problem, an alcohol consumption status of the subject, and whether the subject is taking a diabetes medication; b) running all or a portion of the first plurality of survey results against a first plurality of filters of a first category class, wherein, when a respective filter in the first plurality of filters is fired, the subject is deemed not qualified for delivery of the gliflozin Sodium-Glucose Cotransport 2 inhibitor pharmaceutical composition and the method is terminated without delivery of the gliflozin Sodium-Glucose Cotransport 2 inhibitor pharmaceutical composition to the subject, wherein the first plurality of filters comprises: a first pregnancy filter that is fired at least when the first plurality of survey results indicates that the subject is pregnant or the subject is breastfeeding, a Type 1 diabetes filter that is fired at least when the first plurality of survey results indicates that the subject has Type 1 diabetes, a ketoacidosis filter that is fired at least when the first plurality of survey results indicates that the subject has ketoacidosis, a first kidney disease filter that is fired at least when the first plurality of survey results indicates that the subject has kidney disease, an age filter, and a first blood sugar filter that is fired at least when the first plurality of survey results indicates that the subject has a blood sugar level that is either (i) below a first baseline blood sugar level or (ii) above a ceiling blood sugar level; c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises: a first liver disease filter that is fired at least when the first plurality of survey results indicates that the subject has a liver problem, a first urinary problem filter that is fired at least when the first plurality of survey results indicates that the subject has a history of urinary problems, a first surgery filter that is fired at least when the first plurality of survey results indicates that the subject is planning on undergoing surgery, a first dietary filter that is fired at least when the first plurality of survey results indicates that the subject is eating less than before, a first pancreatic disease filter that is fired at least when the first plurality of survey results indicates that the subject has had a pancreatic problem, a first alcohol consumption filter, and a first diabetes medication filter that is fired at least when the first plurality of survey results indicates that the subject is taking a diabetes medication; d) obtaining acknowledgment from the subject for the warning issued to the subject by any filter in the second plurality of filters; e) proceeding with a fulfillment process when (i) no filter in the first plurality of filters has been fired and (ii) the subject has acknowledged each warning associated with each filter in the second plurality of filters that was fired, wherein the fulfillment process comprises: storing an indication in a subject profile of an initial order for the gliflozin Sodium-Glucose Cotransport 2 inhibitor pharmaceutical composition, communicating an over the counter drug facts label for the gliflozin Sodium-Glucose Cotransport 2 inhibitor pharmaceutical composition to the subject, and authorizing, upon confirmation from the subject that the over the counter drug facts label has been received and read, provision of the gliflozin Sodium-Glucose Cotransport 2 inhibitor pharmaceutical composition to the subject.

In some embodiments of the aspects disclosed above, the gliflozin Sodium-Glucose Cotransport 2 inhibitor pharmaceutical composition has the structure:

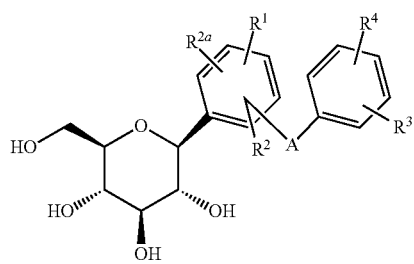

where: $R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five, six or seven membered carbocycle or heterocycle which may contain 1 to 4 heteroatoms in the ring which are N, O, S, SO, and/or $SO_2$; $R_3$ and $R_4$ are independently hydrogen, OH, $OR^{5a}$, OAryl, $OCH_2Aryl$, alkyl, cycloalkyl, $CF_3$, —$OCHF_2$, —$OCF_3$, halogen, —CN, —$CO_2R^{5b}$, —$CO_2H$, $COR^{6b}$, —CH(OH) $R^{6e}$, —CH(OR$^{5f}$)R$^{6d}$, —CONR$^6$R$^{6a}$, —NHCOR$^{5c}$, —NHSO$_2$R$^{5d}$, —NHSO$_2$Aryl, Aryl, —SR$^{5e}$, —SOR$^{5f}$, —SO$_2$R$^{5g}$, —SO$_2$Aryl, or a five, six or seven membered heterocycle which may contain 1 to 4 heteroatoms in the ring which are N, O, S, SO, and/or SO$_2$, or R$^3$ and R$^4$ together with the carbons to which they are attached form an annelated five, six or seven membered carbocycle or heterocycle which may contain 1 to 4 heteroatoms in the ring which are N, O, S, SO, and/or SO$_2$; R$^5$, R$^{5a}$, R$^{5b}$, R$^{5c}$, R$^{5d}$, R$^{5e}$, R$^{5f}$, R$^{5g}$, R$^{5h}$ and R$^{5i}$ are independently alkyl; R$^6$, R$^{6a}$, R$^{6b}$, R$^{6c}$, and R$^{6d}$ are independently hydrogen, alkyl, aryl, alkylaryl or cycloalkyl, or R$^6$ and R$^{6a}$ together with the nitrogen to which they are attached form an annelated five, six or seven membered heterocycle which may contain 1 to 4 heteroatoms in the ring which are N, O, S, SO, and/or SO$_2$; A is O, S, NH, or (CH$_2$)$_n$, where n is 0-3, or a pharmaceutically acceptable salt, stereoisomer, or prodrug ester thereof; with the proviso that where A is (CH$_2$)$_n$ where n is 0, 1, 2, or 3 or A is O, and at least one of R$^1$, R$^2$, and R$^{2a}$ is OH or OR$^5$, then at least one of R$^1$, R$^2$, and R$^{2a}$ is CF$_3$, OCF$_3$, or OCHF$_2$ and/or at least one of R$^3$ and R$^4$ is CF$_3$, —OCHF$_2$, —OCF$_3$, —CN, —CO$_2$R$^{5b}$, CH(OR$^{5h}$)R$^{6d}$, CH(OH)R$^{6c}$, COR$^{6b}$, —NHCOR$^{5c}$, —NHSO$_2$R$^{5d}$, —NHSO$_2$Aryl, Aryl, —SR$^{5e}$, —SOR$^{5f}$, —SO$_2$R$^{5g}$ or —SO$_2$Aryl.

In some embodiments of the aspects disclosed above, the gliflozin Sodium-Glucose Cotransport 2 inhibitor pharmaceutical composition is dapagliflozin or a pharmaceutically acceptable salt thereof.

In some embodiments of the aspects disclosed above, the gliflozin Sodium-Glucose Cotransport 2 inhibitor pharmaceutical composition is dapagliflozin propanediol.

In some embodiments of the aspects disclosed above, upon confirmation from the subject that the over the counter drug facts label has been received and read, the subject is authorized for provision of a dosage of from 5 mg to 10 mg per day of the gliflozin Sodium-Glucose Cotransport inhibitor pharmaceutical composition.

In some embodiments of the aspects disclosed above, upon confirmation from the subject that the over the counter drug facts label has been received and read, the subject is authorized for provision of a dosage of 5 mg per day of the gliflozin Sodium-Glucose Cotransport inhibitor pharmaceutical composition.

In some embodiments of the aspects disclosed above, the gliflozin Sodium-Glucose Cotransport inhibitor pharmaceutical composition is selected from the group consisting of empagliflozin, canagliflozin, and ertugliflozin.

In some embodiments of the aspects disclosed above, the gliflozin Sodium-Glucose Cotransport inhibitor pharmaceutical composition is empagliflozin and the subject is administered a dosage from 2.5 mg to 50 mg per day.

In some embodiments of the aspects disclosed above, upon confirmation from the subject that the over the counter drug facts label has been received and read, the subject is authorized for provision of a dosage selected from the set of 5 mg, 10 mg, 20 mg, and/or 25 mg per day of empagliflozin.

In some embodiments of the aspects disclosed above, the gliflozin Sodium-Glucose Cotransport inhibitor pharmaceutical composition is canagliflozin and the subject is administered a dosage from 50 mg to 600 mg per day.

In some embodiments of the aspects disclosed above, upon confirmation from the subject that the over the counter drug facts label has been received and read, the subject is authorized for provision of a dosage selected from the set of 100 mg, 200 mg, and/or 300 mg per day of canagliflozin.

In some embodiments of the aspects disclosed above, the gliflozin Sodium-Glucose Cotransport inhibitor pharmaceutical composition is ertugliflozin and the subject is administered a dosage from 1 mg to 30 mg per day.

In some embodiments of the aspects disclosed above, upon confirmation from the subject that the over the counter drug facts label has been received and read, the subject is authorized for provision of a dosage selected from the set of 2.5 mg, 5 mg, and/or 15 mg per day of ertugliflozin.

In some embodiments of the aspects disclosed above, the first pregnancy filter is also fired when the first plurality of survey results indicates that the subject plans to become pregnant within a predetermined period of time.

In some embodiments of the aspects disclosed above, the age filter is fired when the first plurality of survey results indicates that the subject is less than eighteen years old.

In some embodiments of the aspects disclosed above, the first baseline blood sugar level used in the first blood sugar filter is 6.5% glycated hemoglobin.

In some embodiments of the aspects disclosed above, the ceiling blood sugar level used in the first blood sugar filter is 8% glycated hemoglobin.

In some embodiments of the aspects disclosed above, when the first urinary problem filter is fired when the first plurality of survey results indicates that the subject has a history of urinary tract infections or problems urinating.

In some embodiments of the aspects disclosed above, when the first dietary filter is fired when the first plurality of survey results indicates that the subject is eating less due to illness, surgery, or a recent change in diet.

In some embodiments of the aspects disclosed above, the first alcohol consumption filter is fired when the first plurality of survey results indicates that the subject, on average, consumes at least a predetermined number of alcoholic drinks over a predetermined period of time.

In some embodiments of the aspects disclosed above, the first plurality of survey results further comprises whether the subject is allergic to the gliflozin Sodium-Glucose Cotransport 2 inhibitor pharmaceutical composition, and the first plurality of filters includes an adverse reaction filter that is fired when the first plurality of survey results indicates that the subject is allergic to the gliflozin Sodium-Glucose Cotransport 2 inhibitor pharmaceutical composition.

In some embodiments of the aspects disclosed above, the first plurality of survey results further comprises whether the subject has ever had bladder cancer, and the first plurality of filters includes a first bladder cancer filter that is fired when the first plurality of survey results indicates that the subject has had bladder cancer.

In some embodiments of the aspects disclosed above, the warning corresponding to a respective filter in the second plurality of filters comprises a prompt for the subject to indicate whether they have discussed the risk factor underlying the respective filter in the second plurality of filters that was fired with a health care professional; and acknowledgement is obtained from the subject when the subject indicates that they have discussed the risk factor underlying the respective filter in the second plurality of filters that was fired with a health care professional.

In some embodiments of the aspects disclosed above, the fulfillment process further comprises: storing a destination associated with the subject in the subject profile.

In some embodiments of the aspects disclosed above, the fulfillment process further comprises: coordinating shipping of the gliflozin Sodium-Glucose Cotransport 2 inhibitor pharmaceutical composition to a physical address associated with the subject.

In some embodiments of the aspects disclosed above, the method further comprises: f) responsive to receiving a re-order request from the subject for the gliflozin Sodium-Glucose Cotransport 2 inhibitor pharmaceutical composition, performing a re-fulfillment procedure comprising: (i) conducting a second survey of the subject thereby obtaining a second plurality of survey results, wherein the second plurality of survey results comprises information indicating: whether the subject is one of (i) pregnant, (ii) breastfeeding, or (iii) planning to become pregnant, whether the subject has developed ketoacidosis since receiving their last provision of the gliflozin Sodium-Glucose Cotransport 2 inhibitor pharmaceutical composition, whether the subject has developed a kidney problem since receiving their last provision of the gliflozin Sodium-Glucose Cotransport 2 inhibitor pharmaceutical composition, whether the subject has developed a urinary problem since receiving their last provision of the gliflozin Sodium-Glucose Cotransport 2 inhibitor pharmaceutical composition, whether the subject has developed a liver problem since receiving their last provision of the gliflozin Sodium-Glucose Cotransport 2 inhibitor pharmaceutical composition, a surgery status of the subject, a dietary status of the subject, whether the subject has developed a pancreatic problem since receiving their last provision of the gliflozin Sodium-Glucose Cotransport 2 inhibitor pharmaceutical composition, an alcohol consumption status of the subject, whether the subject has experienced a yeast infection since receiving their last provision of the gliflozin Sodium-Glucose Cotransport 2 inhibitor pharmaceutical composition, whether the subject has developed hypoglycemia since receiving their last provision of the gliflozin Sodium-Glucose Cotransport 2 inhibitor pharmaceutical composition, whether the subject is experiencing a bodily stress, and whether the subject is taking a diabetes medication; (ii) running all or a portion of the second plurality of survey results against a third plurality of filters of the first category class, wherein, when a respective filter in the third plurality of filters is fired, the subject is deemed not qualified for the gliflozin Sodium-Glucose Cotransport 2 inhibitor pharmaceutical composition and the re-fulfillment process is terminated without delivery of the gliflozin Sodium-Glucose Cotransport 2 inhibitor pharmaceutical composition to the subject, wherein the third plurality of filters comprise: a second pregnancy filter that is fired at least when the second plurality of survey results indicates that the subject is pregnant or the subject is breastfeeding, a ketoacidosis symptom filter that is fired at least when the second plurality of survey results indicates that the subject has developed ketoacidosis since receiving their last provision of the gliflozin Sodium-Glucose Cotransport 2 inhibitor pharmaceutical composition, a kidney problem filter that is fired at least when the second plurality of survey results indicates that the subject has developed a kidney problem since receiving their last provision of the gliflozin Sodium-Glucose Cotransport 2 inhibitor pharmaceutical composition, a second urinary problem filter that is fired at least when the second plurality of survey results indicates that the subject has developed a urinary tract infection since receiving their last provision of the gliflozin Sodium-Glucose Cotransport 2 inhibitor pharmaceutical composition, a bodily stress filter that is fired at least when the second plurality of survey results indicates that the subject is experiencing a bodily stress, and a second diabetes medication filter that is fired at least when the second plurality of survey results indicates that the subject is taking a diabetes medication; (iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises: a second liver disease filter that is fired at least when the second plurality of survey results indicates that the subject has developed a liver problem since receiving their last provision of the gliflozin Sodium-Glucose Cotransport 2 inhibitor pharmaceutical composition, a second surgery filter that is fired at least when the second plurality of survey results indicates that the subject is planning on undergoing surgery, a second dietary filter that is fired at least when the second plurality of survey results indicates that the subject is eating less than before receiving their last provision of the gliflozin Sodium-Glucose Cotransport 2 inhibitor pharmaceutical composition, a second pancreatic disease filter that is fired at least when the second plurality of survey results indicates that the subject has developed a pancreatic problem since receiving their last provision of the gliflozin Sodium-Glucose Cotransport 2 inhibitor pharmaceutical composition, a second alcohol consumption filter, a yeast infection filter that is fired at least when the second plurality of survey results indicates that the subject has experienced a yeast infection since receiving their last provision of the gliflozin Sodium-Glucose Cotransport 2 inhibitor pharmaceutical composition, and a hypoglycemia symptom filter that is fired at least when the second plurality of survey results indicates that the subject has developed hypoglycemia since receiving their last provision of the gliflozin Sodium-Glucose Cotransport 2 inhibitor pharmaceutical composition; (iv) obtaining acknowledgment from the subject for the warning issued to the subject by any filter in the fourth plurality of filters; and (v) proceeding with the re-fulfillment process when (i) the re-fulfillment process is not already terminated by the firing of a filter in the third plurality of filters and (ii) the subject has acknowledged each warning associated with each filter in the third plurality of filters that was fired and that is associated with a warning, wherein the re-fulfillment process further comprises: storing an indication in the subject profile of a re-order for the gliflozin Sodium-Glucose Cotransport 2 inhibitor pharmaceutical composition, communicating the over the counter drug facts label for the gliflozin Sodium-Glucose Cotransport 2 inhibitor pharmaceutical composition to the subject, and authorizing, upon confirmation from the subject that the over the counter drug facts label has been received and read, a re-order provision of the gliflozin Sodium-Glucose Cotransport 2 inhibitor pharmaceutical composition to the subject.

In some embodiments of the aspects disclosed above, the second pregnancy filter is also fired when the second plurality of survey results indicates that the subject plans to become pregnant within a predetermined period of time.

In some embodiments of the aspects disclosed above, a symptom of ketoacidosis, which is capable of firing the ketoacidosis filter, is selected from the group consisting of an increase of ketones in the blood of the subject, an increase of ketones in the urine of the subject, nausea, tiredness, vomiting, trouble breathing, and abdominal pain.

In some embodiments of the aspects disclosed above, a symptom of a kidney problem, which is capable of firing the kidney problem symptom filter, is selected from the group consisting of the subject is eating less than before, the subject is drinking less than before, vomiting, diarrhea, dehydration, and being diagnosed with kidney disease.

In some embodiments of the aspects disclosed above, a symptom of a urinary problem, which is capable of firing the urinary problem filter, is selected from the group consisting of a burning sensation when passing urine, an increased urge to urinate, pelvic pain, blood in the urine, fever, back pain, nausea, and vomiting.

In some embodiments of the aspects disclosed above, the second alcohol consumption filter is fired when the second plurality of survey results indicates that the subject, on average, consumes at least a predetermined number of alcoholic drinks over a predetermined period of time.

In some embodiments of the aspects disclosed above, a symptom of a yeast infection, which is capable of firing the yeast infection filter, is selected from the group consisting of a yeast infection of the penis, a yeast infection of the vagina, a sore throat, an increased urge to urinate, an increased volume of urine, and an increased urge to urinate at night.

In some embodiments of the aspects disclosed above, a symptom of hypoglycemia, which is capable of firing the hypoglycemia symptom filter, is selected from the group consisting of shaking, sweating, rapid heartbeat, change in vision, increased hunger, headaches, and a change in mood.

In some embodiments of the aspects disclosed above, a bodily stress, which is capable of firing the bodily stress filter, is selected from the group consisting of a fever, a recent trauma, an infection, and a recent surgery.

In some embodiments of the aspects disclosed above, the second plurality of survey results further comprises whether the subject has experienced a symptom of dehydration since receiving their last provision of the gliflozin Sodium-Glucose Cotransport 2 inhibitor pharmaceutical composition, and the fourth plurality of filters further comprises a dehydration filter that is fired at least when the second plurality of survey results indicates that the subject has experienced, since receiving their last provision of the gliflozin Sodium-Glucose Cotransport 2 inhibitor pharmaceutical composition, a symptom of dehydration selected from the group consisting of dizziness, faintness, light-headedness, and weakness.

In some embodiments of the aspects disclosed above, the second plurality of survey results further comprises a bladder cancer status of the subject, and the third plurality of filters further comprises a second bladder cancer filter that is fired at least when the second plurality of survey results indicates that the subject has developed bladder cancer since receiving their last provision of the gliflozin Sodium-Glucose Cotransport 2 inhibitor pharmaceutical composition.

In some embodiments of the aspects disclosed above, the re-fulfillment procedure further comprises, when the subject profile for the subject does not include a recent blood sugar status for the subject: obtaining, in the second plurality of survey results, a blood sugar status of the subject; and including, in the third plurality of filters of the first category class, a second blood sugar filter that is fired at least when the second plurality of survey results indicates that the subject has a blood sugar level of at least a second baseline blood sugar level.

In some embodiments of the aspects disclosed above, the re-fulfillment procedure further comprises: obtaining, in the second plurality of survey results, a blood sugar status of the subject; and including, in the third plurality of filters of the first category class, a second blood sugar filter that is fired at least when the second plurality of survey results indicates that the subject has a blood sugar level of at least a second baseline blood sugar level.

In some embodiments of the aspects disclosed above, the second baseline blood sugar level used in the second blood sugar filter is 7% glycated hemoglobin.

In some embodiments of the aspects disclosed above, the lowering of blood sugar is to treat or prevent type 2 diabetes.

In some embodiments of the aspects disclosed above, the gliflozin Sodium-Glucose Cotransport 2 inhibitor pharmaceutical composition includes canagliflozin; the first plurality of survey results further comprises one or more survey results selected from the group consisting of: a heart failure history of the subject, an amputation history of the subject, a leg neuropathy history of the subject, a diabetic foot ulcer history of the subject, and a hyperkalemia history of the subject; and the first plurality of filters and/or the second plurality of filters further comprises one or more filters selected from the group consisting of: a heart failure filter that is triggered at least when the first plurality of survey results indicates that the subject has a history of heart failure; an amputation filter that is triggered at least when the first plurality of survey results indicates that the subject has a body part amputated; a leg neuropathy filter that is triggered at least when the first plurality of survey results indicates that the subject has a leg neuropathy; a diabetic foot ulcer filter that is triggered at least when the first plurality of survey results indicates that the subject has a diabetic foot ulcer; and a hyperkalemia filter that is triggered at least when the first plurality of survey results indicates that the subject has hyperkalemia.

In some embodiments of the aspects disclosed above, the gliflozin Sodium-Glucose Cotransport 2 inhibitor pharmaceutical composition includes ertugliflozin; the first plurality of survey results further comprises one or more survey results selected from the group consisting of: an amputation history of the subject, a leg neuropathy history of the subject, and a diabetic foot ulcer history of the subject; and the first plurality of filters and/or the second plurality of filters further comprises one or more filters selected from the group consisting of: an amputation filter that is triggered at least when the first plurality of survey results indicates that the subject has a body part amputated; a leg neuropathy filter that is triggered at least when the first plurality of survey results indicates that the subject has a leg neuropathy; and a diabetic foot ulcer filter that is triggered at least when the first plurality of survey results indicates that the subject has a diabetic foot ulcer.

In some embodiments, the disclosure provides methods for lowering blood pressure with an over the counter gliflozin Sodium-Glucose Cotransport 2 inhibitor pharmaceutical composition. The method includes providing a first survey for obtaining a first information set from the human, via a computer system having a processor programmed to perform the first survey, where the first information set includes information about the human that relates to potential risk factors and contraindications for the gliflozin Sodium-Glucose Cotransport 2 inhibitor pharmaceutical composition, as described herein. The method also includes applying an algorithm to the first information set, via a computer system having a processor programmed to perform the algorithm. The algorithm runs all or a portion of the first information set against a first plurality of filters, where the human is deemed not qualified for treatment with the over the counter gliflozin Sodium-Glucose Cotransport 2 inhibitor pharmaceutical composition for lowering blood pressure when a respective filter in the first plurality of filters is fired and the method is terminated without authorizing provision of the gliflozin Sodium-Glucose Cotransport 2 inhibitor pharmaceutical composition to the human, where the first plurality of filters includes filters related to contraindications of the gliflozin Sodium-Glucose Cotransport 2 inhibitor pharmaceutical composition as described herein. The algorithm also runs all or a portion of the first information set against a second plurality of filters, where, when a respective filter in the second plurality of filters is fired, the human is provided with a warning corresponding to the respective filter, and where the second plurality of filters includes filters related to risk factors for the gliflozin Sodium-Glucose Cotransport 2 inhibitor pharmaceutical composition as described herein. The algorithm also obtains acknowledgment from the human of the risk factor associated with each warning issued to the human by any filter in the second plurality of filters. In some embodiments, the acknowledgement includes confirmation that the human has discussed the risk factor with a physician. The algorithm proceeds with a fulfillment process when (a) no filter in the first plurality of filters has been fired and (b) the human has acknowledged each warning associated with each filter in the second plurality of filters that was fired. The fulfillment process includes storing an indication in a subject profile of an initial order for the gliflozin Sodium-Glucose Cotransport 2 inhibitor pharmaceutical composition, communicating an over the counter drug facts label for the gliflozin Sodium-Glucose Cotransport 2 inhibitor pharmaceutical composition to the human, and authorizing, upon confirmation from the subject that the over the counter drug facts label has been received and read, provision of the gliflozin Sodium-Glucose Cotransport 2 inhibitor pharmaceutical composition to the human, where the authorization includes a destination associated with the subject. In some embodiments, the method also includes treating the human to lower the blood pressure of the human, upon authorization of the provision e.g., by providing access to the gliflozin Sodium-Glucose Cotransport 2 inhibitor pharmaceutical composition to the human and/or by administering the gliflozin Sodium-Glucose Cotransport 2 inhibitor pharmaceutical composition to lower blood pressure in the human.

EXAMPLES

Example 1

A computer system is configured for qualifying a subject for over-the-counter delivery of a dapagliflozin pharmaceutical composition to treat diabetes (e.g., by lowering blood sugar). The computer system includes instructions for conducting a survey of the subject. The survey is utilized to obtain one or more results of: whether the subject is one of pregnant, breastfeeding, or planning to become pregnant, a Type 1 diabetes status of the subject, a ketoacidosis status of the subject, a kidney disease status of the subject, an age of the subject, a blood sugar level of the subject, whether the subject has a liver problem, whether the subject has ever had a urinary problem, a surgery status of the subject, a dietary status of the subject, whether the subject has ever had a pancreatic problem, an alcohol consumption status of the subject, whether the subject is taking a diabetes medication, and whether the subject has ever had bladder cancer.

The computer system runs survey results against a first series of filters that are each associated with a first filter category class. The first filter category class is configured to prevent authorization for OTC delivery of the OTC dapagliflozin when the subject's survey results identify a contraindication for the dapagliflozin. In some embodiments, the first series of filters includes one or more of a first pregnancy filter, a Type 1 diabetes filter, a ketoacidosis filter, a first kidney disease filter, an age filter, a first blood sugar filter and a first bladder cancer filter. The first pregnancy filter is configured to ensure the subject is not pregnant, breastfeeding, or planning to become pregnant. The Type 1 diabetes filter is configured to ensure the subject does not have Type 1 diabetes. The ketoacidosis filter is configured to ensure the subject does not have ketoacidosis. The first kidney disease filter is configured to ensure that the subject does not have kidney disease. The age filter is configured to ensure the subject is greater than or equal to eighteen years old. The first blood sugar filter is configured to ensure that the subject has a blood sugar level that is either above a first baseline blood sugar level (e.g., 6.5% glycated hemoglobin) or below a ceiling blood sugar level (e.g., 8% glycated hemoglobin). Furthermore, the first bladder cancer filter is configured to ensure the subject does not have bladder cancer.

The computer system runs survey results against a second series of filters that each generates a warning where the subject's survey results identify a risk factor for the OTC dapagliflozin. In some embodiments, the second series of filters includes a first liver disease filter, a first urinary problem filter, a first surgery filter, a first dietary filter, a first pancreatic disease filter, a first alcohol consumption filter, and a first diabetes medication filter. The first liver disease filter is configured to ensure the subject has not ever had a liver problem. The first urinary problem filter is configured to ensure the subject does not have a history of urinary problems or a history of urinary tract infections or problems urinating. The first surgery filter is configured to ensure the subject is not planning to undergo surgery. The first dietary filter is configured to ensure the subject is not eating less than before, whether due to illness, surgery, or a recent change in diet. The first pancreatic disease filter is configured to ensure the subject does not have a pancreatic problem. The first alcohol consumption filter is configured to ensure the subject is not consuming, on average, more than a predetermined number of alcoholic drinks over a predetermined period of time. The first diabetes medication filter is configured to ensure the subject is not taking diabetes medication.

The computer system then prompts the subject to acknowledge or deny having discussed these warnings with a medical professional (e.g., their physician or healthcare professional). The computer system then proceeds with a fulfillment process only when none of the first series of filters was fired and the subject acknowledged that they discussed each warning issued in association with the second series of filters that was fired.

The computer system stores an indication of an initial order of the OTC amlodipine in a subject profile, and communicates an over-the-counter drug facts label for the dapagliflozin pharmaceutical composition to the subject. Upon confirmation from the subject that they have received and read the over-the-counter drug facts label, the computer system authorizes provision of the OTC dapagliflozin pharmaceutical composition to the subject.

In some embodiments, the computer system includes instructions for conducting another survey of the subject responsive to a re-order request of the dapagliflozin pharmaceutical composition. This survey is utilized to obtain one or more results of: whether the subject is one of pregnant, breastfeeding, or planning to become pregnant, whether the subject has experienced a symptom of ketoacidosis since receiving their last provision of the dapagliflozin pharmaceutical composition, whether the subject has experienced a symptom of a kidney problem since receiving their last provision of the dapagliflozin pharmaceutical composition, whether the subject has experienced a symptom of a urinary problem since receiving their last provision of the dapagliflozin pharmaceutical composition, whether the subject has experienced a liver problem since receiving their last provision of the dapagliflozin pharmaceutical composition, a surgery status of the subject, a dietary status of the subject, whether the subject has experienced a pancreatic problem since receiving their last provision of the dapagliflozin pharmaceutical composition, an alcohol consumption status of the subject, whether the subject has experienced a yeast infection since receiving their last provision of the dapagliflozin pharmaceutical composition, whether the subject has experienced a symptom of hypoglycemia since receiving their last provision of the dapagliflozin pharmaceutical composition, whether the subject is experiencing a bodily stress, and whether the subject is taking a diabetes medication.

The computer system runs survey results against a third series of filters that are each associated with the first filter category class. In some embodiments, the third series of filters includes one or more of a second pregnancy filter, a ketoacidosis symptom filter, a kidney problem filter, a second urinary problem filter, a bodily stress filter, and a second diabetes medication filter. This second pregnancy filter is configured to ensure the subject is not pregnant, breastfeeding, or planning to become pregnant within a predetermined period of time. The ketoacidosis filter is configured to ensure the subject has not experienced a symptom of ketoacidosis since receiving their last provision of dapagliflozin. Symptoms of ketoacidosis that are capable of firing the ketoacidosis symptom filter include an increase of ketones in the blood of the subject, an increase of ketones in the urine of the subject, nausea, tiredness, vomiting, trouble breathing, and abdominal pain. The kidney problem filter is configured to ensure the subject has not experienced symptoms of a kidney problem since receiving their last provision of dapagliflozin. Symptoms of a kidney problem that are capable of firing the kidney problem symptom filter include the subject is eating less than before, the subject is drinking less than before, vomiting, diarrhea, dehydration, and the subject being diagnosed with kidney disease. The second urinary problem filter is configured to ensure the subject has not experienced symptoms of a urinary tract infection since receiving their last provision of dapagliflozin. Symptoms of a urinary problem that are capable of firing the urinary problem filter include a burning sensation when passing urine, an increased urge to urinate, pelvic pain, blood in the urine, fever, back pain, nausea, and vomiting. The bodily stress filter is configured to ensure the subject is not undergoing a bodily stress. Bodily stresses that are capable of firing the bodily stress filter include fever, a recent trauma, an infection, and a recent surgery. The second diabetes filter is configured to ensure the subject is not taking a diabetes medication.

The computer system runs survey results against a fourth series of filters that each generates a warning where the subject's survey results identify a risk factor for the OTC amlodipine. In some embodiments, the fourth series of filters includes a second liver disease filter, a second surgery filter, a second dietary filter, a second pancreatic disease filter, a second alcohol consumption filter, a yeast infection filter, and a hypoglycemia symptom filter. The second liver disease filter is configured to be fired at least when the survey results indicates that the subject has developed symptoms of liver disease since receiving their last provision of the dapagliflozin pharmaceutical composition. The second surgery filter is configured to ensure the subject is not planning on undergoing surgery. The second dietary filter is configured to ensure the subject is not eating less since receiving their last provision of the dapagliflozin pharmaceutical composition. The second pancreatic disease filter is configured to ensure the subject has not developed a pancreatic problem since receiving their last provision of the dapagliflozin pharmaceutical composition. The second alcohol consumption filter is configured to ensure the subject is not, on average, consuming more than a predetermined number of drinks over a predetermined time. The yeast infection filter is configured to ensure the subject has not experienced symptoms of a yeast infection since receiving their last provision of the dapagliflozin pharmaceutical composition. Yeast infections that are capable of firing the yeast infection filter include a yeast infection of the penis, a yeast infection of the vagina, a sore throat, an increased urge to urinate, an increased volume of urine, and an increased urge to urinate at night. The hypoglycemia symptom filter is configured to ensure the subject has not experienced symptoms of hypoglycemia since receiving their last provision of the dapagliflozin pharmaceutical composition. Symptoms of hypoglycemia that are capable of firing the hypoglycemia symptom filter include shaking, sweating, rapid heartbeat, change in vision, increased hunger, headaches, and a change in mood.

The computer system then prompts the subject to acknowledge or deny having discussed these warnings with a medical professional (e.g., their physician or healthcare professional). The computer system then proceeds with a re-fulfillment process only when none of the third series of filters was fired the subject acknowledged that they discussed each warning issued in association with the fourth series of filters that was fired.

The computer system stores an indication of a re-order of the OTC amlodipine in the subject profile, and communicates the over-the-counter drug facts label for the amlodipine pharmaceutical composition to the subject. Upon confirmation from the subject that they have received and read the over-the-counter drug facts label, the computer system authorizes provision of the OTC amlodipine pharmaceutical composition to the subject.

Example 2

A computer system is configured for qualifying a subject for over-the-counter delivery of a canagliflozin pharmaceutical composition to treat diabetes (e.g., by lowering blood sugar). The computer system includes instructions for conducting a survey of the subject. The survey is utilized to obtain one or more results of: whether the subject is one of pregnant, breastfeeding, or planning to become pregnant, a Type 1 diabetes status of the subject, a ketoacidosis status of the subject, a kidney disease status of the subject, an age of the subject, a blood sugar level of the subject, whether the subject has a liver problem, whether the subject has ever had a urinary problem, a surgery status of the subject, a dietary status of the subject, whether the subject has ever had a pancreatic problem, an alcohol consumption status of the subject, whether the subject is taking a diabetes medication, a heart failure history of the subject, an amputation history of the subject, a leg neuropathy history of the subject, a diabetic foot ulcer history of the subject, and a hyperkalemia history of the subject.

The computer system runs survey results against a first series of filters that are each associated with a first filter category class. The first filter category class is configured to prevent authorization for OTC delivery of the OTC canagliflozin when the subject's survey results identify a contraindication for the canagliflozin. In some embodiments, the first series of filters includes one or more of a first pregnancy filter, a Type 1 diabetes filter, a ketoacidosis filter, a first kidney disease filter, an age filter, a first blood sugar filter, a heart failure filter, an amputation filter, a leg neuropathy filter, a diabetic foot ulcer filter, and a hyperkalemia filter. The first pregnancy filter is configured to ensure the subject is not pregnant, breastfeeding, or planning to become pregnant. The Type 1 diabetes filter is configured to ensure the subject does not have Type 1 diabetes. The ketoacidosis filter is configured to ensure the subject does not have ketoacidosis. The first kidney disease filter is configured to ensure that the subject does not have kidney disease. The age filter is configured to ensure the subject is greater than or equal to eighteen years old. The first blood sugar filter is configured to ensure that the subject has a blood sugar level that is either above a first baseline blood sugar level (e.g., 6.5% glycated hemoglobin) or below a ceiling blood sugar level (e.g., 8% glycated hemoglobin). The heart failure filter is configured to ensure the subject does not have a history of heart failure. The amputation filter is configured to ensure the subject does not have any amputated body parts. The leg neuropathy filter is configured to ensure the subject does not have a leg neuropathy. The diabetic foot ulcer filter is configured to ensure the subject does not have a diabetic foot ulcer. Furthermore, the hyperkalemia filter is configured to ensure the subject does not have hyperkalemia.

The computer system runs survey results against a second series of filters that each generates a warning where the subject's survey results identify a risk factor for the OTC canagliflozin. In some embodiments, the second series of filters includes a first liver disease filter, a first urinary problem filter, a first surgery filter, a first dietary filter, a first pancreatic disease filter, a first alcohol consumption filter, a first diabetes medication filter, a heart failure history of the subject, an amputation history of the subject, a leg neuropathy history of the subject, a diabetic foot ulcer history of the subject, and a hyperkalemia history of the subject. The first liver disease filter is configured to ensure the subject has not ever had a liver problem. The first urinary problem filter is configured to ensure the subject does not have a history of urinary problems or a history of urinary tract infections or problems urinating. The first surgery filter is configured to ensure the subject is not planning to undergo surgery. The first dietary filter is configured to ensure the subject is not eating less than before, whether due to illness, surgery, or a recent change in diet. The first pancreatic disease filter is configured to ensure the subject does not have a pancreatic problem. The first alcohol consumption filter is configured to ensure the subject is not consuming, on average, more than a predetermined number of alcoholic drinks over a predetermined period of time. The first diabetes medication filter is configured to ensure the subject is not taking diabetes medication. The heart failure filter is configured to ensure the subject does not have a history of heart failure. The amputation filter is configured to ensure the subject does not have any amputated body parts. The leg neuropathy filter is configured to ensure the subject does not have a leg neuropathy. The diabetic foot ulcer filter is configured to ensure the subject does not have a diabetic foot ulcer. Furthermore, the hyperkalemia filter is configured to ensure the subject does not have hyperkalemia.

The computer system then prompts the subject to acknowledge or deny having discussed these warnings with a medical professional (e.g., their physician or healthcare professional). The computer system then proceeds with a fulfillment process only when none of the first series of filters was fired and the subject acknowledged that they discussed each warning issued in association with the second series of filters that was fired.

The computer system stores an indication of an initial order of the OTC canagliflozin in a subject profile, and communicates an over-the-counter drug facts label for the canagliflozin pharmaceutical composition to the subject. Upon confirmation from the subject that they have received and read the over-the-counter drug facts label, the computer system authorizes provision of the OTC canagliflozin pharmaceutical composition to the subject.

In some embodiments, the computer system includes instructions for conducting another survey of the subject responsive to a re-order request of the canagliflozin pharmaceutical composition. This survey is utilized to obtain one or more results of: whether the subject is one of pregnant, breastfeeding, or planning to become pregnant, whether the subject has experienced a symptom of ketoacidosis since receiving their last provision of the dapagliflozin pharmaceutical composition, whether the subject has experienced a symptom of a kidney problem since receiving their last provision of the canagliflozin pharmaceutical composition, whether the subject has experienced a symptom of a urinary problem since receiving their last provision of the canagliflozin pharmaceutical composition, whether the subject has experienced a liver problem since receiving their last provision of the canagliflozin pharmaceutical composition, a surgery status of the subject, a dietary status of the subject, whether the subject has experienced a pancreatic problem since receiving their last provision of the canagliflozin pharmaceutical composition, an alcohol consumption status of the subject, whether the subject has experienced a yeast infection since receiving their last provision of the canagliflozin pharmaceutical composition, whether the subject has experienced a symptom of hypoglycemia since receiving their last provision of the canagliflozin pharmaceutical composition, whether the subject is experiencing a bodily stress, and whether the subject is taking a diabetes medication.

The computer system runs survey results against a third series of filters that are each associated with the first filter category class. In some embodiments, the third series of filters includes one or more of a second pregnancy filter, a ketoacidosis symptom filter, a kidney problem filter, a second urinary problem filter, a bodily stress filter, and a second diabetes medication filter. This second pregnancy filter is configured to ensure the subject is not pregnant, breastfeeding, or planning to become pregnant within a predetermined period of time. The ketoacidosis filter is configured to ensure the subject has not experienced a symptom of ketoacidosis since receiving their last provision of dapagliflozin. Symptoms of ketoacidosis that are capable of firing the ketoacidosis symptom filter include an increase of ketones in the blood of the subject, an increase of ketones in the urine of the subject, nausea, tiredness, vomiting, trouble breathing, and abdominal pain. The kidney problem filter is configured to ensure the subject has not experienced symptoms of a kidney problem since receiving their last provision of dapagliflozin. Symptoms of a kidney problem that are capable of firing the kidney problem symptom filter include the subject is eating less than before, the subject is drinking less than before, vomiting, diarrhea, dehydration, and the subject being diagnosed with kidney disease. The second urinary problem filter is configured to ensure the subject has not experienced symptoms of a urinary tract infection since receiving their last provision of dapagliflozin. Symptoms of a urinary problem that are capable of firing the urinary problem filter include a burning sensation when passing urine, an increased urge to urinate, pelvic pain, blood in the urine, fever, back pain, nausea, and vomiting. The bodily stress filter is configured to ensure the subject is not undergoing a bodily stress. Bodily stresses that are capable of firing the bodily stress filter include fever, a recent trauma, an infection, and a recent surgery. The second diabetes filter is configured to ensure the subject is not taking a diabetes medication.

The computer system runs survey results against a fourth series of filters that each generates a warning where the subject's survey results identify a risk factor for the OTC canagliflozin. In some embodiments, the fourth series of filters includes a second liver disease filter, a second surgery filter, a second dietary filter, a second pancreatic disease filter, a second alcohol consumption filter, a yeast infection filter, and a hypoglycemia symptom filter. The second liver disease filter is configured to ensure the subject has not developed symptoms of liver disease since receiving their last provision of the canagliflozin pharmaceutical composition. The second surgery filter is configured to ensure the subject is not planning on undergoing surgery. The second dietary filter is configured to ensure the subject is not eating less since receiving their last provision of the canagliflozin pharmaceutical composition. The second pancreatic disease filter is configured to ensure the subject has not developed a pancreatic problem since receiving their last provision of the canagliflozin pharmaceutical composition. The second alcohol consumption filter is configured to ensure the subject is not, on average, consuming more than a predetermined number of drinks over a predetermined time. The yeast infection filter is configured to ensure the subject has not experienced symptoms of a yeast infection since receiving their last provision of the canagliflozin pharmaceutical composition. Yeast infections that are capable of firing the yeast infection filter include a yeast infection of the penis, a yeast infection of the vagina, a sore throat, an increased urge to urinate, an increased volume of urine, and an increased urge to urinate at night. The hypoglycemia symptom filter is configured to ensure the subject has not experienced symptoms of hypoglycemia since receiving their last provision of the canagliflozin pharmaceutical composition. Symptoms of hypoglycemia that are capable of firing the hypoglycemia symptom filter include shaking, sweating, rapid heartbeat, change in vision, increased hunger, headaches, and a change in mood.

The computer system then prompts the subject to acknowledge or deny having discussed these warnings with a medical professional (e.g., their physician or healthcare professional). The computer system then proceeds with a re-fulfillment process only when none of the third series of filters was fired the subject acknowledged that they discussed each warning issued in association with the fourth series of filters that was fired.

The computer system stores an indication of a re-order of the OTC canagliflozin in the subject profile, and communicates the over-the-counter drug facts label for the canagliflozin pharmaceutical composition to the subject. Upon confirmation from the subject that they have received and read the over-the-counter drug facts label, the computer system authorizes provision of the OTC canagliflozin pharmaceutical composition to the subject.

Example 3

A computer system is configured for qualifying a subject for over-the-counter delivery of an ertugliflozin pharmaceutical composition to treat diabetes (e.g., by lowering blood sugar). The computer system includes instructions for conducting a survey of the subject. The survey is utilized to obtain one or more results of: whether the subject is one of pregnant, breastfeeding, or planning to become pregnant, a Type 1 diabetes status of the subject, a ketoacidosis status of the subject, a kidney disease status of the subject, an age of the subject, a blood sugar level of the subject, whether the subject has a liver problem, whether the subject has ever had a urinary problem, a surgery status of the subject, a dietary status of the subject, whether the subject has ever had a pancreatic problem, an alcohol consumption status of the subject, whether the subject is taking a diabetes medication, an amputation history of the subject, a leg neuropathy history of the subject, and a diabetic foot ulcer history of the subject.

The computer system runs survey results against a first series of filters that are each associated with a first filter category class. The first filter category class is configured to prevent authorization for OTC delivery of the OTC ertugliflozin when the subject's survey results identify a contraindication for the ertugliflozin. In some embodiments, the first series of filters includes one or more of a first pregnancy filter, a Type 1 diabetes filter, a ketoacidosis filter, a first kidney disease filter, an age filter, a first blood sugar filter, an amputation filter, a leg neuropathy filter, and a diabetic foot ulcer filter. The first pregnancy filter is configured to ensure the subject is not pregnant, breastfeeding, or planning to become pregnant. The Type 1 diabetes filter is configured to ensure the subject does not have Type 1 diabetes. The ketoacidosis filter is configured to ensure the subject does not have ketoacidosis. The first kidney disease filter is configured to ensure that the subject does not have kidney disease. The age filter is configured to ensure the subject is greater than or equal to eighteen years old. The first blood sugar filter is configured to ensure that the subject has a blood sugar level that is either above a first baseline blood sugar level (e.g., 6.5% glycated hemoglobin) or below a ceiling blood sugar level (e.g., 8% glycated hemoglobin). The amputation filter is configured to ensure the subject does not have any amputated body parts. The leg neuropathy filter is configured to ensure the subject does not have a leg neuropathy.

The computer system runs survey results against a second series of filters that each generates a warning where the subject's survey results identify a risk factor for the OTC ertugliflozin. In some embodiments, the second series of filters includes a first liver disease filter, a first urinary problem filter, a first surgery filter, a first dietary filter, a first pancreatic disease filter, a first alcohol consumption filter, a first diabetes medication filter, an amputation history of the subject, a leg neuropathy history of the subject, and a diabetic foot ulcer history of the subject. The first liver disease filter is configured to ensure the subject has not ever had a liver problem. The first urinary problem filter is configured to ensure the subject does not have a history of urinary problems or a history of urinary tract infections or problems urinating. The first surgery filter is configured to ensure the subject is not planning to undergo surgery. The first dietary filter is configured to ensure the subject is not eating less than before, whether due to illness, surgery, or a recent change in diet. The first pancreatic disease filter is configured to ensure the subject does not have a pancreatic problem. The first alcohol consumption filter is configured to ensure the subject is not consuming, on average, more than a predetermined number of alcoholic drinks over a predetermined period of time. The first diabetes medication filter is configured to ensure the subject is not taking diabetes medication. The amputation filter is configured to ensure the subject does not have any amputated body parts. The leg neuropathy filter is configured to ensure the subject does not have a leg neuropathy. The diabetic foot ulcer filter is configured to ensure the subject does not have a diabetic foot ulcer.

The computer system then prompts the subject to acknowledge or deny having discussed these warnings with a medical professional (e.g., their physician or healthcare professional). The computer system then proceeds with a fulfillment process only when none of the first series of filters was fired and the subject acknowledged that they discussed each warning issued in association with the second series of filters that was fired.

The computer system stores an indication of an initial order of the OTC ertugliflozin in a subject profile, and communicates an over-the-counter drug facts label for the ertugliflozin pharmaceutical composition to the subject. Upon confirmation from the subject that they have received and read the over-the-counter drug facts label, the computer system authorizes provision of the OTC ertugliflozin pharmaceutical composition to the subject.

In some embodiments, the computer system includes instructions for conducting another survey of the subject responsive to a re-order request of the ertugliflozin pharmaceutical composition. This survey is utilized to obtain one or more results of: whether the subject is one of pregnant, breastfeeding, or planning to become pregnant, whether the subject has experienced a symptom of ketoacidosis since receiving their last provision of the dapagliflozin pharmaceutical composition, whether the subject has experienced a symptom of a kidney problem since receiving their last provision of the ertugliflozin pharmaceutical composition, whether the subject has experienced a symptom of a urinary problem since receiving their last provision of the ertugliflozin pharmaceutical composition, whether the subject has experienced a liver problem since receiving their last provision of the ertugliflozin pharmaceutical composition, a surgery status of the subject, a dietary status of the subject, whether the subject has experienced a pancreatic problem since receiving their last provision of the ertugliflozin pharmaceutical composition, an alcohol consumption status of the subject, whether the subject has experienced a yeast infection since receiving their last provision of the ertugliflozin pharmaceutical composition, whether the subject has experienced a symptom of hypoglycemia since receiving their last provision of the canagliflozin pharmaceutical composition, whether the subject is experiencing a bodily stress, and whether the subject is taking a diabetes medication.

The computer system runs survey results against a third series of filters that are each associated with the first filter category class. In some embodiments, the third series of filters includes one or more of a second pregnancy filter, a ketoacidosis symptom filter, a kidney problem filter, a second urinary problem filter, a bodily stress filter, and a second diabetes medication filter. This second pregnancy filter is configured to ensure the subject is not pregnant, breastfeeding, or planning to become pregnant within a predetermined period of time. The ketoacidosis filter is configured to ensure the subject has not experienced a symptom of ketoacidosis since receiving their last provision of dapagliflozin. Symptoms of ketoacidosis that are capable of firing the ketoacidosis symptom filter include an increase of ketones in the blood of the subject, an increase of ketones in the urine of the subject, nausea, tiredness, vomiting, trouble breathing, and abdominal pain. The kidney problem filter is configured to ensure the subject has not experienced symptoms of a kidney problem since receiving their last provision of dapagliflozin. Symptoms of a kidney problem that are capable of firing the kidney problem symptom filter include the subject is eating less than before, the subject is drinking less than before, vomiting, diarrhea, dehydration, and the subject being diagnosed with kidney disease. The second urinary problem filter is configured to ensure the subject has not experienced symptoms of a urinary tract infection since receiving their last provision of dapagliflozin. Symptoms of a urinary problem that are capable of firing the urinary problem filter include a burning sensation when passing urine, an increased urge to urinate, pelvic pain, blood in the urine, fever, back pain, nausea, and vomiting. The bodily stress filter is configured to ensure the subject is not undergoing a bodily stress. Bodily stresses that are capable of firing the bodily stress filter include fever, a recent trauma, an infection, and a recent surgery. The second diabetes filter is configured to ensure the subject is not taking a diabetes medication. The computer system runs survey results against a fourth series of filters that each generates a warning where the subject's survey results identify a risk factor for the OTC ertugliflozin. In some embodiments, the fourth series of filters includes a second liver disease filter, a second surgery filter, a second dietary filter, a second pancreatic disease filter, a second alcohol consumption filter, a yeast infection filter, and a hypoglycemia symptom filter. The second liver disease filter is configured to ensure the subject has not developed symptoms of liver disease since receiving their last provision of the ertugliflozin pharmaceutical composition. The second surgery filter is configured to ensure the subject is not planning on undergoing surgery. The second dietary filter is configured to ensure the subject is not eating less since receiving their last provision of the ertugliflozin pharmaceutical composition. The second pancreatic disease filter is configured to ensure the subject has not developed a pancreatic problem since receiving their last provision of the ertugliflozin pharmaceutical composition. The second alcohol consumption filter is configured to ensure the subject is not, on average, consuming more than a predetermined number of drinks over a predetermined time. The yeast infection filter is configured to ensure the subject has not experienced symptoms of a yeast infection since receiving their last provision of the ertugliflozin pharmaceutical composition. Yeast infections that are capable of firing the yeast infection filter include a yeast infection of the penis, a yeast infection of the vagina, a sore throat, an increased urge to urinate, an increased volume of urine, and an increased urge to urinate at night. The hypoglycemia symptom filter is configured to ensure the subject has not experienced symptoms of hypoglycemia since receiving their last provision of the ertugliflozin pharmaceutical composition. Symptoms of hypoglycemia that are capable of firing the hypoglycemia symptom filter include shaking, sweating, rapid heartbeat, change in vision, increased hunger, headaches, and a change in mood. The computer system then prompts the subject to acknowledge or deny having discussed these warnings with a medical professional (e.g., their physician or healthcare professional). The computer system then proceeds with a re-fulfillment process only when none of the third series of filters was fired the subject acknowledged that they discussed each warning issued in association with the fourth series of filters that was fired.

The computer system stores an indication of a re-order of the OTC ertugliflozin in the subject profile, and communicates the over-the-counter drug facts label for the ertugliflozin e pharmaceutical composition to the subject. Upon confirmation from the subject that they have received and read the over-the-counter drug facts label, the computer system authorizes provision of the OTC ertugliflozin pharmaceutical composition to the subject.

Example 4

A computer system is configured for qualifying a subject for over-the-counter delivery of a empagliflozin pharmaceutical composition to treat diabetes (e.g., by lowering blood sugar). The computer system includes instructions for conducting a survey of the subject. The survey is utilized to obtain one or more results of: whether the subject is one of pregnant, breastfeeding, or planning to become pregnant, a Type 1 diabetes status of the subject, a ketoacidosis status of the subject, a kidney disease status of the subject, an age of the subject, a blood sugar level of the subject, whether the subject has a liver problem, whether the subject has ever had a urinary problem, a surgery status of the subject, a dietary status of the subject, whether the subject has ever had a pancreatic problem, an alcohol consumption status of the subject, and whether the subject is taking a diabetes medication.

The computer system runs survey results against a first series of filters that are each associated with a first filter category class. The first filter category class is configured to prevent authorization for OTC delivery of the OTC empagliflozin when the subject's survey results identify a contraindication for the empagliflozin. In some embodiments, the first series of filters includes one or more of a first pregnancy filter, a Type 1 diabetes filter, a ketoacidosis filter, a first kidney disease filter, an age filter, and a first blood sugar filter. The first pregnancy filter is configured to ensure the subject is not pregnant, breastfeeding, or planning to become pregnant. The Type 1 diabetes filter is configured to ensure the subject does not have Type 1 diabetes. The ketoacidosis filter is configured to ensure the subject does not have ketoacidosis. The first kidney disease filter is configured to ensure that the subject does not have kidney disease. The age filter is configured to ensure the subject is greater than or equal to eighteen years old. The first blood sugar filter is configured to ensure that the subject has a blood sugar level that is either above a first baseline blood sugar level (e.g., 6.5% glycated hemoglobin) or below a ceiling blood sugar level (e.g., 8% glycated hemoglobin).

The computer system runs survey results against a second series of filters that each generates a warning where the subject's survey results identify a risk factor for the OTC empagliflozin. In some embodiments, the second series of filters includes a first liver disease filter, a first urinary problem filter, a first surgery filter, a first dietary filter, a first pancreatic disease filter, a first alcohol consumption filter, and a first diabetes medication filter. The first liver disease filter is configured to ensure the subject has not ever had a liver problem. The first urinary problem filter is configured to ensure the subject does not have a history of urinary problems or a history of urinary tract infections or problems urinating. The first surgery filter is configured to ensure the subject is not planning to undergo surgery. The first dietary filter is configured to ensure the subject is not eating less than before, whether due to illness, surgery, or a recent change in diet. The first pancreatic disease filter is configured to ensure the subject does not have a pancreatic problem. The first alcohol consumption filter is configured to ensure the subject is not consuming, on average, more than a predetermined number of alcoholic drinks over a predetermined period of time. The first diabetes medication filter is configured to ensure the subject is not taking diabetes medication.

The computer system then prompts the subject to acknowledge or deny having discussed these warnings with a medical professional (e.g., their physician or healthcare professional). The computer system then proceeds with a fulfillment process only when none of the first series of filters was fired and the subject acknowledged that they discussed each warning issued in association with the second series of filters that was fired.

The computer system stores an indication of an initial order of the OTC amlodipine in a subject profile, and communicates an over-the-counter drug facts label for the empagliflozin pharmaceutical composition to the subject. Upon confirmation from the subject that they have received and read the over-the-counter drug facts label, the computer system authorizes provision of the OTC empagliflozin pharmaceutical composition to the subject.

In some embodiments, the computer system includes instructions for conducting another survey of the subject responsive to a re-order request of the empagliflozin pharmaceutical composition. This survey is utilized to obtain one or more results of: whether the subject is one of pregnant, breastfeeding, or planning to become pregnant, whether the subject has experienced a symptom of ketoacidosis since receiving their last provision of the empagliflozin pharmaceutical composition, whether the subject has experienced a symptom of a kidney problem since receiving their last provision of the empagliflozin pharmaceutical composition, whether the subject has experienced a symptom of a urinary problem since receiving their last provision of the empagliflozin pharmaceutical composition, whether the subject has experienced a liver problem since receiving their last provision of the empagliflozin pharmaceutical composition, a surgery status of the subject, a dietary status of the subject, whether the subject has experienced a pancreatic problem since receiving their last provision of the empagliflozin pharmaceutical composition, an alcohol consumption status of the subject, whether the subject has experienced a yeast infection since receiving their last provision of the empagliflozin pharmaceutical composition, whether the subject has experienced a symptom of hypoglycemia since receiving their last provision of the empagliflozin pharmaceutical composition, whether the subject is experiencing a bodily stress, and whether the subject is taking a diabetes medication.

The computer system runs survey results against a third series of filters that are each associated with the first filter category class. In some embodiments, the third series of filters includes one or more of a second pregnancy filter, a ketoacidosis symptom filter, a kidney problem filter, a second urinary problem filter, a bodily stress filter, and a second diabetes medication filter. This second pregnancy filter is configured to ensure the subject is not pregnant, breastfeeding, or planning to become pregnant within a predetermined period of time. The ketoacidosis filter is configured to ensure the subject has not experienced a symptom of ketoacidosis since receiving their last provision of empagliflozin. Symptoms of ketoacidosis that are capable of firing the ketoacidosis symptom filter include an increase of ketones in the blood of the subject, an increase of ketones in the urine of the subject, nausea, tiredness, vomiting, trouble breathing, and abdominal pain. The kidney problem filter is configured to ensure the subject has not experienced symptoms of a kidney problem since receiving their last provision of empagliflozin. Symptoms of a kidney problem that are capable of firing the kidney problem symptom filter include the subject is eating less than before, the subject is drinking less than before, vomiting, diarrhea, dehydration, and the subject being diagnosed with kidney disease. The second urinary problem filter is configured to ensure the subject has not experienced symptoms of a urinary tract infection since receiving their last provision of empagliflozin. Symptoms of a urinary problem that are capable of firing the urinary problem filter include a burning sensation when passing urine, an increased urge to urinate, pelvic pain, blood in the urine, fever, back pain, nausea, and vomiting. The bodily stress filter is configured to ensure the subject is not undergoing a bodily stress. Bodily stresses that are capable of firing the bodily stress filter include fever, a recent trauma, an infection, and a recent surgery. The second diabetes filter is configured to ensure the subject is not taking a diabetes medication.

The computer system runs survey results against a fourth series of filters that each generates a warning where the subject's survey results identify a risk factor for the OTC amlodipine. In some embodiments, the fourth series of filters includes a second liver disease filter, a second surgery filter, a second dietary filter, a second pancreatic disease filter, a second alcohol consumption filter, a yeast infection filter, and a hypoglycemia symptom filter. The second liver disease filter is configured to be fired at least when the survey results indicates that the subject has developed symptoms of liver disease since receiving their last provision of the empagliflozin pharmaceutical composition. The second surgery filter is configured to ensure the subject is not planning on undergoing surgery. The second dietary filter is configured to ensure the subject is not eating less since receiving their last provision of the empagliflozin pharmaceutical composition. The second pancreatic disease filter is configured to ensure the subject has not developed a pancreatic problem since receiving their last provision of the empagliflozin pharmaceutical composition. The second alcohol consumption filter is configured to ensure the subject is not, on average, consuming more than a predetermined number of drinks over a predetermined time. The yeast infection filter is configured to ensure the subject has not experienced symptoms of a yeast infection since receiving their last provision of the empagliflozin pharmaceutical composition. Yeast infections that are capable of firing the yeast infection filter include a yeast infection of the penis, a yeast infection of the vagina, a sore throat, an increased urge to urinate, an increased volume of urine, and an increased urge to urinate at night. The hypoglycemia symptom filter is configured to ensure the subject has not experienced symptoms of hypoglycemia since receiving their last provision of the empagliflozin pharmaceutical composition. Symptoms of hypoglycemia that are capable of firing the hypoglycemia symptom filter include shaking, sweating, rapid heartbeat, change in vision, increased hunger, headaches, and a change in mood.

The computer system then prompts the subject to acknowledge or deny having discussed these warnings with a medical professional (e.g., their physician or healthcare professional). The computer system then proceeds with a re-fulfillment process only when none of the third series of filters was fired the subject acknowledged that they discussed each warning issued in association with the fourth series of filters that was fired.

The computer system stores an indication of a re-order of the OTC empagliflozin in the subject profile, and communicates the over-the-counter drug facts label for the empagliflozin pharmaceutical composition to the subject. Upon confirmation from the subject that they have received and read the over-the-counter drug facts label, the computer system authorizes provision of the OTC empagliflozin pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

Figures 5C, 5D:
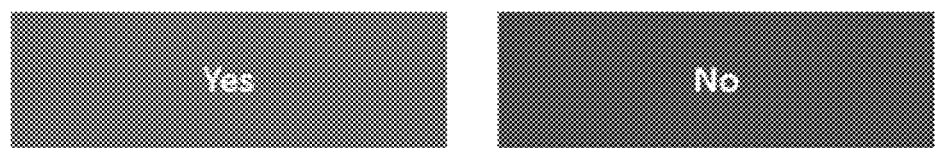

The present invention can be implemented as a computer program product that includes a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of lowering blood sugar in a human subject with an over-the-counter gliflozin Sodium-Glucose Cotransport 2 inhibitor pharmaceutical composition, the method comprising:
  A) providing a first survey for obtaining a first plurality of survey results about the subject, via a first computer system having a processor programed to perform the first survey, wherein the first plurality of survey results comprises:
    whether the subject is one of (i) pregnant, (ii) breastfeeding, or (iii) planning to become pregnant,
    a Type 1 diabetes status of the subject,
    a ketoacidosis status of the subject,
    a kidney disease status of the subject,
    an age of the subject,
    a blood sugar level of the subject,
    whether the subject has a liver problem,
    whether the subject has ever had a urinary problem,
    a surgery status of the subject,
    a dietary status of the subject,
    whether the subject has ever had a pancreatic problem,
    an alcohol consumption status of the subject,
    whether the subject is taking a diabetes medication; and
  B) applying an algorithm to the first plurality of survey results, via a second computer system having a process programed to perform the algorithm, wherein the algorithm:
    i) runs all or a portion of the first plurality of survey results against a first plurality of filters of a first category class, wherein, when a respective filter in the first plurality of filters is fired, the subject is deemed not qualified for delivery of the gliflozin Sodium-Glucose Cotransport 2 inhibitor pharmaceutical composition and the method is terminated without authorizing provision of the gliflozin Sodium- Glucose Cotransport 2 inhibitor pharmaceutical composition to the subject, wherein the first plurality of filters comprises:
  a first pregnancy filter that is fired at least when the first plurality of survey results indicates that the subject is pregnant or the subject is breastfeeding,
  a Type 1 diabetes filter that is fired at least when the first plurality of survey results indicates that the subject has Type 1 diabetes,
  a ketoacidosis filter that is fired at least when the first plurality of survey results indicates that the subject has ketoacidosis,
  a first kidney disease filter that is fired at least when the first plurality of survey results indicates that the subject has kidney disease,
  an age filter, and
  a first blood sugar filter that is fired at least when the first plurality of survey results indicates that the subject has a blood sugar level that is either (i) below a first baseline blood sugar level or (ii) above a ceiling blood sugar level;
ii) runs all or a portion of the first plurality of survey results against a second plurality of filters of a second category class, wherein, when a respective filter in the second plurality of filters is fired, the subject is provided with a warning corresponding to the respective filter, and wherein the second plurality of filters comprises:
  a first liver disease filter that is fired at least when the first plurality of survey results indicates that the subject has a liver problem,
  a first urinary problem filter that is fired at least when the first plurality of survey results indicates that the subject has a history of urinary problems,
  a first surgery filter that is fired at least when the first plurality of survey results indicates that the subject is planning on undergoing surgery,
  a first dietary filter that is fired at least when the first plurality of survey results indicates that the subject is eating less than before,
  a first pancreatic disease filter that is fired at least when the first plurality of survey results indicates that the subject has had a pancreatic problem,
  a first alcohol consumption filter, and
  a first diabetes medication filter that is fired at least when the first plurality of survey results indicates that the subject is taking a diabetes medication;
iii) obtains acknowledgment from the subject for each warning issued to the subject by any filter in the second plurality of filters;
iv) proceeds with a fulfillment process when a) no filter in the first plurality of filters has been fired and b) ithe subject has acknowledged each warning associated with each filter in the second plurality of filters that was fired, wherein the fulfillment process comprises:
  storing an indication in a subject profile of an initial order for the gliflozin Sodium-Glucose Cotransport 2 inhibitor pharmaceutical composition,
  communicating an over-the-counter drug facts label for the gliflozin Sodium-Glucose Cotransport 2 inhibitor pharmaceutical composition to the subject, and
  authorizing, upon confirmation from the subject that the over-the-counter drug facts label has been received and read, provision of the gliflozin Sodium-Glucose Cotransport 2 inhibitor pharmaceutical composition to the subject; and
(C) administering the gliflozin Sodium-Glucose Cotransport 2 inhibitor pharmaceutical composition to the subject after authorization of the provision.

2. The method of claim 1, wherein the gliflozin Sodium-Glucose Cotransport 2 inhibitor pharmaceutical composition comprises dapagliflozin or a pharmaceutically acceptable salt thereof.

3. The method of claim 1, wherein the gliflozin Sodium-Glucose Cotransport 2 inhibitor pharmaceutical composition is dapagliflozin propanediol.

4. The method of claim 1, wherein the subject is administered a dosage of from 5 mg to 10 mg per day of the gliflozin Sodium-Glucose Cotransport inhibitor pharmaceutical composition.

5. The method of claim 1, wherein the subject is administered a dosage of 5 mg per day of the gliflozin Sodium-Glucose Cotransport inhibitor pharmaceutical composition.

6. The method of claim 1, wherein the gliflozin Sodium-Glucose Cotransport inhibitor pharmaceutical composition comprises an active ingredient selected from the group consisting of empagliflozin, canagliflozin, and ertugliflozin.

7. The method of claim 1, wherein the first baseline blood sugar level used in the first blood sugar filter is 6.5% glycated hemoglobin.

8. The method of claim 1, wherein the ceiling blood sugar level used in the first blood sugar filter is 8% glycated hemoglobin.

9. The method of claim 1, wherein:
  the first plurality of survey results further comprises whether the subject is allergic to the gliflozin Sodium-Glucose Cotransport 2 inhibitor pharmaceutical composition, and
  the first plurality of filters includes an adverse reaction filter that is fired when the first plurality of survey results indicates that the subject is allergic to the gliflozin Sodium-Glucose Cotransport 2 inhibitor pharmaceutical composition.

10. The method of claim 1, wherein:
  the first plurality of survey results further comprises whether the subject has ever had bladder cancer, and
  the first plurality of filters includes a first bladder cancer filter that is fired-when the first plurality of survey results indicates that the subject has had bladder cancer.

11. The method of claim 1, wherein:
  the warning corresponding to a respective filter in the second plurality of filters comprises a prompt for the subject to indicate whether they have discussed the risk factor underlying the respective filter in the second plurality of filters that was fired with a health care professional; and
  acknowledgement is obtained from the subject when the subject indicates that they have discussed the risk factor underlying the respective filter in the second plurality of filters that was fired with a health care professional.

12. The method of claim 1, further comprising:
D) responsive to receiving a re-order request from the subject for the gliflozin Sodium-Glucose Cotransport 2 inhibitor blocker pharmaceutical composition, performing a re-fulfillment procedure, via a third computer system having a processor programed to perform the re-fulfillment procedure, the re-fulfillment procedure comprising:

i) providing a second survey for obtaining a second plurality of survey results about the subject, wherein the second plurality of survey results comprises information indicating:
  whether the subject is one of (i) pregnant, (ii) breast-feeding, or (iii) planning to become pregnant,
  whether the subject has developed ketoacidosis since receiving their last provision of the gliflozin Sodium-Glucose Cotransport 2 inhibitor pharmaceutical composition,
  whether the subject has developed a kidney problem since receiving their last provision of the gliflozin Sodium-Glucose Cotransport 2 inhibitor pharmaceutical composition,
  whether the subject has developed a urinary problem since receiving their last provision of the gliflozin Sodium-Glucose Cotransport 2 inhibitor pharmaceutical composition,
  whether the subject has developed a liver problem since receiving their last provision of the gliflozin Sodium-Glucose Cotransport 2 inhibitor pharmaceutical composition,
  a surgery status of the subject,
  a dietary status of the subject,
  whether the subject has developed a pancreatic problem since receiving their last provision of the gliflozin Sodium-Glucose Cotransport 2 inhibitor pharmaceutical composition,
  an alcohol consumption status of the subject,
  whether the subject has experienced a yeast infection since receiving their last provision of the gliflozin Sodium-Glucose Cotransport 2 inhibitor pharmaceutical composition,
  whether the subject has developed hypoglycemia since receiving their last provision of the gliflozin Sodium-Glucose Cotransport 2 inhibitor pharmaceutical composition,
  whether the subject is experiencing a bodily stress, and
  whether the subject is taking a diabetes medication;
ii) running all or a portion of the second plurality of survey results against a third plurality of filters of the first category class, wherein, when a respective filter in the third plurality of filters is fired, the subject is deemed not qualified for the gliflozin Sodium-Glucose Cotransport 2 inhibitor pharmaceutical composition and the re-fulfillment process is terminated without authorizing provision of the gliflozin Sodium-Glucose Cotransport 2 inhibitor pharmaceutical composition to the subject, wherein the third plurality of filters comprise:
  a second pregnancy filter that is fired at least when the second plurality of survey results indicates that the subject is pregnant or the subject is breast-feeding,
  a ketoacidosis symptom filter that is fired at least when the second plurality of survey results indicates that the subject has developed ketoacidosis since receiving their last provision of the gliflozin Sodium-Glucose Cotransport 2 inhibitor pharmaceutical composition,
  a kidney problem filter that is fired at least when the second plurality of survey results indicates that the subject has developed a kidney problem since receiving their last provision of the gliflozin Sodium-Glucose Cotransport 2 inhibitor pharmaceutical composition,
  a second urinary problem filter that is fired at least when the second plurality of survey results indicates that the subject has developed a urinary tract infection since receiving their last provision of the gliflozin Sodium-Glucose Cotransport 2 inhibitor pharmaceutical composition,
  a bodily stress filter that is fired at least when the second plurality of survey results indicates that the subject is experiencing a bodily stress, and
  a second diabetes medication filter that is fired at least when the second plurality of survey results indicates that the subject is taking a diabetes medication;
iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises:
  a second liver disease filter that is fired at least when the second plurality of survey results indicates that the subject has developed a liver problem since receiving their last provision of the gliflozin Sodium-Glucose Cotransport 2 inhibitor pharmaceutical composition,
  a second surgery filter that is fired at least when the second plurality of survey results indicates that the subject is planning on undergoing surgery,
  a second dietary filter that is fired at least when the second plurality of survey results indicates that the subject is eating less than before receiving their last provision of the gliflozin Sodium-Glucose Cotransport 2 inhibitor pharmaceutical composition,
  a second pancreatic disease filter that is fired at least when the second plurality of survey results indicates that the subject has developed a pancreatic problem since receiving their last provision of the gliflozin Sodium-Glucose Cotransport 2 inhibitor pharmaceutical composition,
  a second alcohol consumption filter,
  a yeast infection filter that is fired at least when the second plurality of survey results indicates that the subject has experienced a yeast infection since receiving their last provision of the gliflozin Sodium-Glucose Cotransport 2 inhibitor pharmaceutical composition, and
  a hypoglycemia symptom filter that is fired at least when the second plurality of survey results indicates that the subject has developed hypoglycemia since receiving their last provision of the gliflozin Sodium-Glucose Cotransport 2 inhibitor pharmaceutical composition;
iv) obtaining acknowledgment from the subject for the warning issued to the subject by any filter in the fourth plurality of filters; and
v) proceeding with the re-fulfillment process when a) the re-fulfillment process is not already terminated by the firing of a filter in the third plurality of filters and b) the subject has acknowledged each warning associated with each filter in the third plurality of filters that was fired and that is associated with a warning, wherein the re-fulfillment process further comprises:

storing an indication in the subject profile of a re-order for the gliflozin Sodium-Glucose Cotransport 2 inhibitor pharmaceutical composition, communicating the over-the-counter drug facts label for the gliflozin Sodium-Glucose Cotransport 2 inhibitor pharmaceutical composition to the subject, and authorizing, upon confirmation from the subject that the over-the-counter drug facts label has been received and read, a re-order provision of the gliflozin Sodium-Glucose Cotransport 2 inhibitor pharmaceutical composition to the subject; and E) administering the Sodium-Glucose Cotransport 2 inhibitor pharmaceutical composition to the subject after authorization of the re-order provision.

13. The method of claim 12, wherein a bodily stress, which is capable of firing the bodily stress filter, is selected from the group consisting of a fever, a recent trauma, an infection, and a recent surgery.

14. The method of claim 12, wherein:

the second plurality of survey results further comprises whether the subject has experienced a symptom of dehydration since receiving their last provision of the gliflozin Sodium-Glucose Cotransport 2 inhibitor pharmaceutical composition, and the fourth plurality of filters further comprises a dehydration filter that is fired at least when the second plurality of survey results indicates that the subject has experienced, since receiving their last provision of the gliflozin Sodium-Glucose Cotransport 2 inhibitor pharmaceutical composition, a symptom of dehydration selected from the group consisting of dizziness, faintness, light-headedness, and weakness.

15. The method of claim 12, wherein:

the second plurality of survey results further comprises a bladder cancer status of the subject, and the third plurality of filters further comprises a second bladder cancer filter that is fired at least when the second plurality of survey results indicates that the subject has developed bladder cancer since receiving their last provision of the gliflozin Sodium-Glucose Cotransport 2 inhibitor pharmaceutical composition.

16. The method of claim 12, wherein when the subject profile for the subject does not include a recent blood sugar status for the subject:

the second plurality of survey results further comprises a blood sugar status of the subject; and the third plurality of filters of the first category class further comprises a second blood sugar filter that is fired at least when the second plurality of survey results indicates that the subject has a blood sugar level of at least a second baseline blood sugar level.

17. The method of claim 12, wherein:

the second plurality of survey results further comprises a blood sugar status of the subject; and the third plurality of filters of the first category class further comprises a second blood sugar filter that is fired at least when the second plurality of survey results indicates that the subject has a blood sugar level of at least a second baseline blood sugar level.

18. The method of claim 1, wherein:

the gliflozin Sodium-Glucose Cotransport 2 inhibitor pharmaceutical composition is canagliflozin;

the first plurality of survey results further comprises one or more survey results selected from the group consisting of:

a heart failure history of the subject, an amputation history of the subject, a leg neuropathy history of the subject, a diabetic foot ulcer history of the subject, and a hyperkalemia history of the subject; and the first plurality of filters and/or the second plurality of filters further comprises one or more filters selected from the group consisting of:

a heart failure filter that is triggered at least when the first plurality of survey results indicates that the subject has a history of heart failure;

an amputation filter that is triggered at least when the first plurality of survey results indicates that the subject has a body part amputated;

a leg neuropathy filter that is triggered at least when the first plurality of survey results indicates that the subject has a leg neuropathy;

a diabetic foot ulcer filter that is triggered at least when the first plurality of survey results indicates that the subject has a diabetic foot ulcer; and a hyperkalemia filter that is triggered at least when the first plurality of survey results indicates that the subject has hyperkalemia.

19. The method of claim 1, wherein:

the gliflozin Sodium-Glucose Cotransport 2 inhibitor pharmaceutical composition is ertugliflozin;

the first plurality of survey results further comprises one or more survey results selected from the group consisting of:

an amputation history of the subject, a leg neuropathy history of the subject, and a diabetic foot ulcer history of the subject; and the first plurality of filters and/or the second plurality of filters further comprises one or more filters selected from the group consisting of:

an amputation filter that is triggered at least when the first plurality of survey results indicates that the subject has a body part amputated;

a leg neuropathy filter that is triggered at least when the first plurality of survey results indicates that the subject has a leg neuropathy; and a diabetic foot ulcer filter that is triggered at least when the first plurality of survey results indicates that the subject has a diabetic foot ulcer.

* * * * *